(12) United States Patent
Brittain et al.

(10) Patent No.: US 9,556,189 B2
(45) Date of Patent: Jan. 31, 2017

(54) POLYMORPHIC FORMS OF NALTREXONE

(71) Applicant: Alkermes Pharma Ireland Limited, Dublin (IE)

(72) Inventors: Harry G. Brittain, Milford, NJ (US); David A. Dickason, Cincinnati, OH (US); Joyce M. Hotz, Cincinnati, OH (US); Shawn L. Lyons, Cincinnati, OH (US); J. Michael Ramstack, Lunenburg, MA (US); Steven G. Wright, Madeira, OH (US)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

(21) Appl. No.: 15/175,399

(22) Filed: Jun. 7, 2016

(65) Prior Publication Data

US 2016/0362415 A1 Dec. 15, 2016

Related U.S. Application Data

(60) Continuation of application No. 14/945,607, filed on Nov. 19, 2015, now Pat. No. 9,365,580, which is a continuation of application No. 14/612,904, filed on Feb. 3, 2015, now Pat. No. 9,221,803, which is a continuation of application No. 14/249,613, filed on Apr. 10, 2014, now Pat. No. 8,975,272, which is a continuation of application No. 13/690,327, filed on Nov. 30, 2012, now Pat. No. 8,735,420, which is a continuation of application No. 11/860,677, filed on Sep. 25, 2007, now Pat. No. 8,389,540, which is a division of application No. 10/860,608, filed on Jun. 3, 2004, now Pat. No. 7,279,579.

(60) Provisional application No. 60/475,863, filed on Jun. 4, 2003.

(51) Int. Cl.
*A61K 31/485* (2006.01)
*C07D 489/08* (2006.01)
*C07C 19/03* (2006.01)
*C07D 489/06* (2006.01)

(52) U.S. Cl.
CPC ............ *C07D 489/06* (2013.01); *A61K 31/485* (2013.01); *C07C 19/03* (2013.01); *C07D 489/08* (2013.01)

(58) Field of Classification Search
CPC ......................... C07D 489/08; C07B 2200/13
USPC ............................................. 514/282; 546/45
See application file for complete search history.

(56) References Cited

U.S. PATENT DOCUMENTS 4,141,897 A * 2/1979 Olofson ............... C07D 489/08
546/44

* cited by examiner

*Primary Examiner* — Kristin Vajda
(74) *Attorney, Agent, or Firm* — Elmore Patent Law Group, P.C.; Edgar W. Harlan; Carolyn S. Elmore

(57) ABSTRACT

This invention relates to the discovery of novel polymorphic forms of naltrexone, including solvates, hydrates, anhydrous and other crystalline forms and combinations thereof. These novel forms of naltrexone impart advantages in pharmaceutical formulations incorporating them, including sustained release, or long acting, formulations.

4 Claims, 78 Drawing Sheets

POLYMORPHIC FORMS OF NALTREXONE

RELATED APPLICATIONS

This application is a continuation of U.S. application Ser. No. 14/945,607, filed Nov. 19, 2015 which is a continuation of U.S. application Ser. No. 14/612,904, filed Feb. 3, 2015, now U.S. Pat. No. 9,221,803, issued Dec. 29, 2015, which is a continuation of U.S. application Ser. No. 14/249,613, filed Apr. 10, 2014, now U.S. Pat. No. 8,975,272, issued Mar. 10, 2015, which is a continuation of U.S. application Ser. No. 13/690,327, filed Nov. 30, 2012, now U.S. Pat. No. 8,735,420, issued May 27, 2014, which is a continuation of U.S. application Ser. No. 11/860,677, filed Sep. 25, 2007, now U.S. Pat. No. 8,389,540, issued Mar. 5, 2013, which is a divisional of U.S. application Ser. No. 10/860,608, filed Jun. 3, 2004, now U.S. Pat. No. 7,279,579, issued Oct. 9, 2007, which claims the benefit of U.S. Provisional Application No. 60/475,863 filed on Jun. 4, 2003. The entire teachings of the above applications are incorporated herein by reference.

BACKGROUND OF THE INVENTION

Alcohol dependence is a prevalent disease with substantial morbidity and mortality. Detoxification and psychosocial therapy provide the basis of treatment; in addition, pharmacotherapy is becoming widely accepted. Administered orally, naltrexone, a potent opioid antagonist, has been shown to reduce relapse to heavy drinking in alcohol dependent patients, decrease the number of drinks consumed when relapse does occur, and promote abstinence. Naltrexone has been reported to reduce both craving and the reinforcing euphoric qualities of alcohol.

Although naltrexone has been shown to be effective as a maintenance agent in the treatment of alcohol dependence, a major limitation of its utility can be poor adherence to therapy. In the treatment of alcohol abuse, oral naltrexone must be taken on a daily basis. In a clinical trial comparing oral naltrexone to placebo, greater than 40% of patients treated with naltrexone were noncompliant with the daily oral regimen. In medication-noncompliant patients relapse to clinically significant drinking was similar to placebo treated patients and significantly higher than the rate observed with medication-compliant patients.

Polymorphs, solvates and salts of various drugs have been described in the literature as imparting novel properties upon the drug. These polymorphs can have different solubilities, stabilities and processing characteristics, presenting opportunities and challenges.

SUMMARY OF THE INVENTION

This invention relates to the discovery of novel amorphous and polymorphic forms of naltrexone, including solvates, solvatomorphs, hydrates, anhydrous and other crystalline forms and combinations thereof. These novel forms of naltrexone impart advantages in pharmaceutical formulations incorporating them, including sustained release, or long acting, formulations. The solvates, or solvatomorphs, can include stoichiometric and non-stoichiometric solvates, such as clathrates, for example.

The present invention provides polymorphic forms of naltrexone which are characterized by X-ray Powder Diffraction (XRPD), differential scanning calorimetry (DSC) or attenuated total reflectance infrared absorption spectroscopy (IR-ATR).

The present invention advantageously provides novel polymorphic forms of naltrexone comprising naltrexone ethanolate, anhydrous naltrexone, naltrexone monohydrate, benzyl alcohol solvate and other polymorphs of naltrexone either isolated or in combination.

In another aspect, the invention, provides methods of making novel polymorphic forms of naltrexone comprising (i) mixing a naltrexone, such as a naltrexone base anhydrous and/or hydrochloride or other salt, with a solvent selected from the group consisting of acetonitrile, dimethyl formamide, water, methanol, ethanol, benzyl alcohol, dichloromethane, acetone, ethyl acetate, methyl ethyl ketone, toluene and hexane; (ii) heating the mixture to within 1-10° C. of the boiling point to prepare a nearly saturated solution; (iii) cooling the resulting nearly saturated solution to room temperature forming precipitated material; and (iv) harvesting the precipitated material.

A further aspect of the invention provides pharmaceutical compositions containing the naltrexone forms disclosed herein.

BRIEF DESCRIPTION OF THE DRAWINGS

The invention is illustrated, but in no way limited, by the Tables herein and the following examples, with reference to the figures in which.

DETAILED DESCRIPTION OF THE INVENTION

Figure 1A:
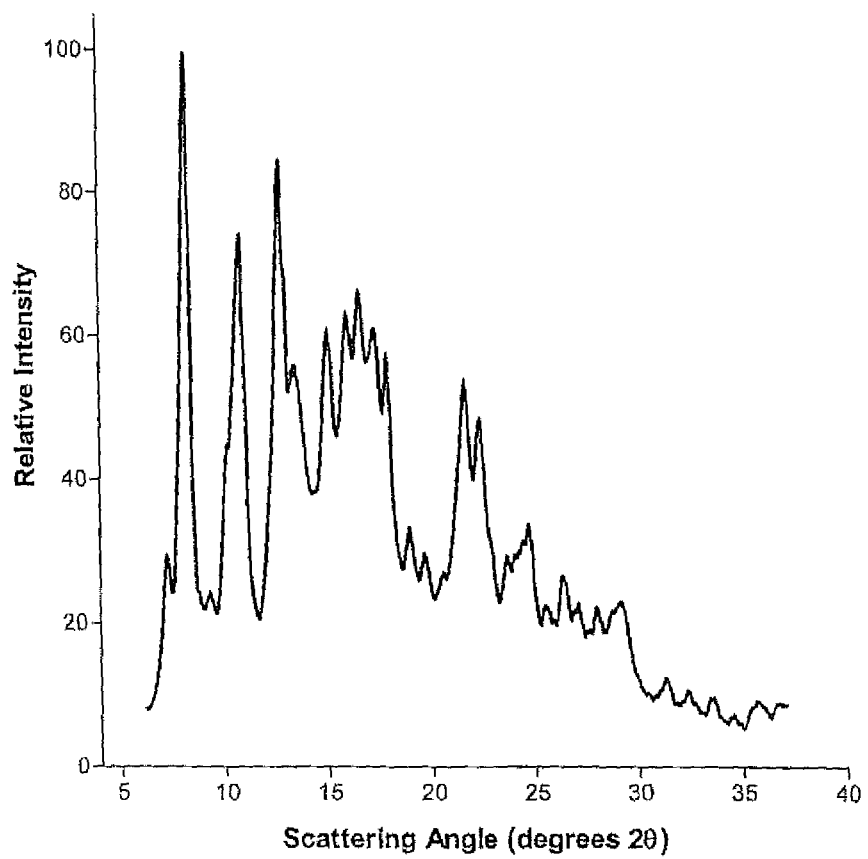
FIG. 1A is a graph depicting the X-ray Powder Diffraction (XRPD) patterns of crystalline naltrexone formed by slow cooling from acetonitrile (dipolar aprotic).

In the course of research, Applicants surprisingly discovered novel naltrexone polymorphs, including solvates, hydrates and anhydrous forms and combinations thereof. Further investigation led to the realization that favorable properties in naltrexone-containing microparticles were due to the crystalline forms and non-crystalline forms of the naltrexone contained within the microparticles. Applicants appreciated that the polymorphic forms of naltrexone crystalline, for example, the ethanol solvate form of naltrexone, have good to superior properties in naltrexone-containing compositions.

Pharmaceutical compositions when formulated for administration are useful in the treatment and prevention of, for example, narcotic or alcohol addiction and autism, as well as other naltrexone-based therapies.

As with all pharmaceutical compounds and compositions, the chemical and physical properties of the naltrexone form(s) utilized can be important in its commercial development. These properties include, but are not limited to: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture, and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, processing and storage of pharmaceutical compositions comprising naltrexone. Solid state forms of naltrexone that provide an improvement in one or more of these properties relative to other solid state forms of naltrexone are desirable.

The polymorphs of the invention and the compositions containing them have the advantage that they are in a form which provides for improved ease of handling. Further, depending upon the intended use, they have improved chemical and solid state stability. For example, they may be stable when stored over prolonged periods of time. They may be prepared in good yields, in higher purity, in less time, more conveniently and at a lower cost, than forms of naltrexone prepared previously.

1 Crystallization of Naltrexone in a Variety of Solvents

A series of naltrexone samples were generated by the crystallization of bulk drug substance at different rates out of a variety of solvents. These materials have been characterized by x-ray powder diffraction (XRPD), differential scanning calorimetry (DSC), and attenuated total reflectance infrared absorption spectroscopy (IR-ATR).

The isolated crystal form of a substance often is a function of the nature of the crystallization solvent and of the rate it is crystallized out of that solvent. The solvents in the following list include representatives from all solvent classes, and crystallization out of these enable unique crystal forms accessible to naltrexone.

TABLE 1

| Solvent System Type | Preferred Solvents |
|---|---|
| Dipolar aprotic | Acetonitrile, Dimethyl formamide |
| Protic | Water, Methanol, Ethanol, Benzyl alcohol |
| Lewis acidic | Dichloromethane |
| Lewis basic | Acetone, Ethyl acetate, Methyl ethyl ketone |
| Aromatic | Toluene |
| Non-polar | Hexane |

2. Methods for Identifying the Novel Forms

Applicants prepared substantially pure polymorphic forms of naltrexone using two separate processes. In one process, Applicant prepared the crystalline naltrexone polymorphs using a slow cooling process ("slow"). Commercially available naltrexone base anhydrous (Mallinckrodt) was dissolved in solvent forming a solvent system. The resulting solvent system was heated to within 1-10° C. of the boiling point for purpose of preparing a nearly saturated solution. The nearly saturated solution was then cooled to room temperature at a rate not greater than 1-2° C./min. The resulting precipitated material was harvested.

The second process was a fast cooling process ("fast") wherein naltrexone base anhydrous (Mallinckrodt) was dissolved in solvent forming a solvent system. The resulting solvent system was heated to within 5-10° C. of the boiling point for purpose of preparing a nearly saturated solution. The nearly saturated solution was then cooled as rapidly as possible to room temperature. The resulting precipitated material was harvested.

Table 2 below is a summary of each solvent used, which process was employed, and a reference to the Figure which shows the results of each of the three analytical methods performed.

3. X-Ray Powder Diffraction

Most of the various crystalline forms of naltrexone were analyzed using X-ray Powder Diffraction. X-ray powder diffraction (XRPD) patterns were obtained using a Rigaku MiniFlex powder diffraction system, equipped with a horizontal goniometer in the θ/2-θ mode. The x-ray source was nickel-filtered K-α emission of copper (1.54056 Å). Samples were packed into an aluminum holder using a back-fill procedure, and were scanned over the range of 50 to 6 degrees 2-θ, at a scan rate of 0.5 degrees 2-θ/min. Calibration of each powder pattern was effected using the characteristic scattering peaks of aluminum at 44.738 and 38.472 degrees 2-θ and these peaks are seen in the pattern. Other XRPDs were analyzed using a Bruker D8 Advance XRD or a SCINTAC X-ray diffractometer (model #XDS 2000), using 0.02°/step with a 1 second interval. Samples were scanned over the range of 2 to 40 degrees 2-θ at a scan rate of 1 degree 2-θ/min.

XRPD powder patterns of the various naltrexone precipitated materials obtained by the slow and fast cooling from a variety of solvent systems are shown herein in the Figures. The naltrexone forms of the invention are not limited to those made in accordance with the methods described herein.

4. Melting/Decomposition Temperature

The temperatures of melting and/or decomposition of naltrexone crystalline forms were determined using differential scanning calorimetry (DSC). Most DSC measurements, were obtained on a TA Instruments 2910 thermal analysis system. Samples of approximately 1-2 mg were accurately weighed into an aluminum DSC pan, and covered with an aluminum lid that was crimped in place. The samples were then heated over the range of 25-240° C., at a heating rate of 10° C./min.

TABLE 2

Figure 1B:
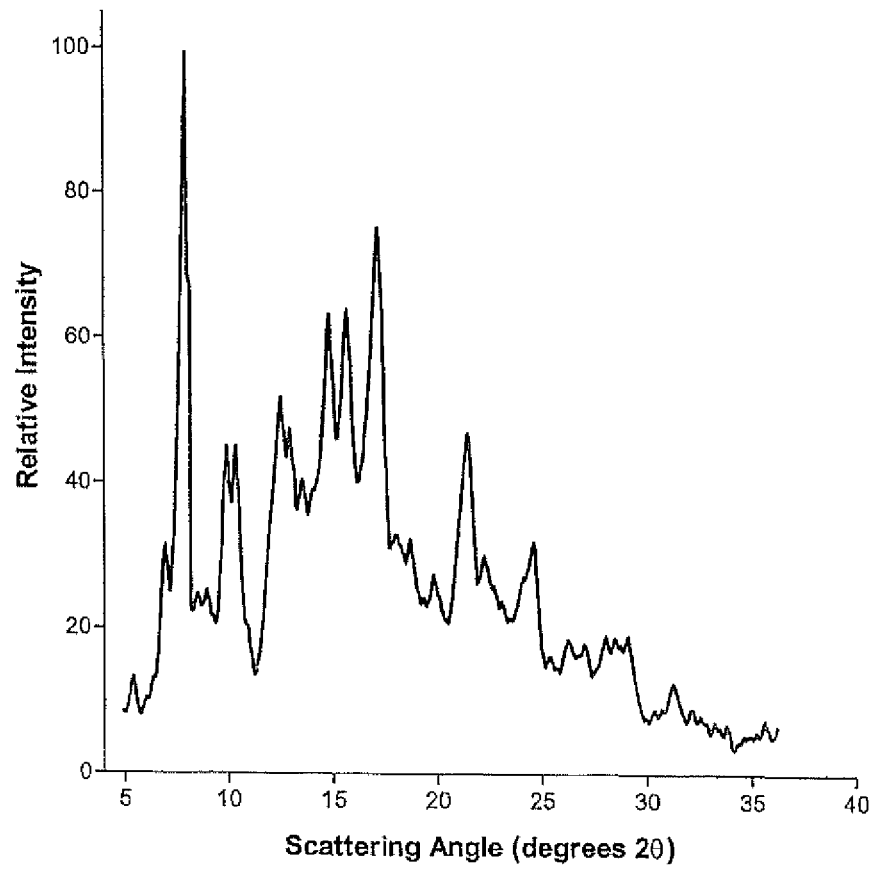
FIG. 1B is a graph depicting X-ray Powder Diffraction (XRPD) patterns of crystalline naltrexone formed by fast cooling using acetonitrile (dipolar aprotic).
Figure 2A:
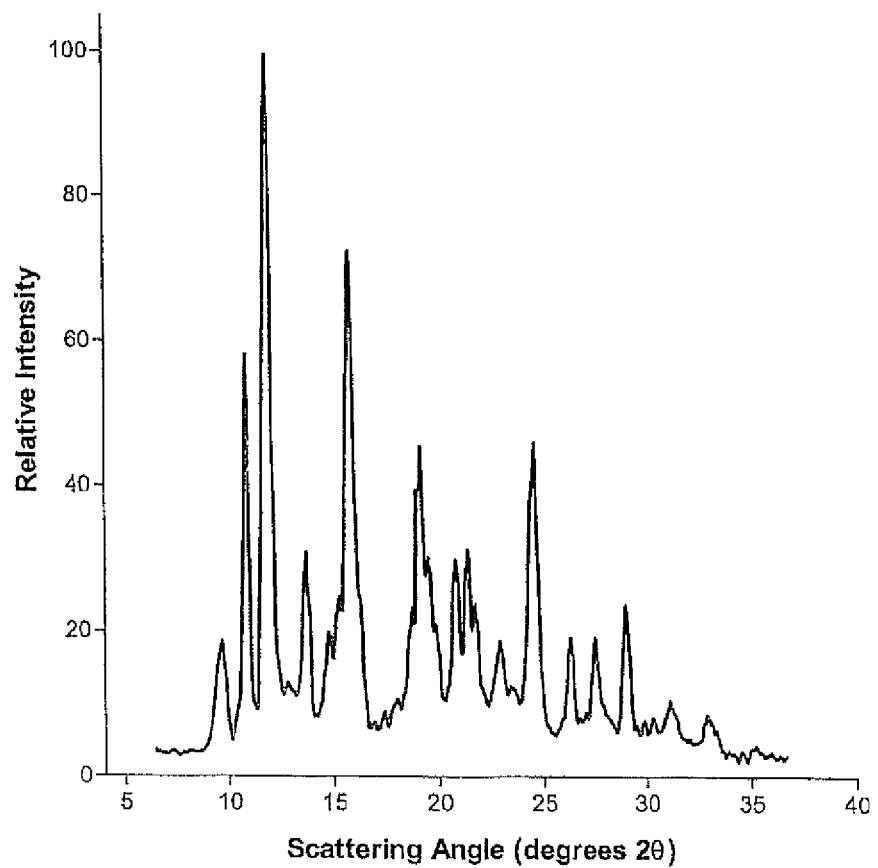
FIG. 2A is a graph depicting X-ray Powder Diffraction (XRPD) patterns of crystalline naltrexone formed by slow cooling using dimethyl formamide (dipolar aprotic).
Figure 2B:
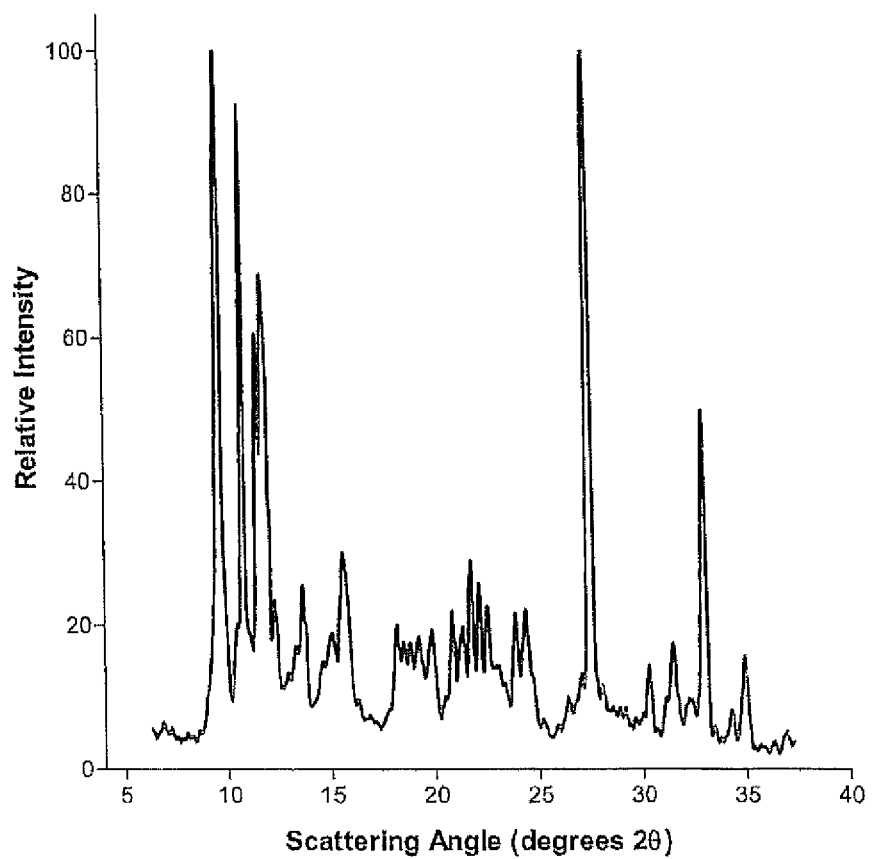
FIG. 2B is a graph depicting X-ray Powder Diffraction (XRPD) patterns of crystalline naltrexone formed by fast cooling using dimethyl formamide (dipolar aprotic).
Figure 3:
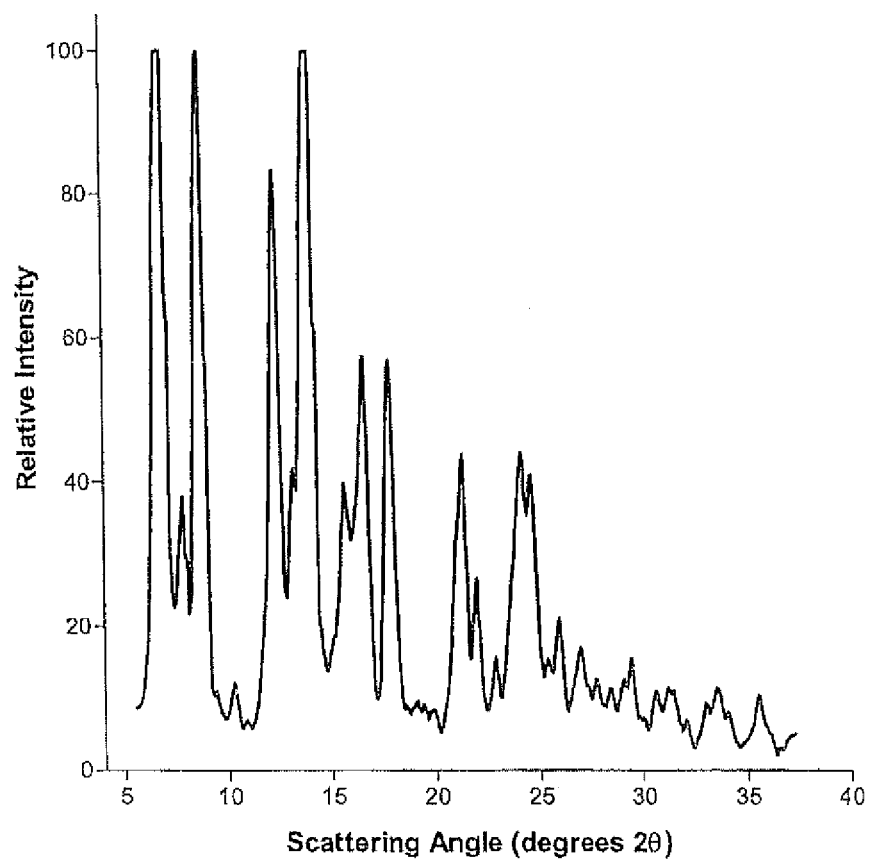
FIG. 3 is a graph depicting X-ray Powder Diffraction (XRPD) patterns of crystalline naltrexone formed by fast cooling using water (protic).
Figure 4A:
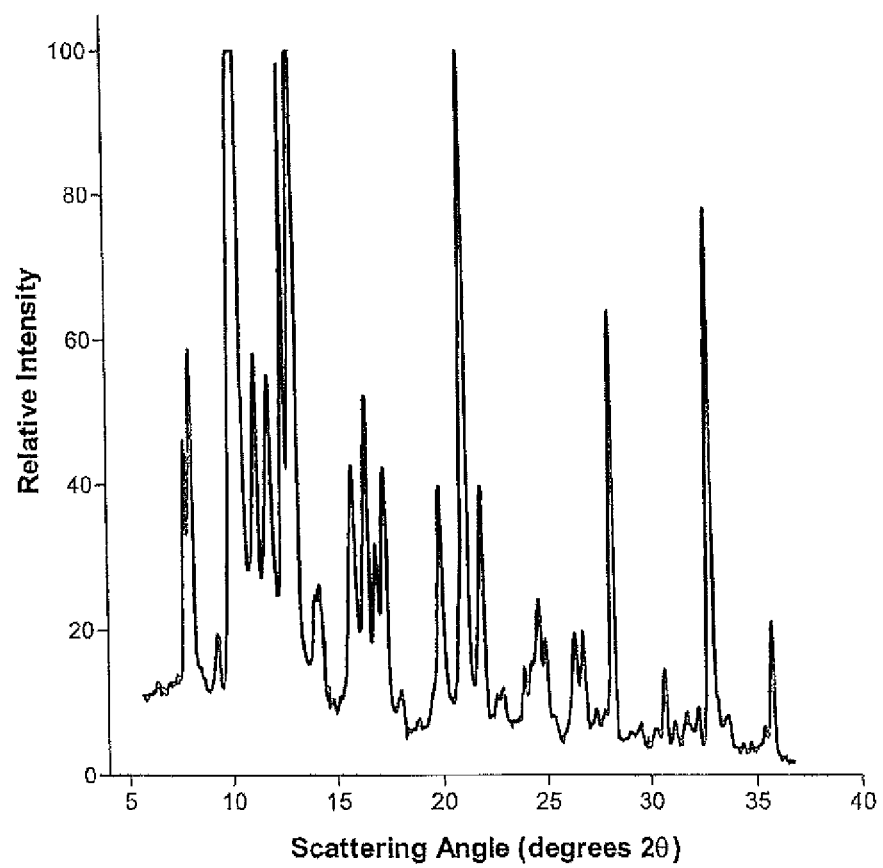
FIG. 4A is a graph depicting X-ray Powder Diffraction (XRPD) patterns of crystalline naltrexone formed by slow cooling using methanol (protic).
Figure 4B:
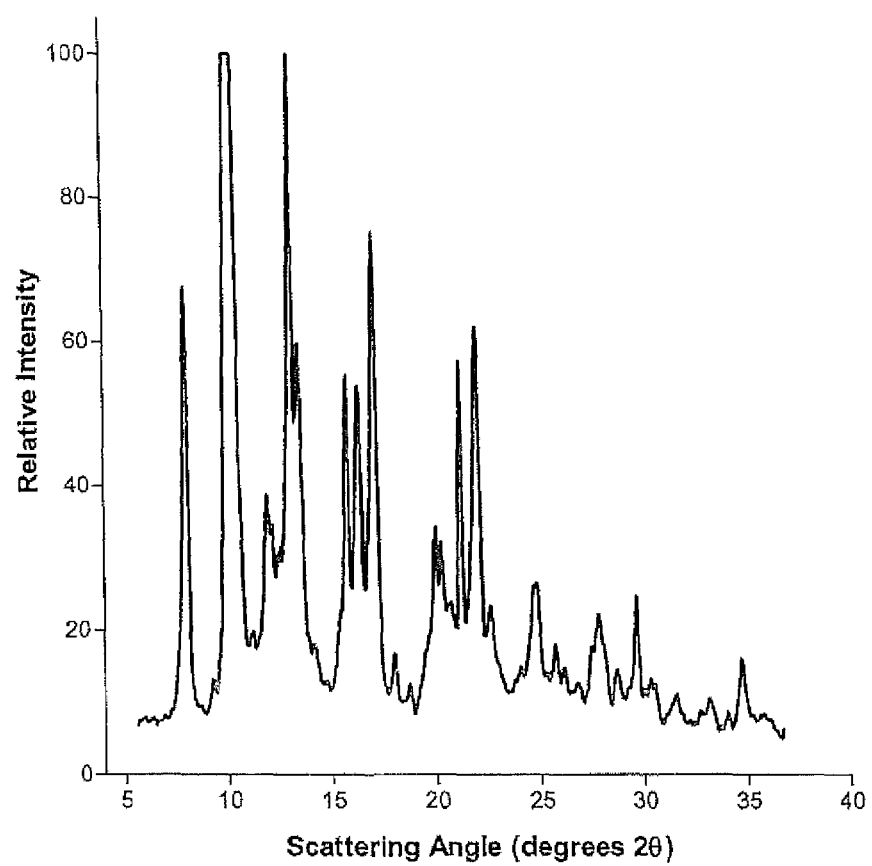
FIG. 4B is a graph depicting X-ray Powder Diffraction (XRPD) patterns of crystalline naltrexone formed by fast cooling using methanol (protic).
Figure 5A:
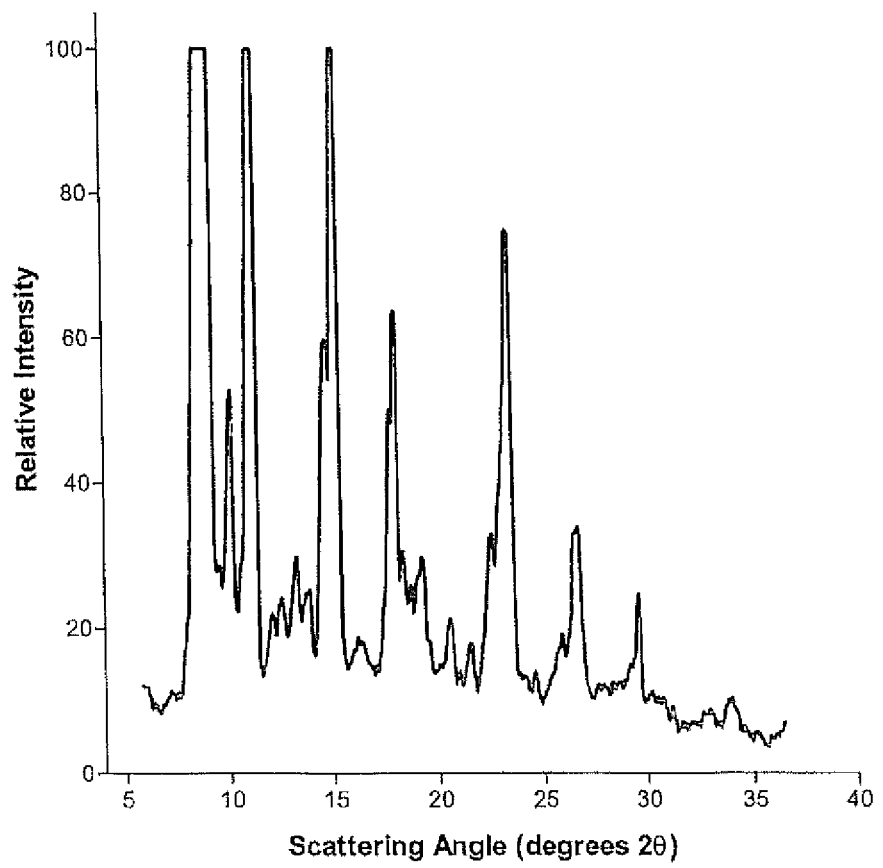
FIG. 5A is a graph depicting X-ray Powder Diffraction (XRPD) patterns of crystalline naltrexone formed by slow cooling using ethanol (protic).
Figure 5B:
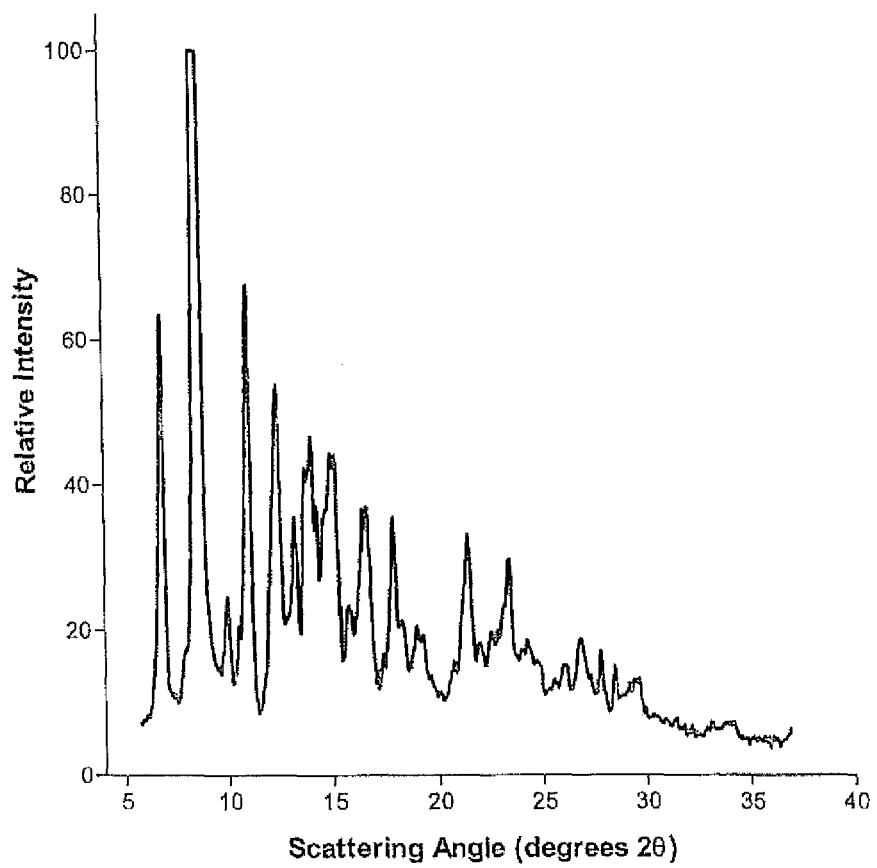
FIG. 5B is a graph depicting X-ray Powder Diffraction (XRPD) patterns of crystalline naltrexone formed by fast cooling using ethanol (protic).
Figure 6:
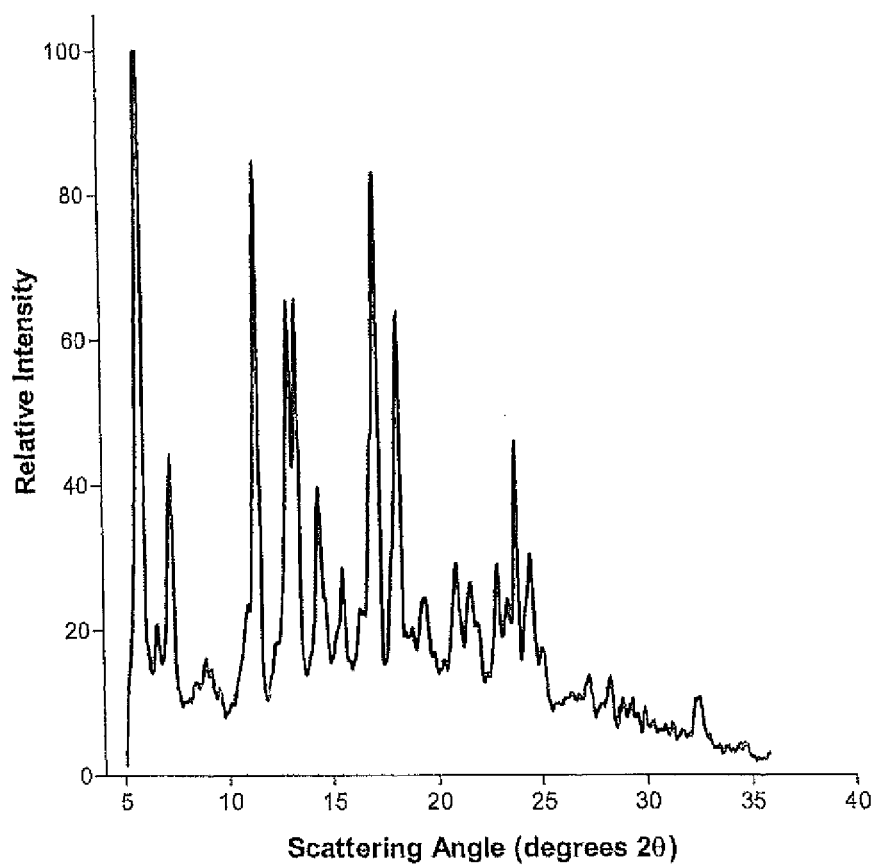
FIG. 6 is a graph depicting X-ray Powder Diffraction (XRPD) patterns of crystalline naltrexone formed by fast cooling using benzyl alcohol (protic).
Figure 7A:
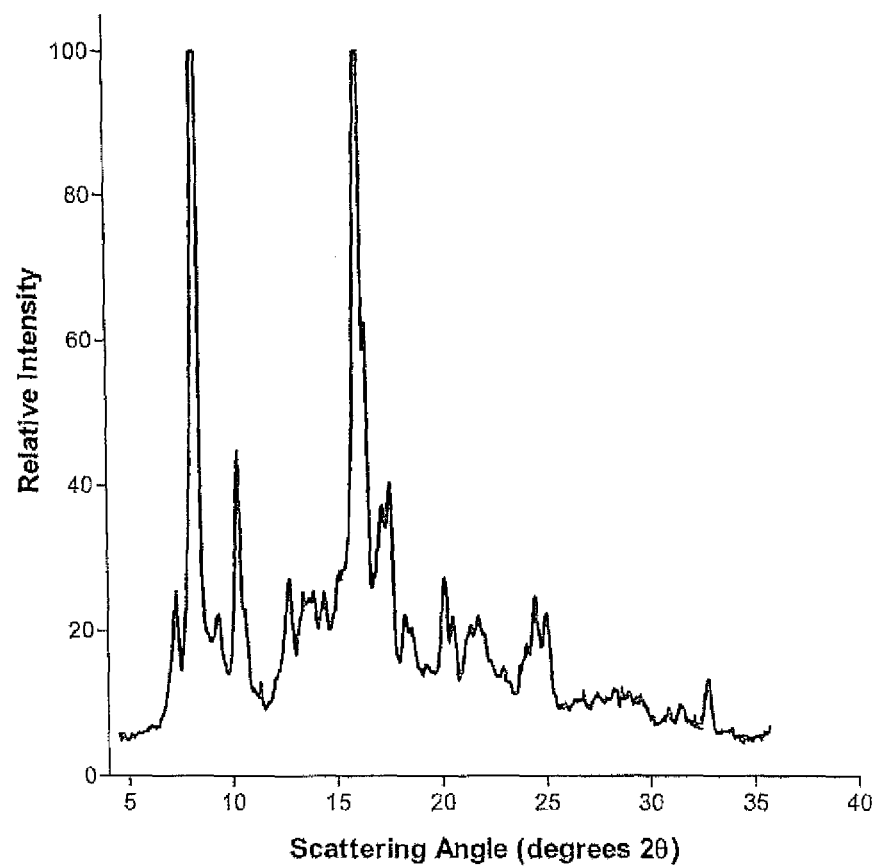
FIG. 7A is a graph depicting X-ray Powder Diffraction (XRPD) patterns of crystalline naltrexone formed by slow cooling using dichloromethane (Lewis acidic).
Figure 7B:
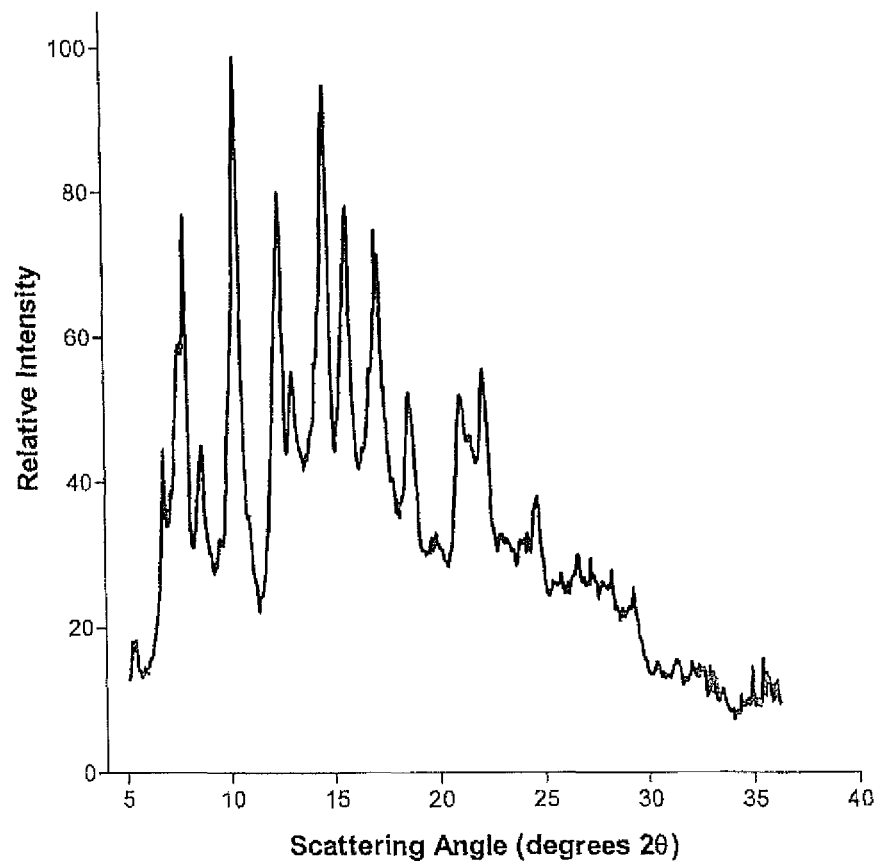
FIG. 7B is a graph depicting X-ray Powder Diffraction (XRPD) patterns of crystalline naltrexone formed by fast cooling using dichloromethane (Lewis acidic).
Figure 8A:
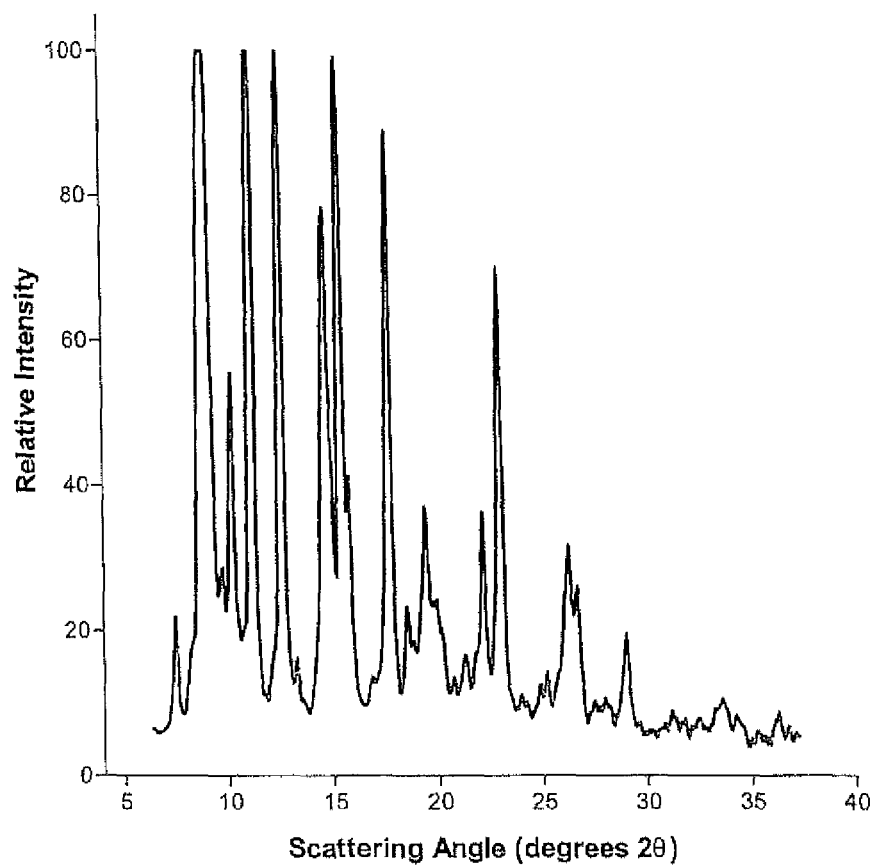
FIG. 8A is a graph depicting X-ray Powder Diffraction (XRPD) patterns of crystalline naltrexone formed by slow cooling using acetone (Lewis basic).
Figure 8B:
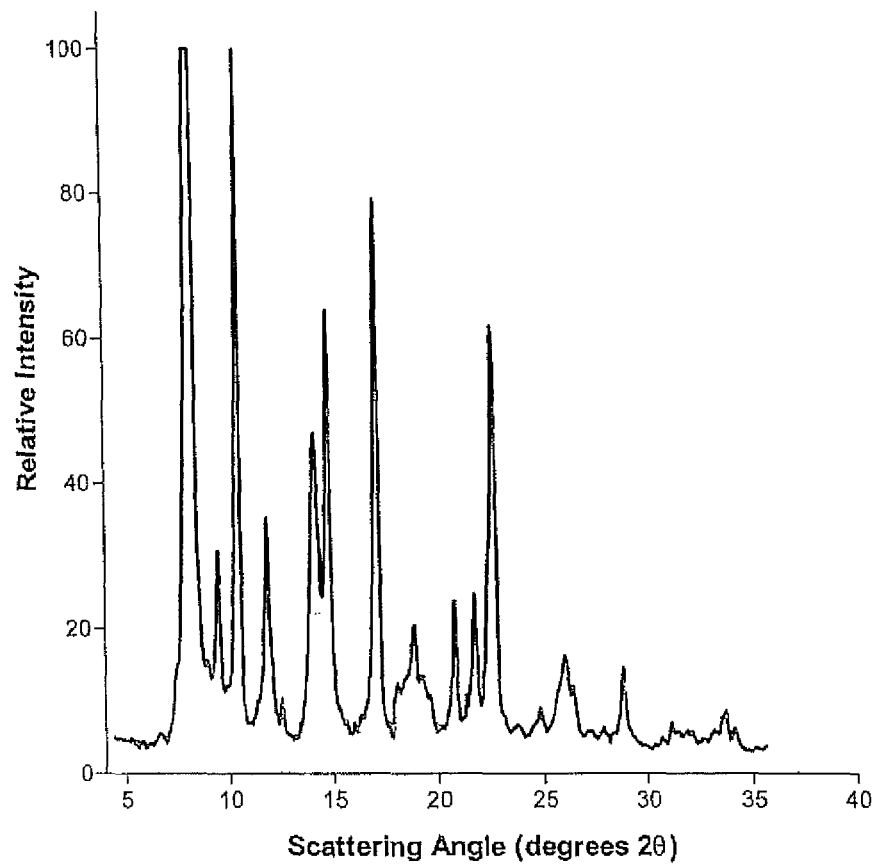
FIG. 8B is a graph depicting X-ray Powder Diffraction (XRPD) patterns of crystalline naltrexone formed by fast cooling using acetone (Lewis basic).
Figure 9A:
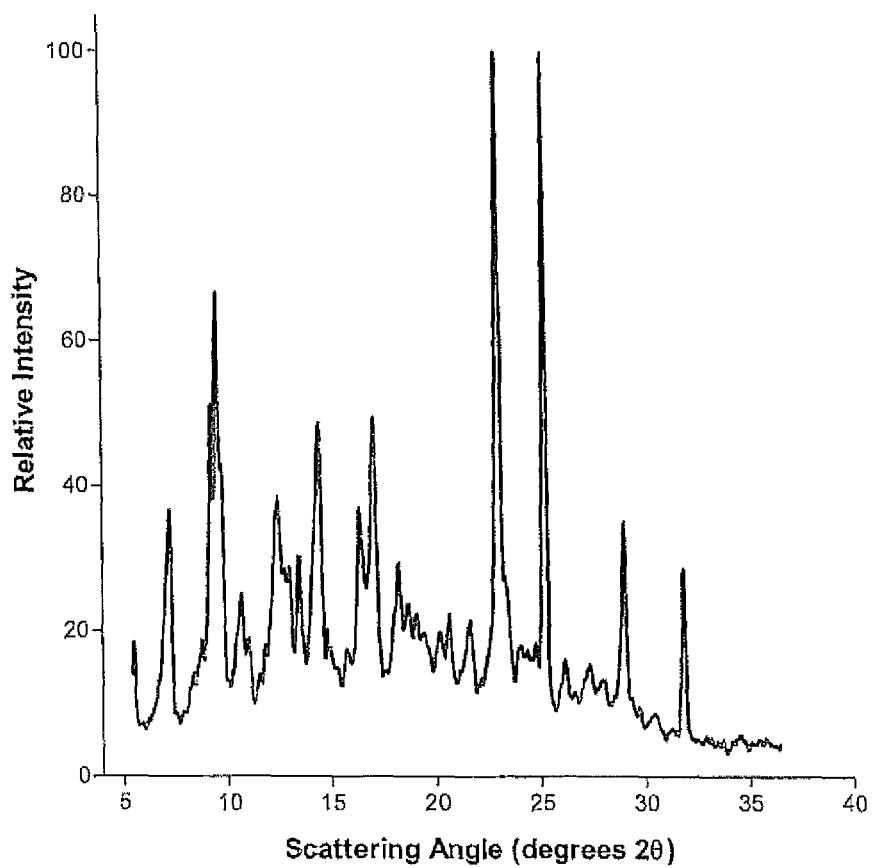
FIG. 9A is a graph depicting X-ray Powder Diffraction (XRPD) patterns of crystalline naltrexone formed by slow cooling using ethyl acetate (Lewis basic).
Figure 9B:
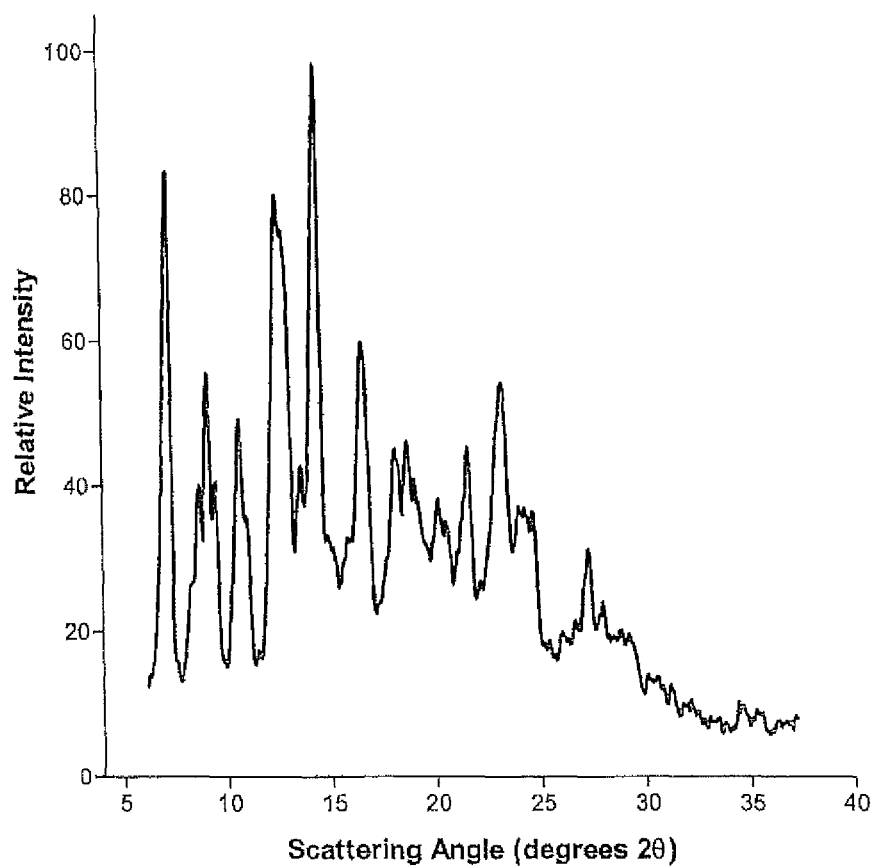
FIG. 9B is a graph depicting X-ray Powder Diffraction (XRPD) patterns of crystalline naltrexone formed by fast cooling using ethyl acetate (Lewis basic).
Figure 10A:
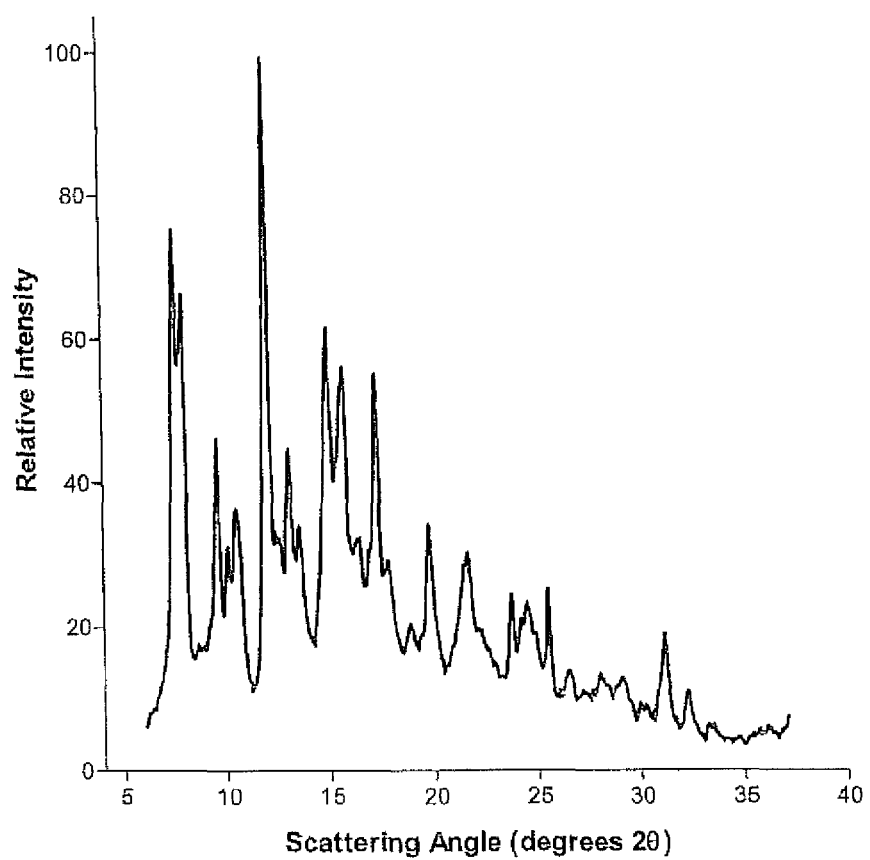
FIG. 10A is a graph depicting X-ray Powder Diffraction (XRPD) patterns of crystalline naltrexone formed by slow cooling using methyl ethyl ketone (Lewis basic).
Figure 10B:
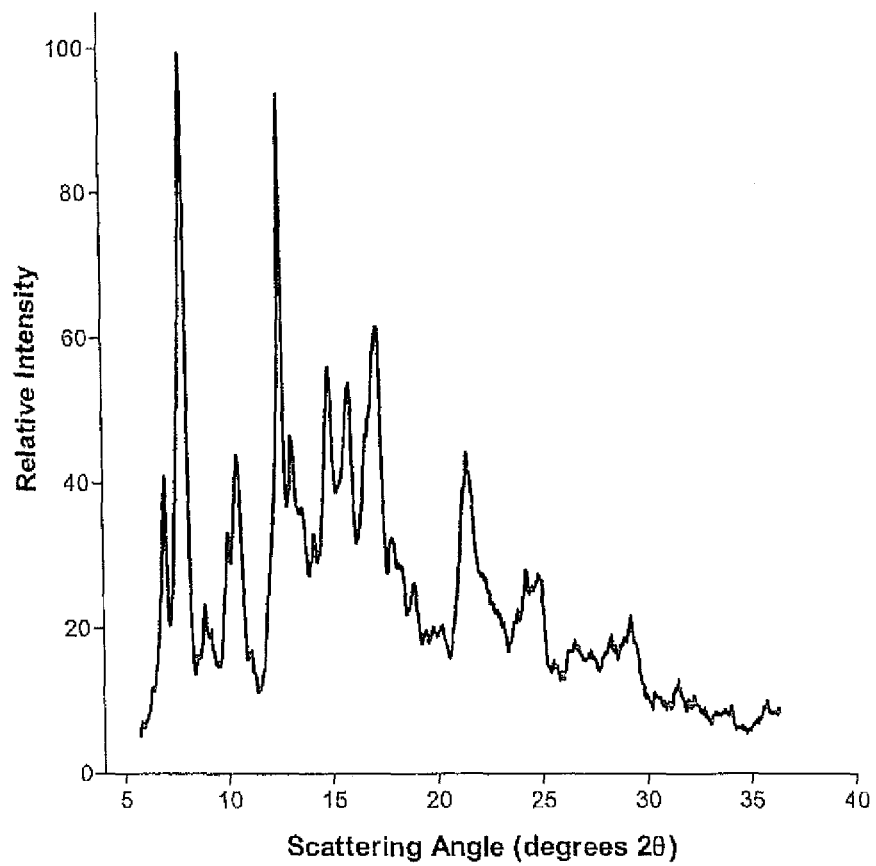
FIG. 10B is a graph depicting X-ray Powder Diffraction (XRPD) patterns of crystalline naltrexone formed by fast cooling using methyl ethyl ketone (Lewis basic).
Figure 11A:
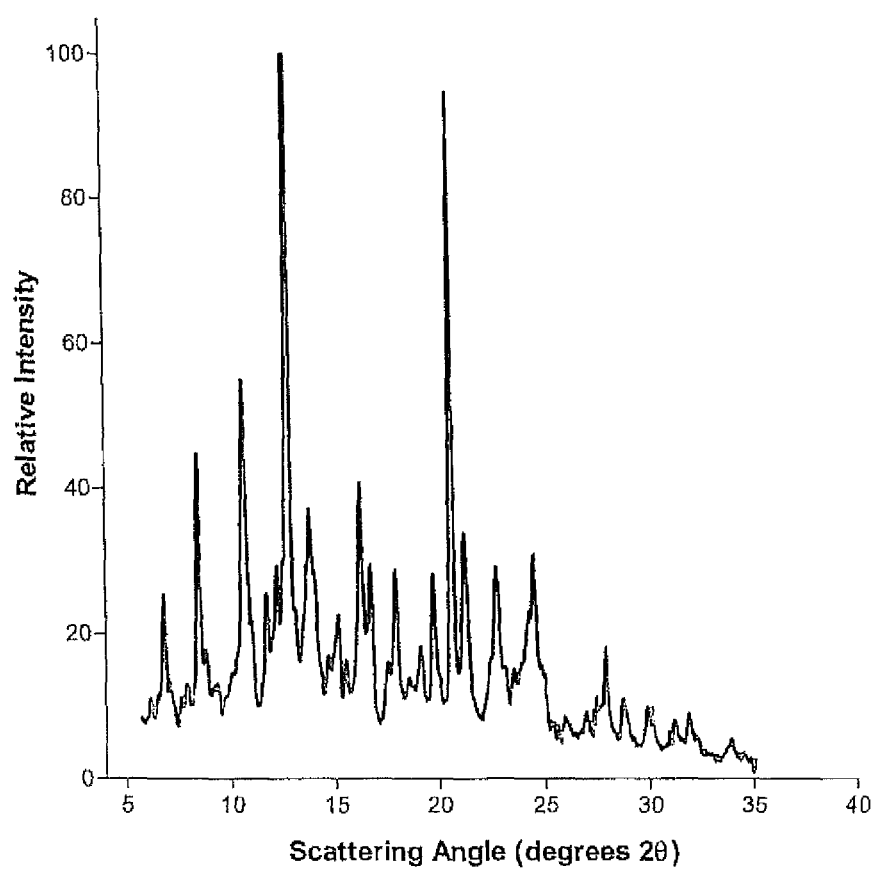
FIG. 11A is a graph depicting X-ray Powder Diffraction (XRPD) patterns of crystalline naltrexone formed by slow cooling using toluene (aromatic).
Figure 11B:
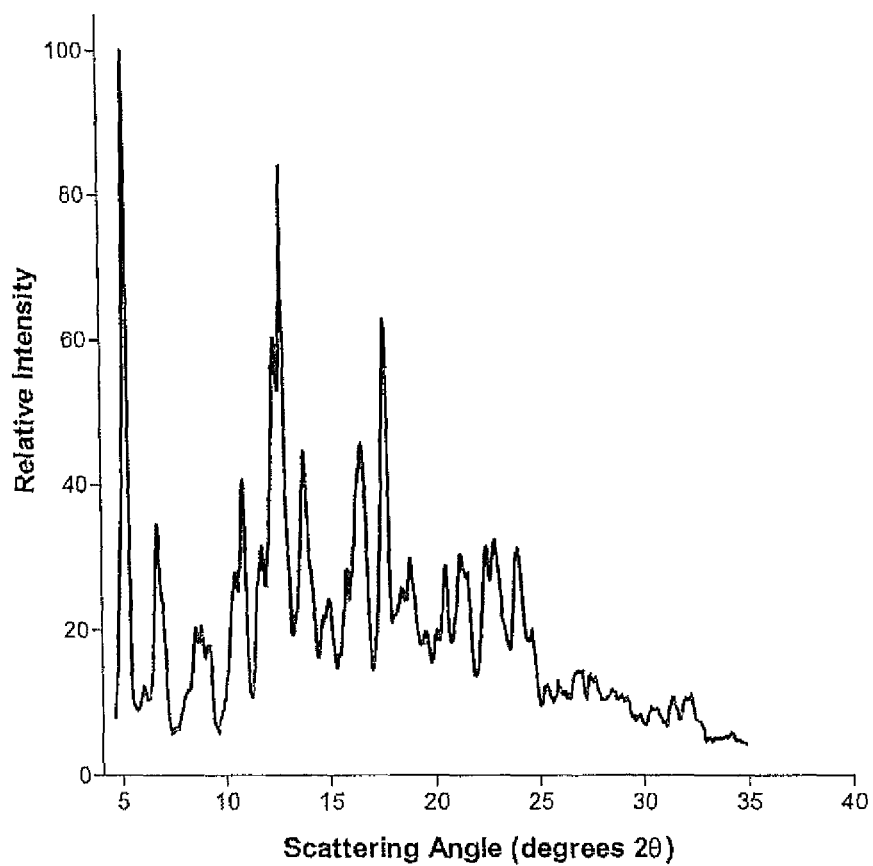
FIG. 11B is a graph depicting X-ray Powder Diffraction (XRPD) patterns of crystalline naltrexone formed by fast cooling using toluene (aromatic).
Figure 12A:
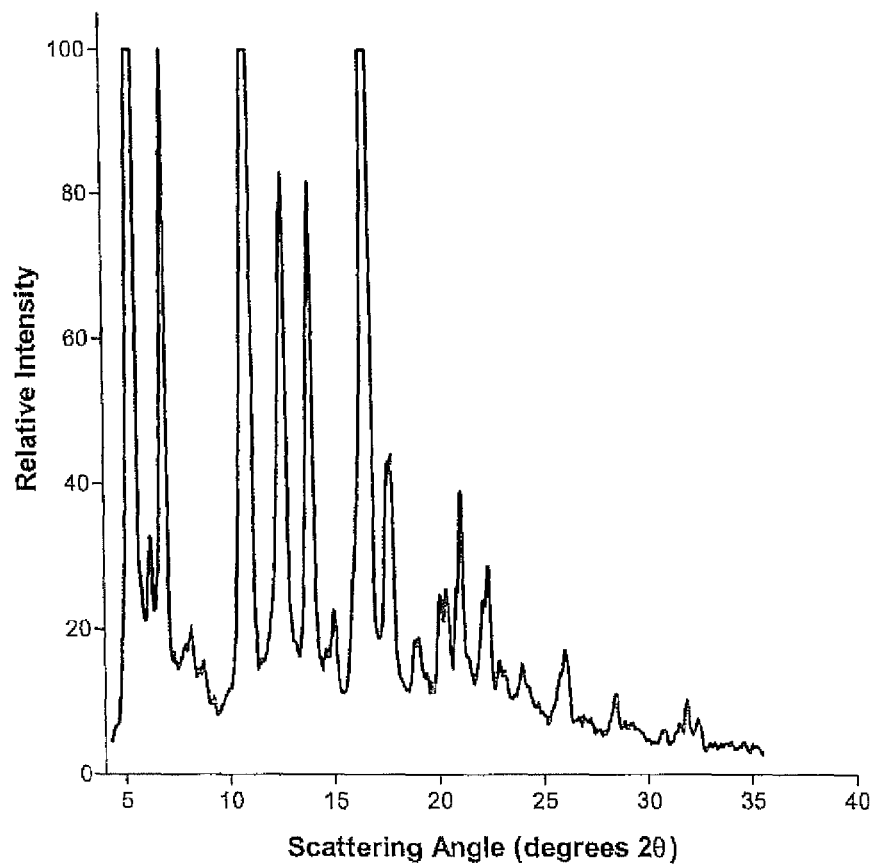
FIG. 12A is a graph depicting X-ray Powder Diffraction (XRPD) patterns of crystalline naltrexone formed by slow cooling using hexane (non-polar).
Figure 12B:
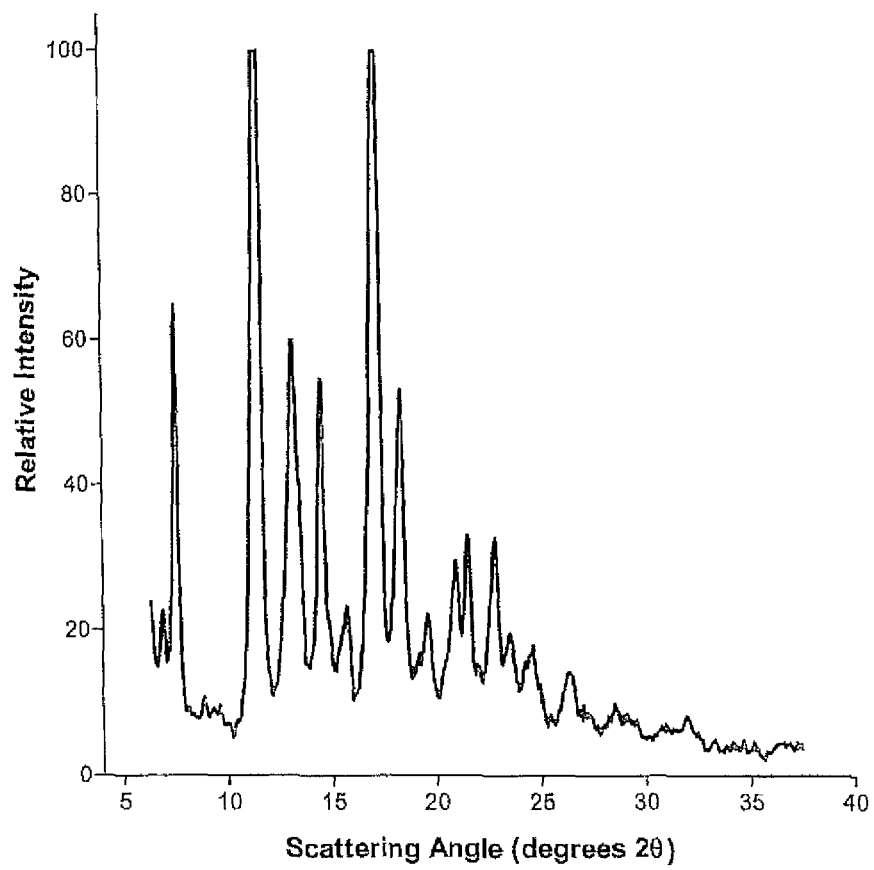
FIG. 12B is a graph depicting X-ray Powder Diffraction (XRPD) patterns of crystalline naltrexone formed by fast cooling using hexane (non-polar).
Figure 13A:
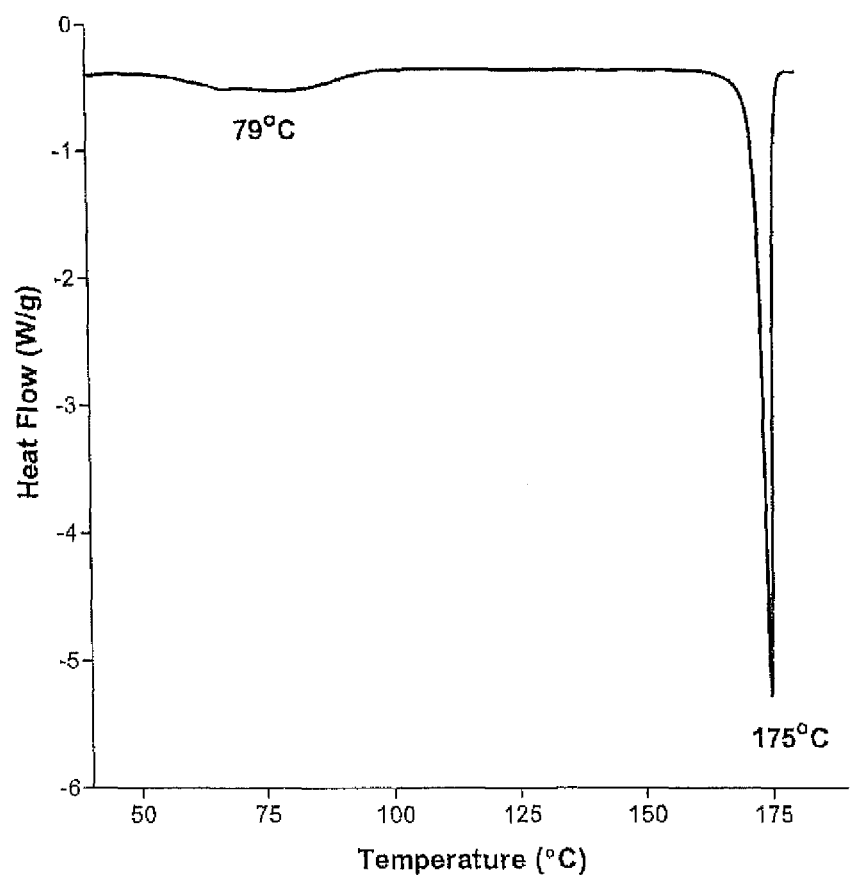
FIG. 13A is a graph depicting a DSC of crystalline naltrexone formed by slow cooling using acetonitrile (dipolar aprotic).
Figure 13B:
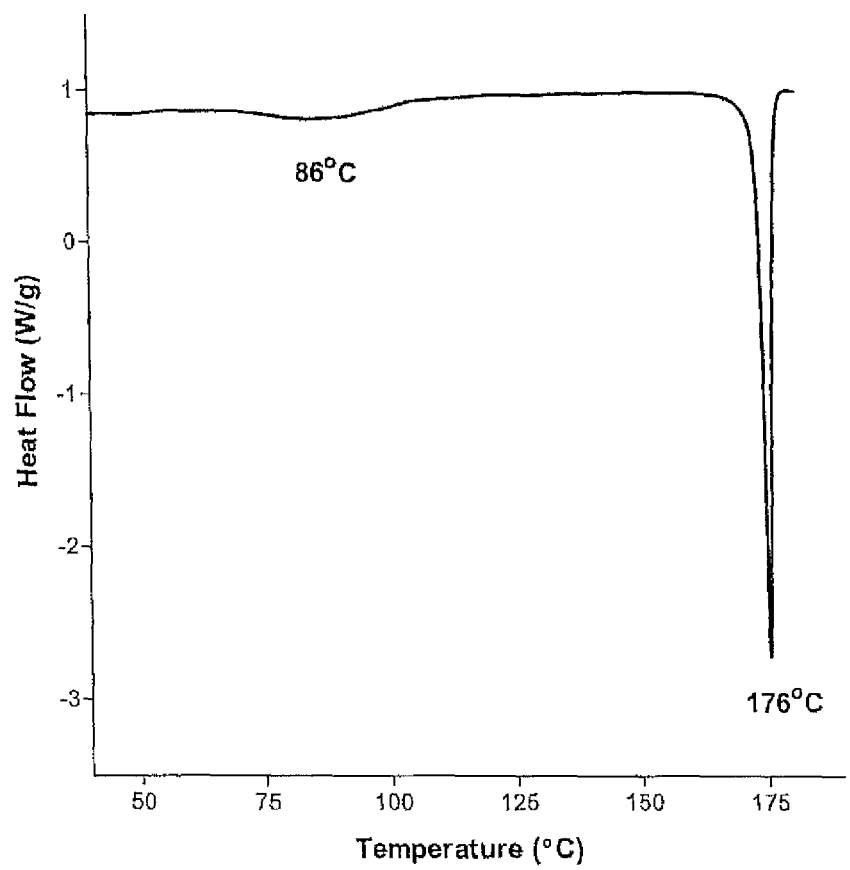
FIG. 13B is a graph depicting DSC of crystalline naltrexone formed by fast cooling using acetonitrile (dipolar aprotic).
Figure 14A:
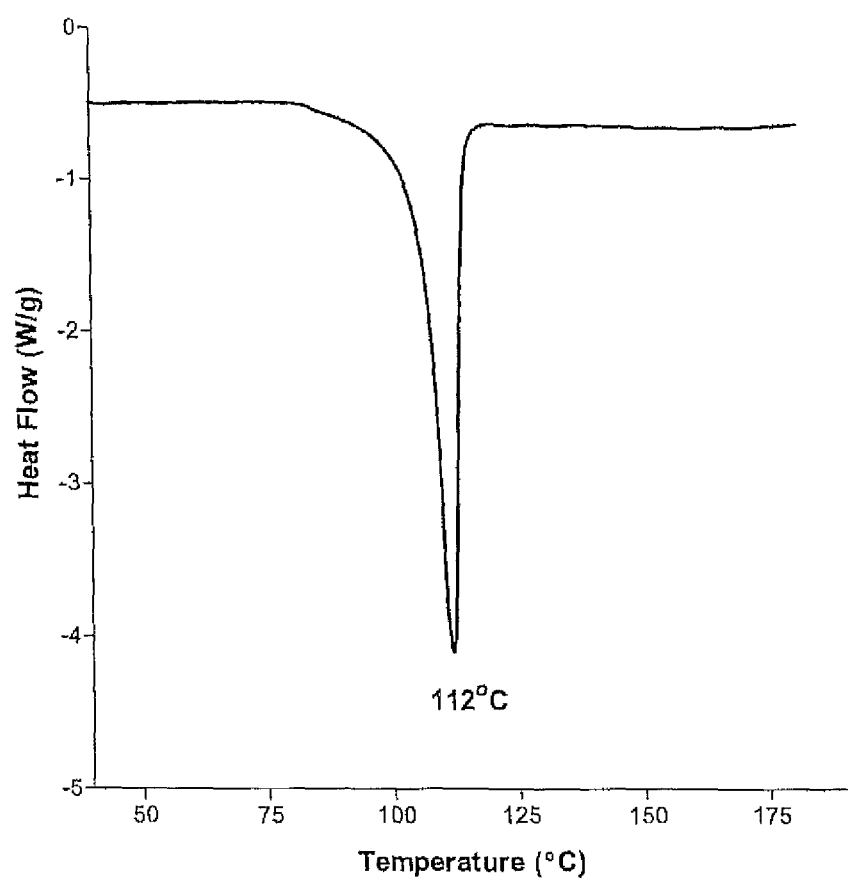
FIG. 14A is a graph depicting DSC of crystalline naltrexone formed by slow cooling using dimethyl formamide (dipolar aprotic).
Figure 14B:
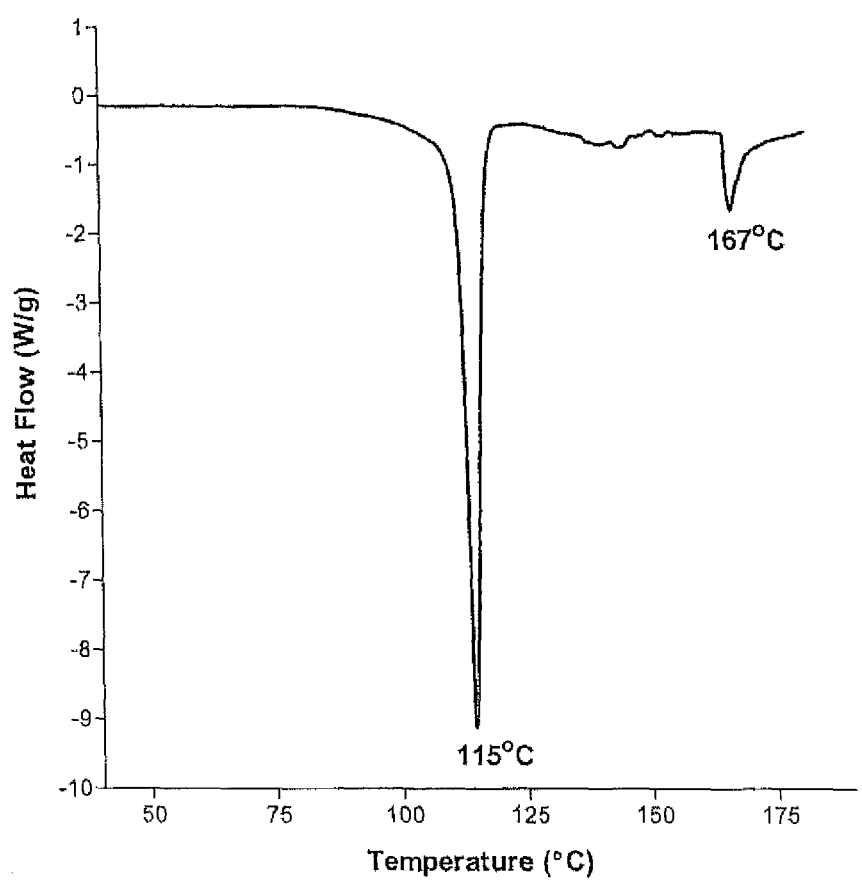
FIG. 14B is a graph depicting DSC of crystalline naltrexone formed by fast cooling using dimethyl formamide (dipolar aprotic).
Figure 15:
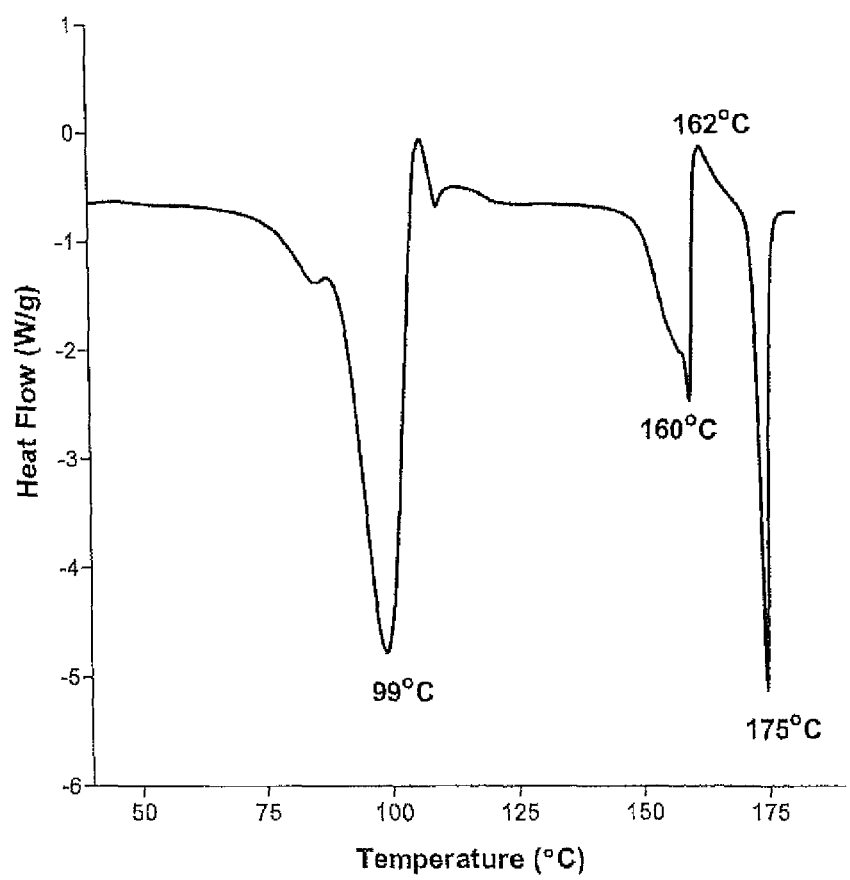
FIG. 15 is a graph depicting DSC of crystalline naltrexone formed by fast cooling using water (protic).
Figure 16A:
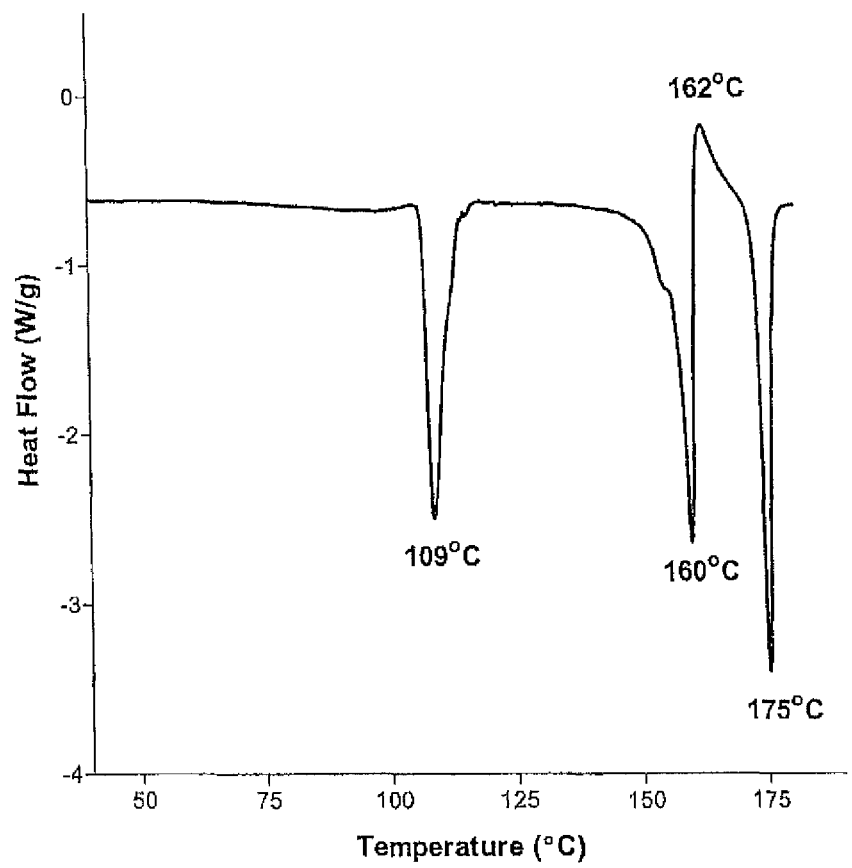
FIG. 16A is a graph depicting DSC of crystalline naltrexone formed by slow cooling using methanol (protic).
Figure 16B:
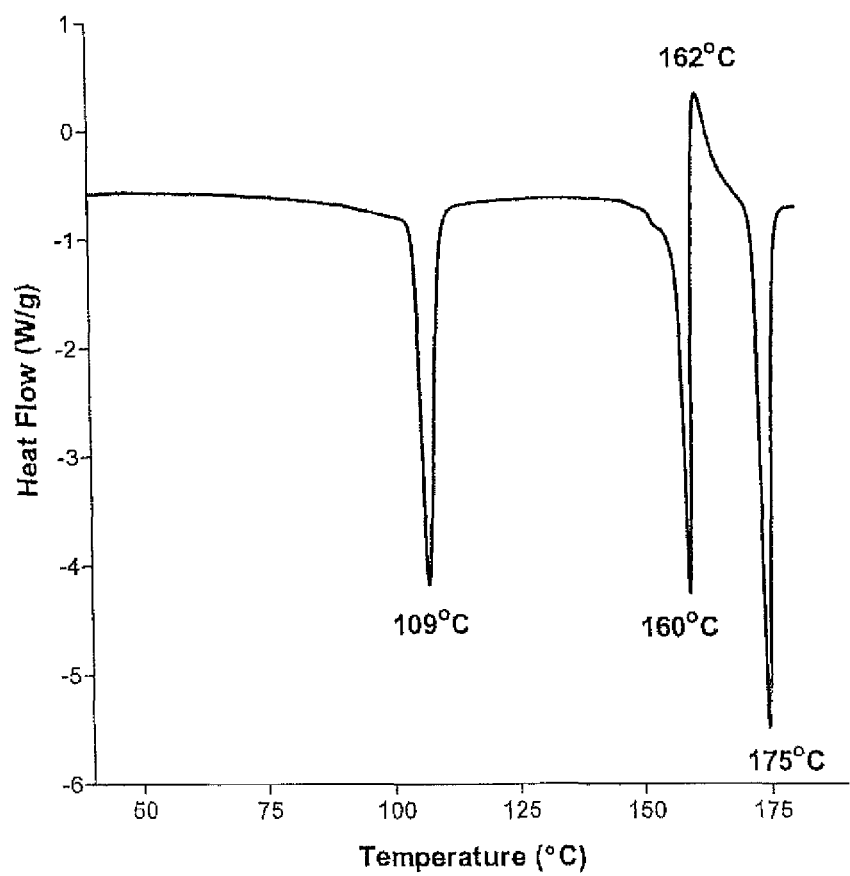
FIG. 16B is a graph depicting DSC of crystalline naltrexone formed by fast cooling using methanol (protic).
Figure 17A:
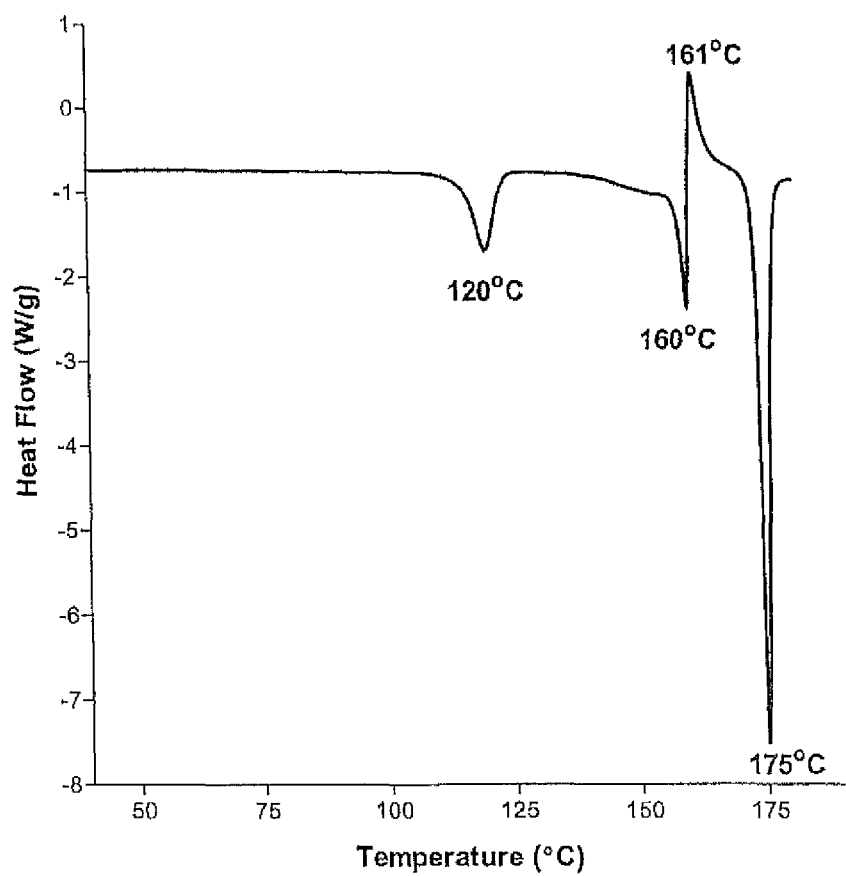
FIG. 17A is a graph depicting DSC of crystalline naltrexone formed by slow cooling using ethanol (protic).
Figure 17B:
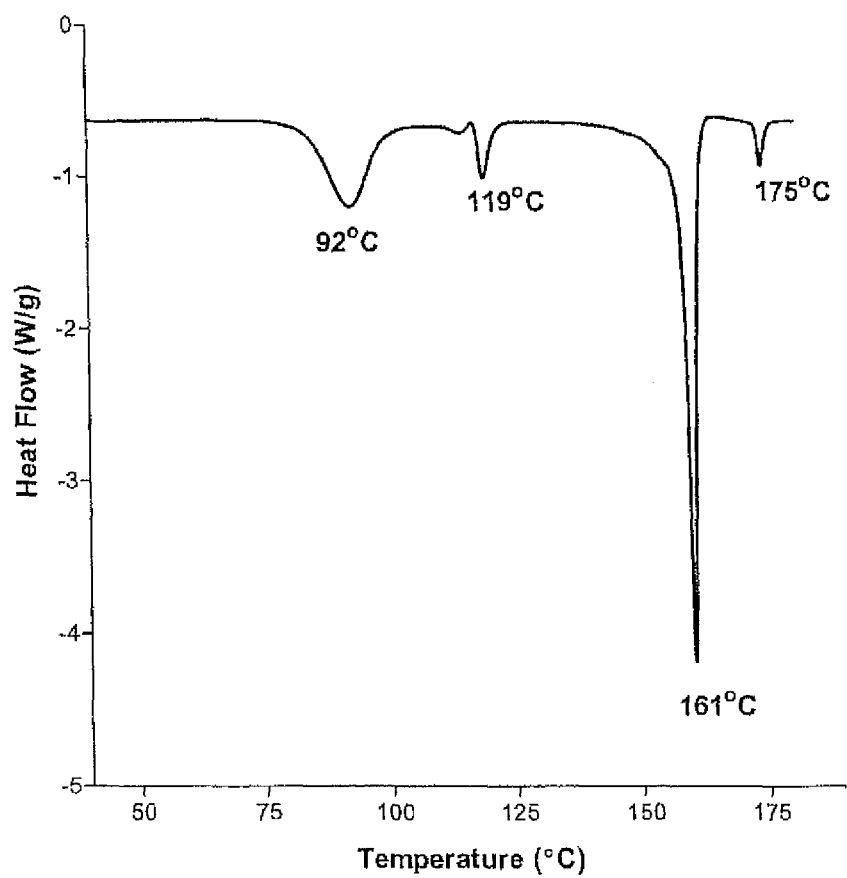
FIG. 17B is a graph depicting DSC of crystalline naltrexone formed by fast cooling using ethanol (protic).
Figure 18:
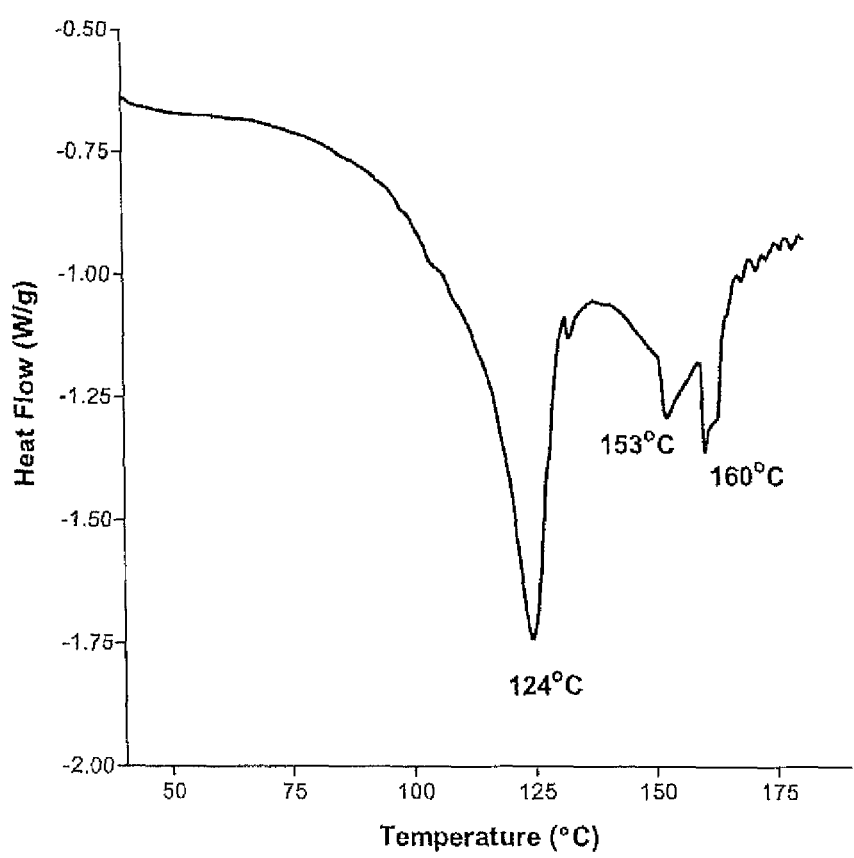
FIG. 18 is a graph depicting DSC of crystalline naltrexone formed by fast cooling using benzyl alcohol (protic).
Figure 19A:
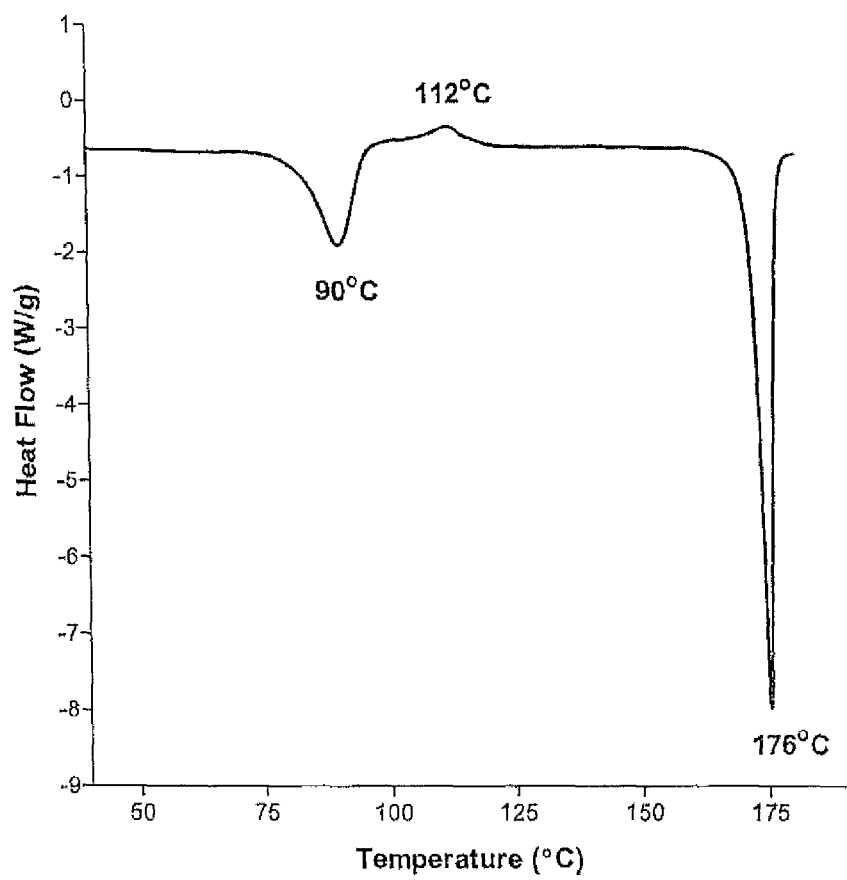
FIG. 19A is a graph depicting DSC of crystalline naltrexone formed by slow cooling using dichloromethane (Lewis acidic).
Figure 19B:
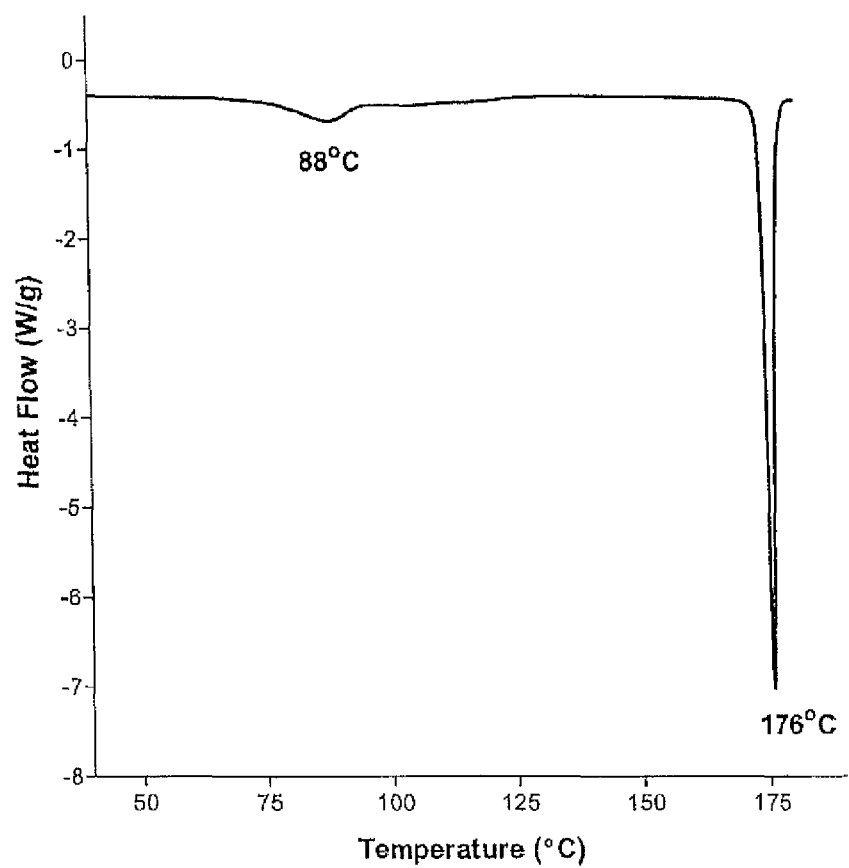
FIG. 19B is a graph depicting DSC of crystalline naltrexone formed by fast cooling using dichloromethane (Lewis acidic).
Figure 20A:
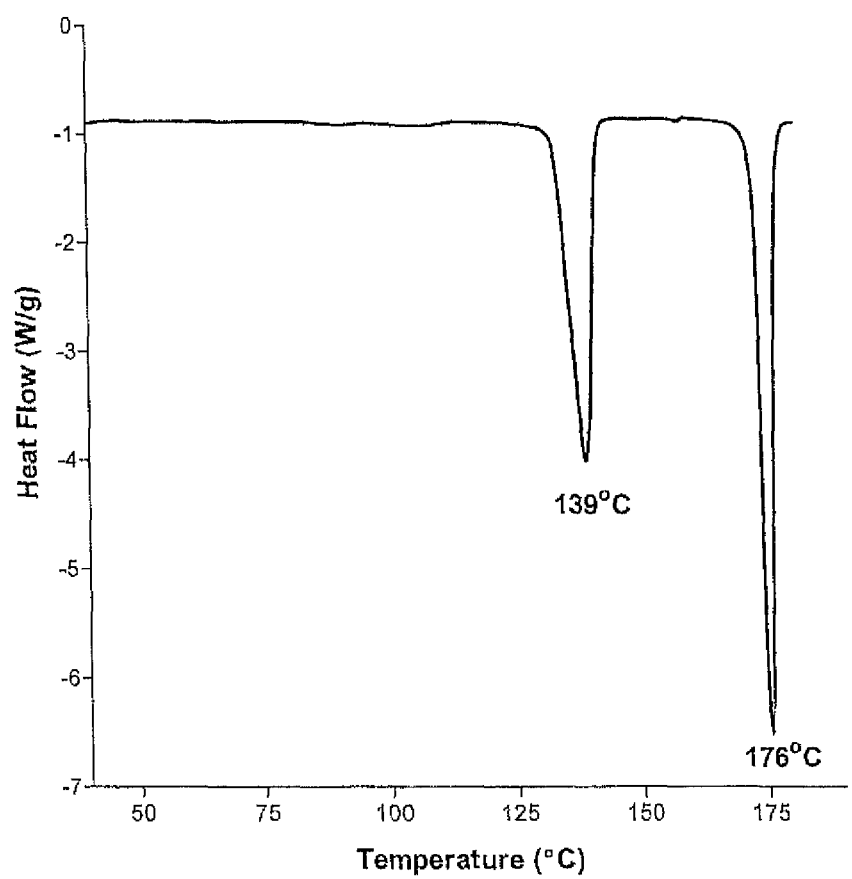
FIG. 20A is a graph depicting DSC of crystalline naltrexone formed by slow cooling using acetone (Lewis basic).
Figure 20B:
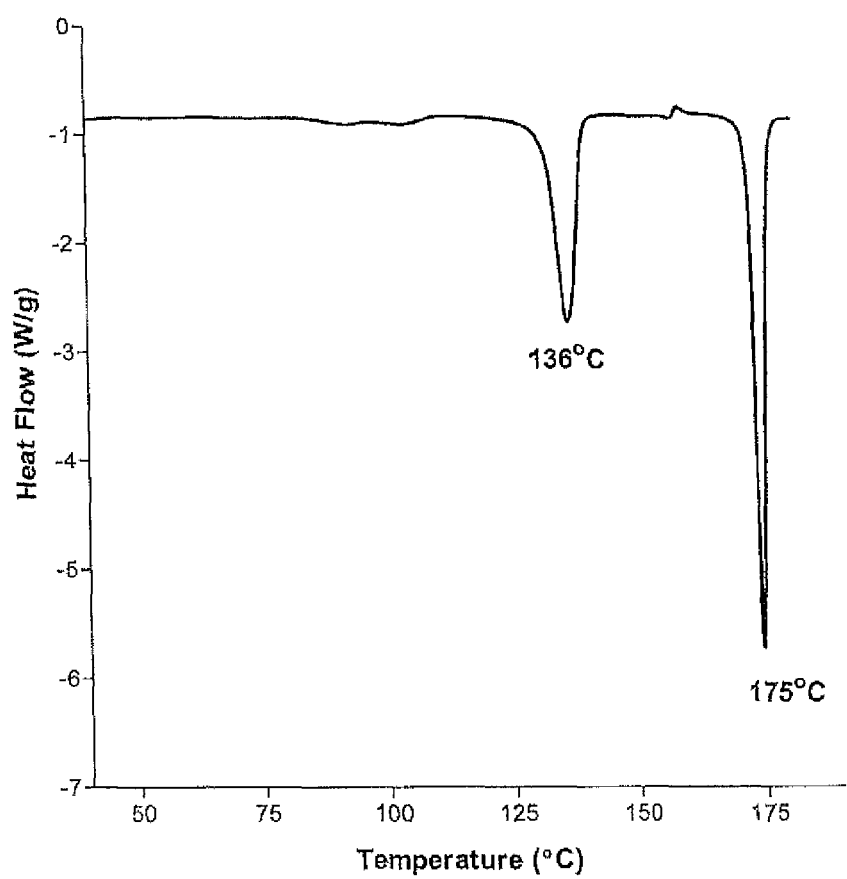
FIG. 20B is a graph depicting DSC of crystalline naltrexone formed by fast cooling using acetone (Lewis basic).
Figure 21A:
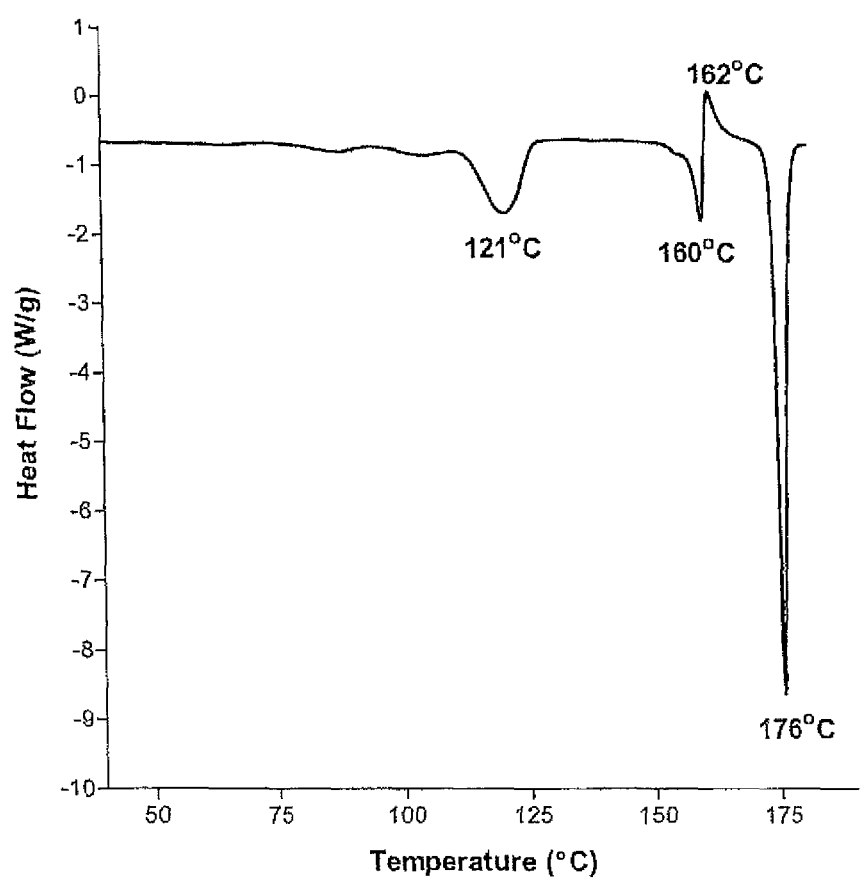
FIG. 21A is a graph depicting DSC of crystalline naltrexone formed by slow cooling using ethyl acetate (Lewis basic).
Figure 21B:
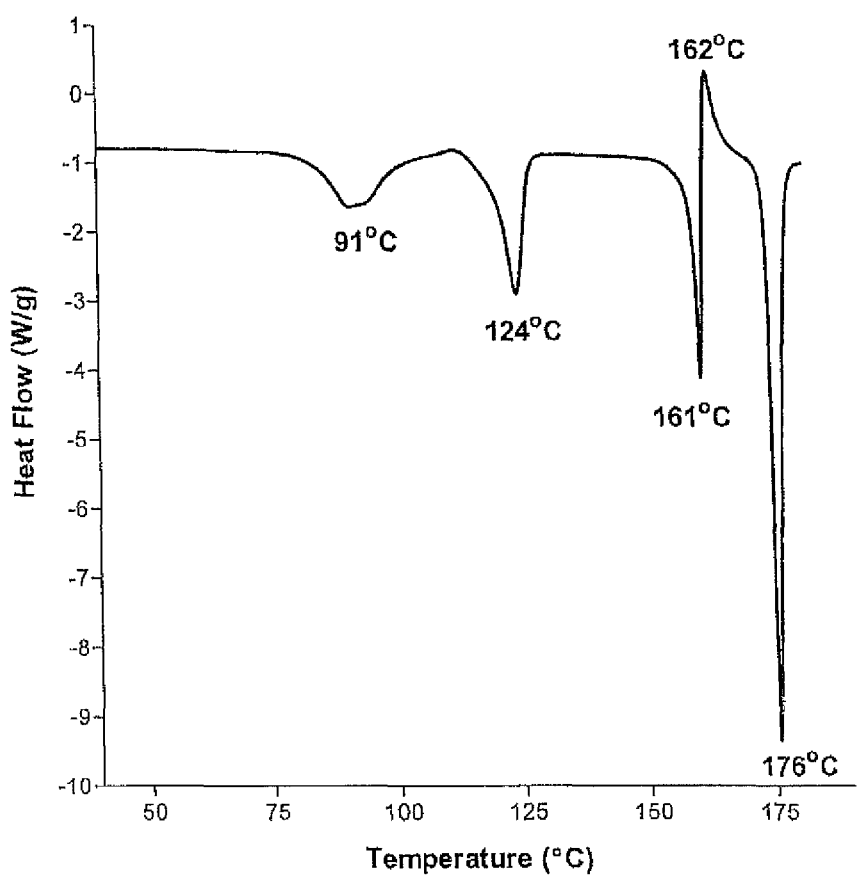
FIG. 21B is a graph depicting DSC of crystalline naltrexone formed by fast cooling using ethyl acetate (Lewis basic).
Figure 22A:
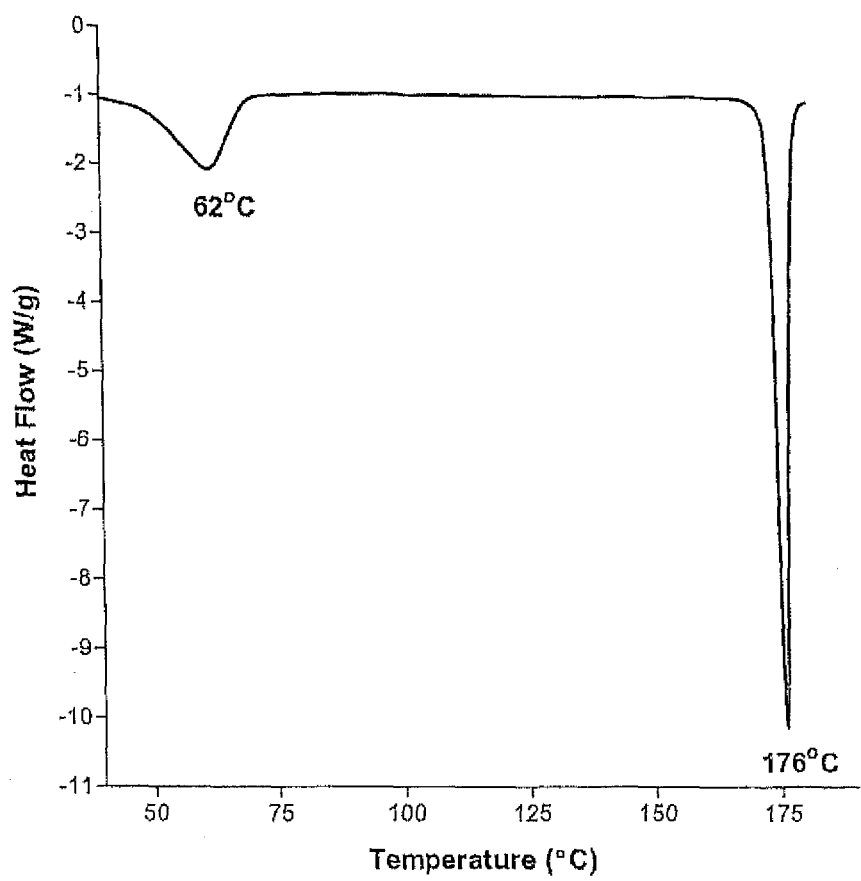
FIG. 22A is a graph depicting DSC of crystalline naltrexone formed by slow cooling using methyl ethyl ketone (Lewis basic).
Figure 22B:
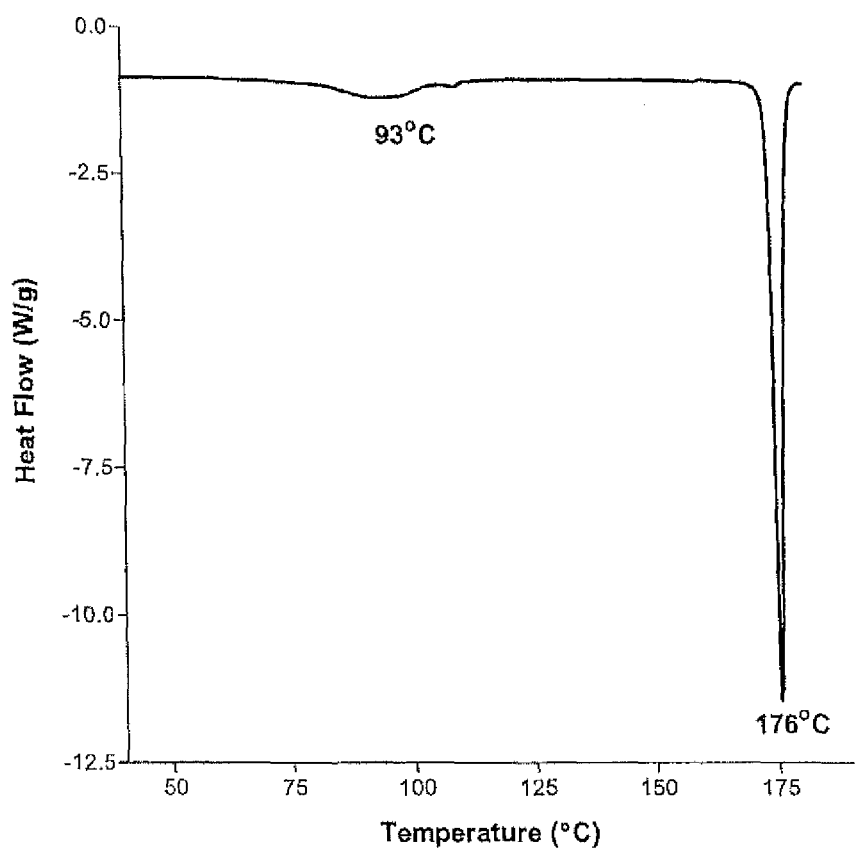
FIG. 22B is a graph depicting DSC of crystalline naltrexone formed by fast cooling using methyl ethyl ketone (Lewis basic).
Figure 23A:
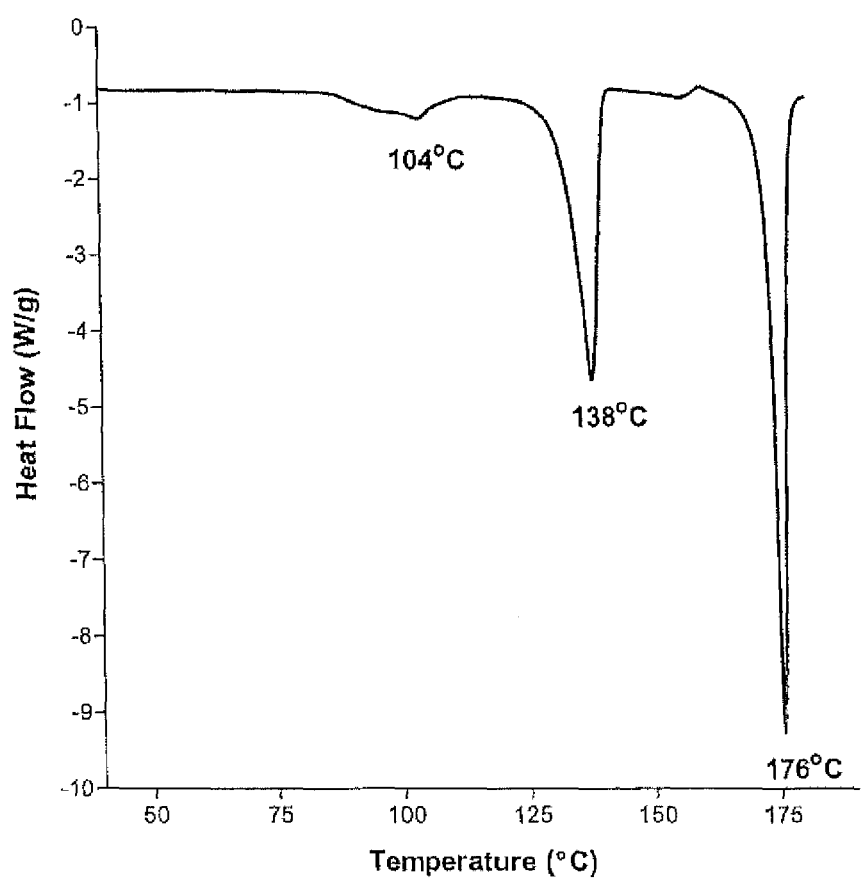
FIG. 23A is a graph depicting DSC of crystalline naltrexone formed by slow cooling using toluene (aromatic).
Figure 23B:
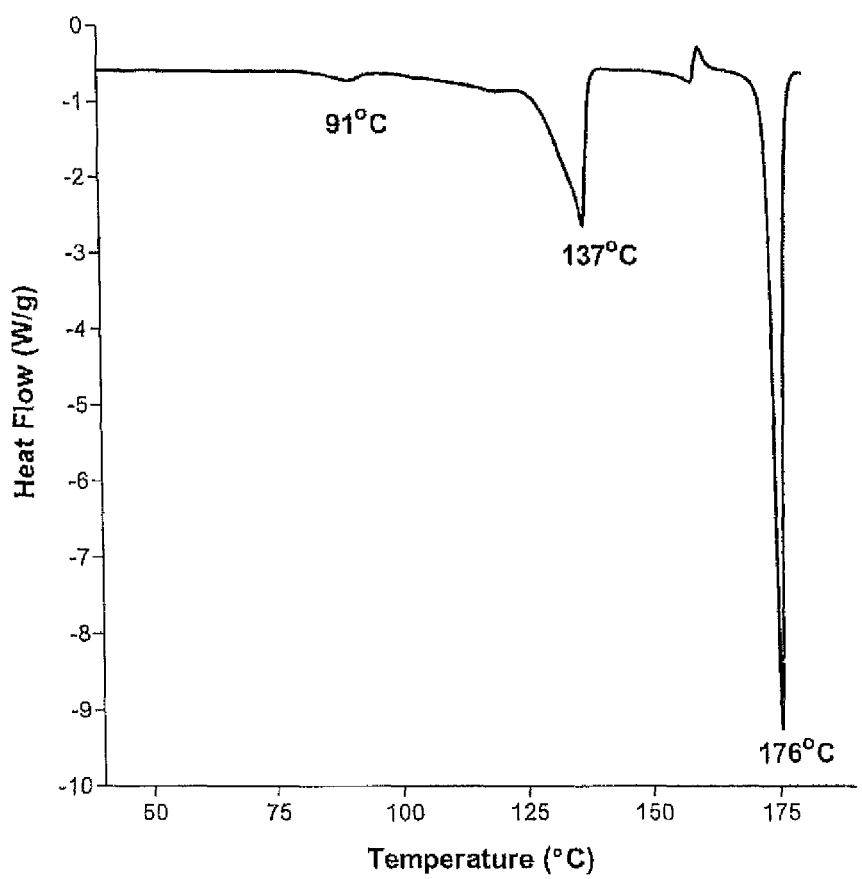
FIG. 23B is a graph depicting DSC of crystalline naltrexone formed by fast cooling using toluene (aromatic).
Figure 24A:
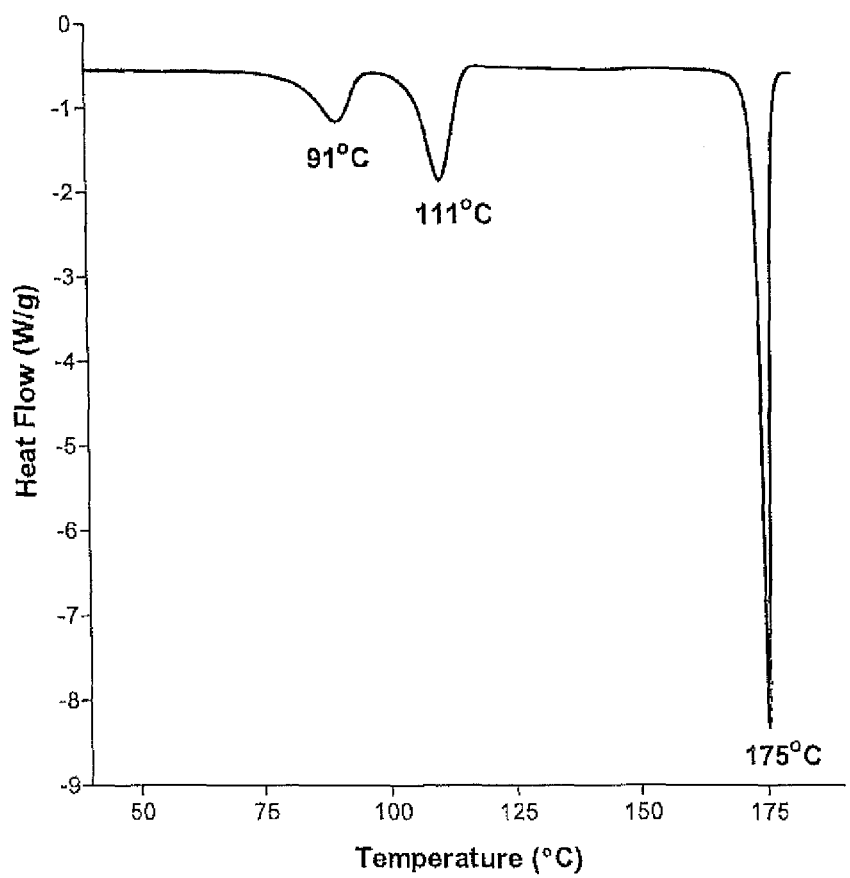
FIG. 24A is a graph depicting DSC of crystalline naltrexone formed by slow cooling using hexane (non-polar).
Figure 24B:
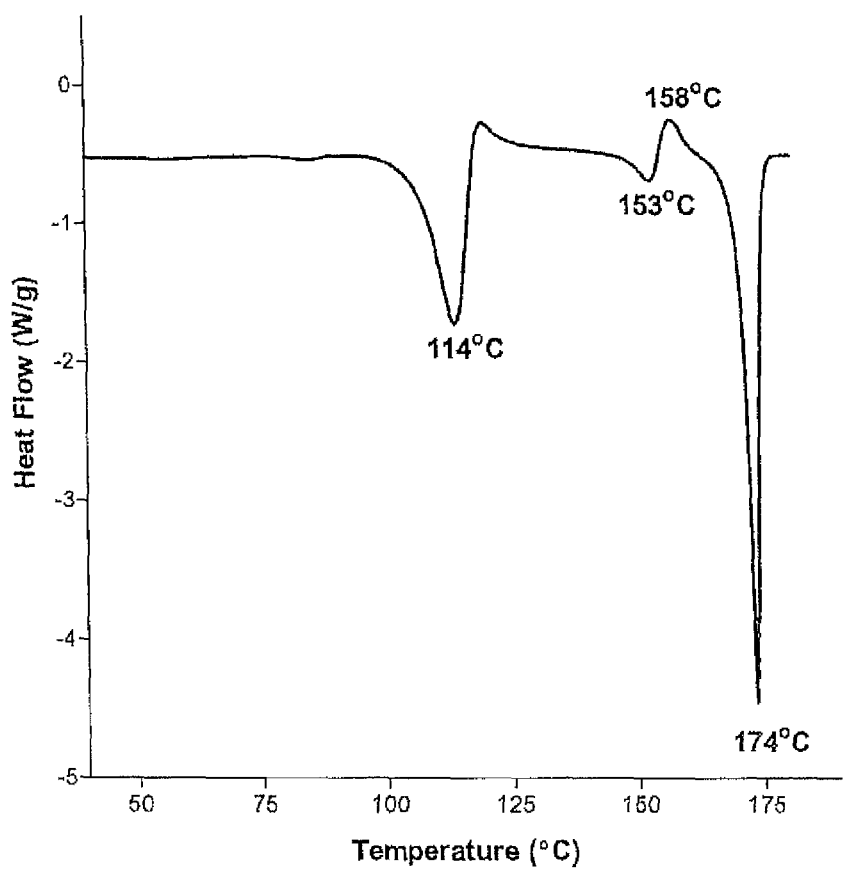
FIG. 24B is a graph depicting DSC of crystalline naltrexone formed by fast cooling using hexane (non-polar).
Figure 25A:
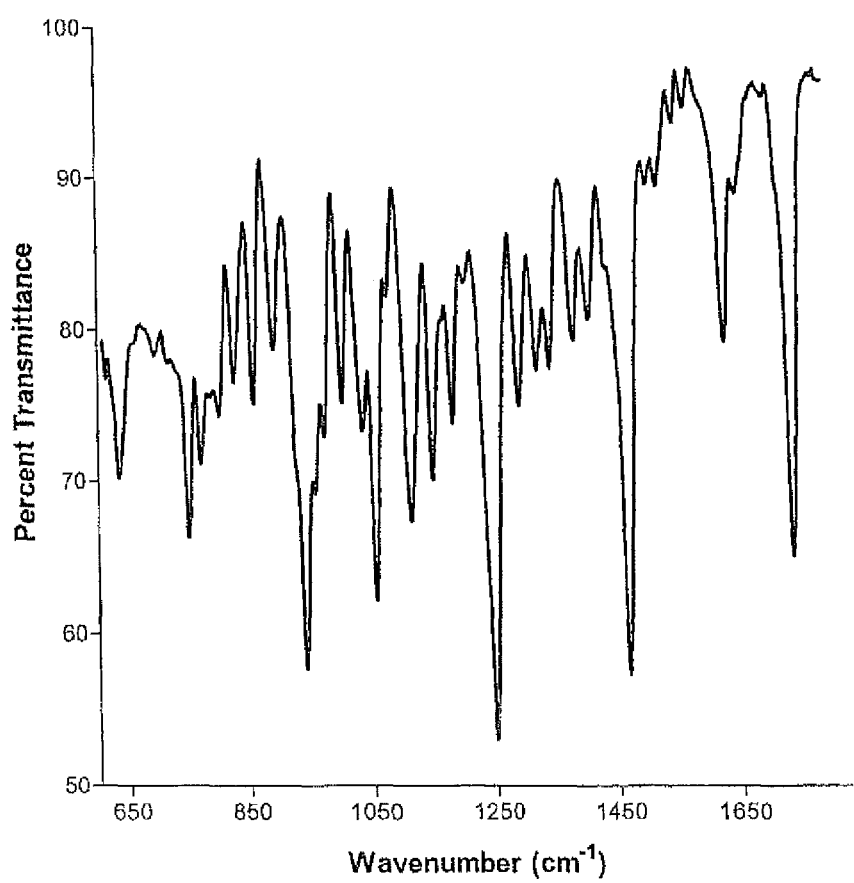
FIG. 25A is a graph depicting IR-ATR of crystalline naltrexone formed by slow cooling using acetonitrile (dipolar aprotic).
Figure 25B:
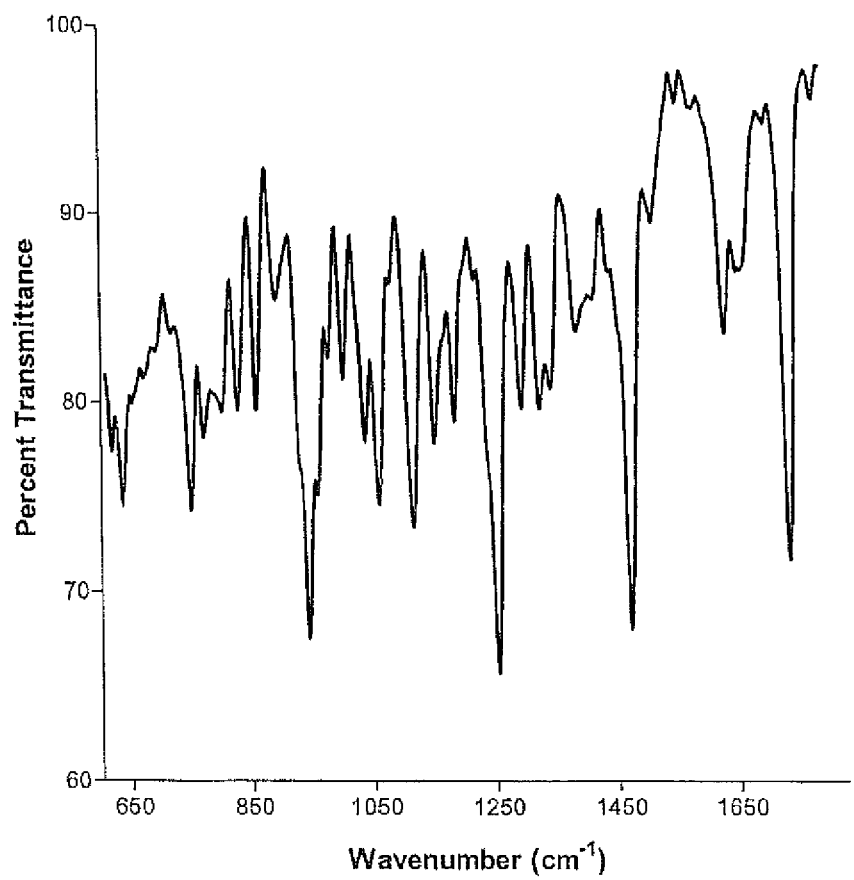
FIG. 25B is a graph depicting IR-ATR of crystalline naltrexone formed by fast cooling using acetonitrile (dipolar aprotic).
Figure 26A:
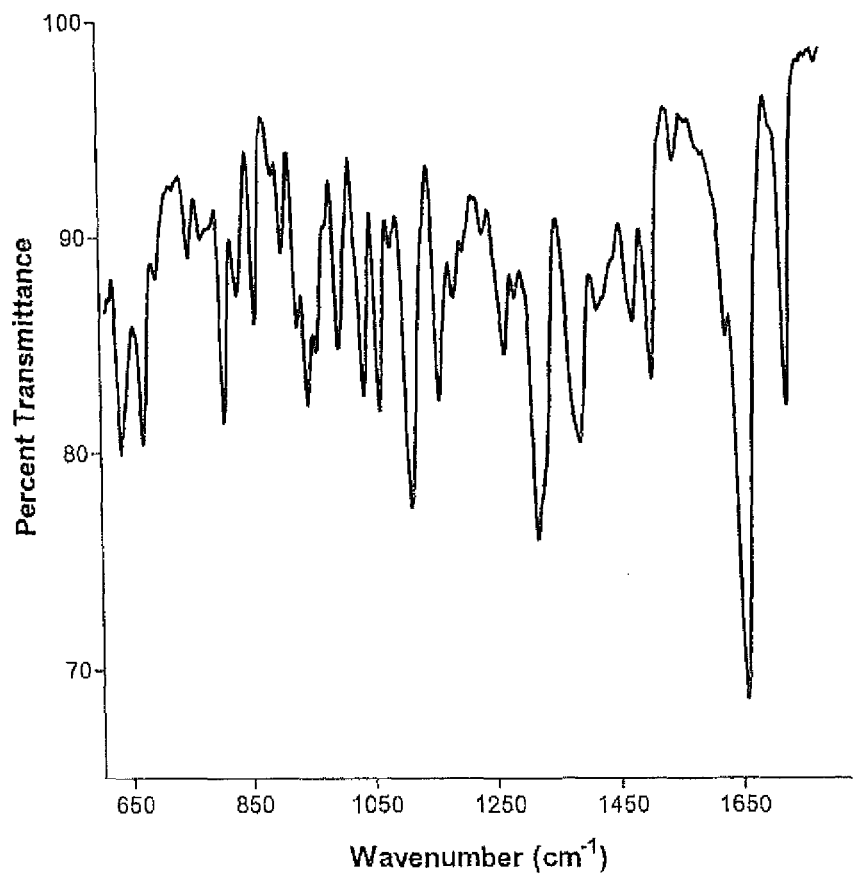
FIG. 26A is a graph depicting IR-ATR of crystalline naltrexone formed by slow cooling using dimethyl formamide (dipolar aprotic).
Figure 26B:
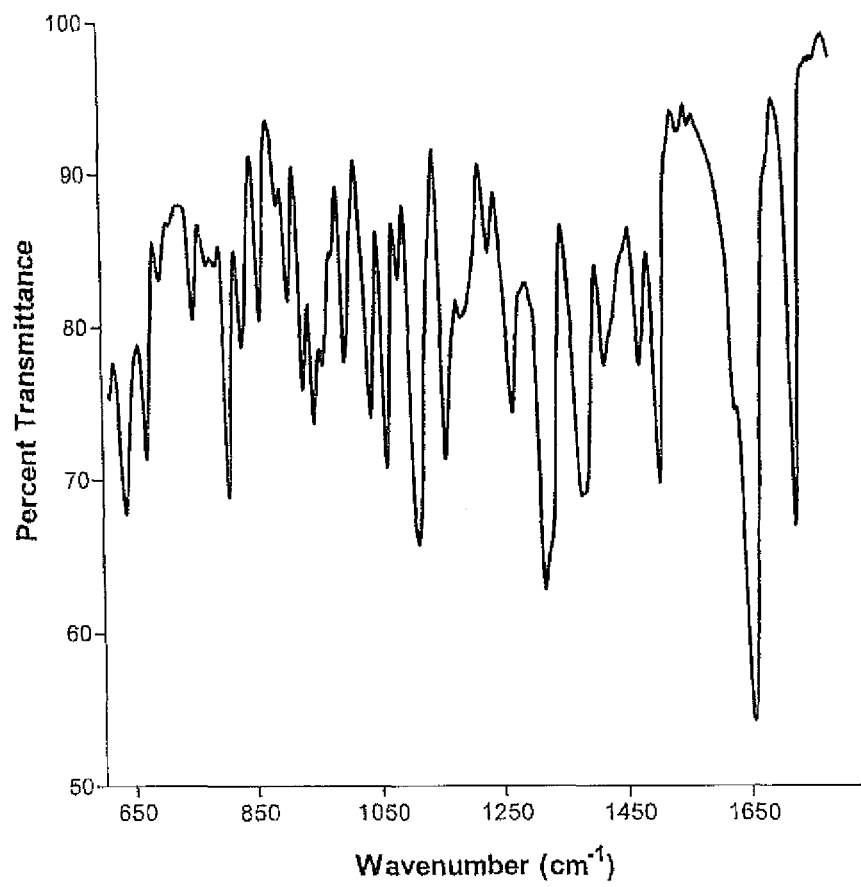
FIG. 26B is a graph depicting IR-ATR of crystalline naltrexone formed by fast cooling using dimethyl formamide (dipolar aprotic).
Figure 27:
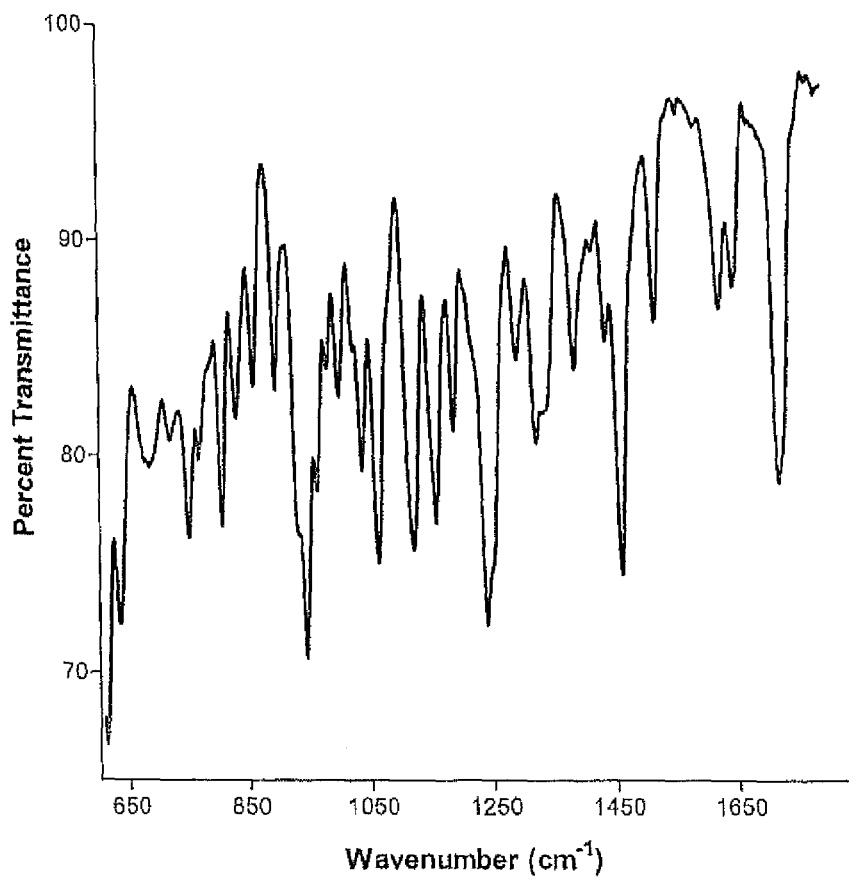
FIG. 27 is a graph depicting IR-ATR of crystalline naltrexone formed by fast cooling using water (protic).
Figure 28A:
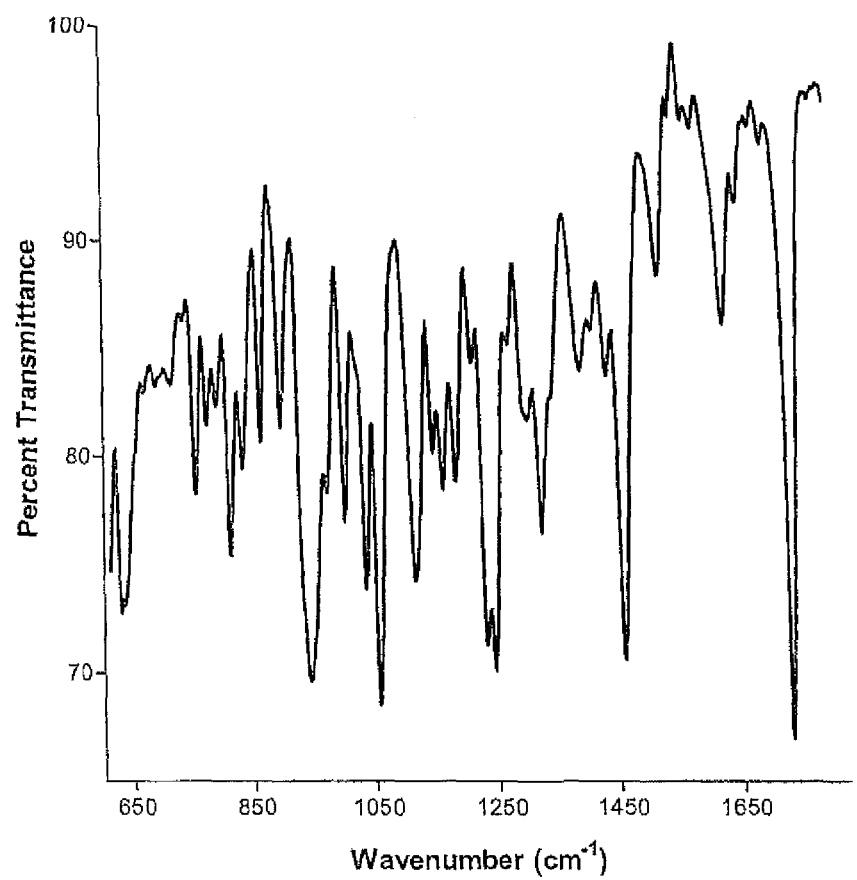
FIG. 28A is an IR-ATR of crystalline naltrexone formed by slow cooling using methanol (protic).
Figure 28B:
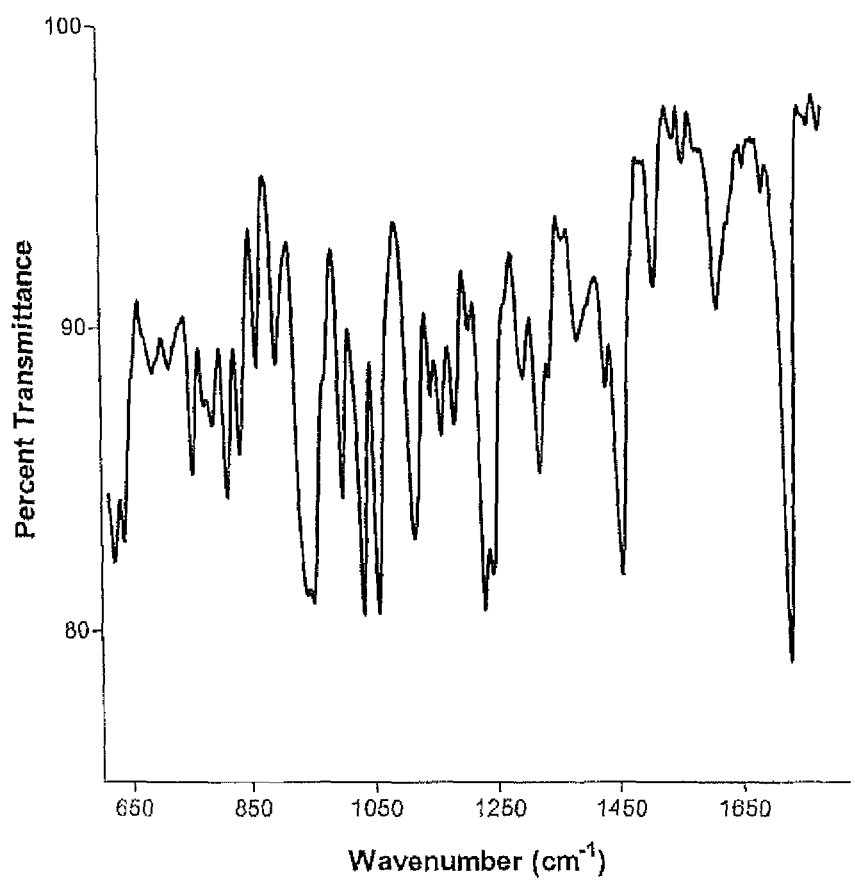
FIG. 28B is an IR-ATR of crystalline naltrexone formed by fast cooling using methanol (protic).
Figure 29A:
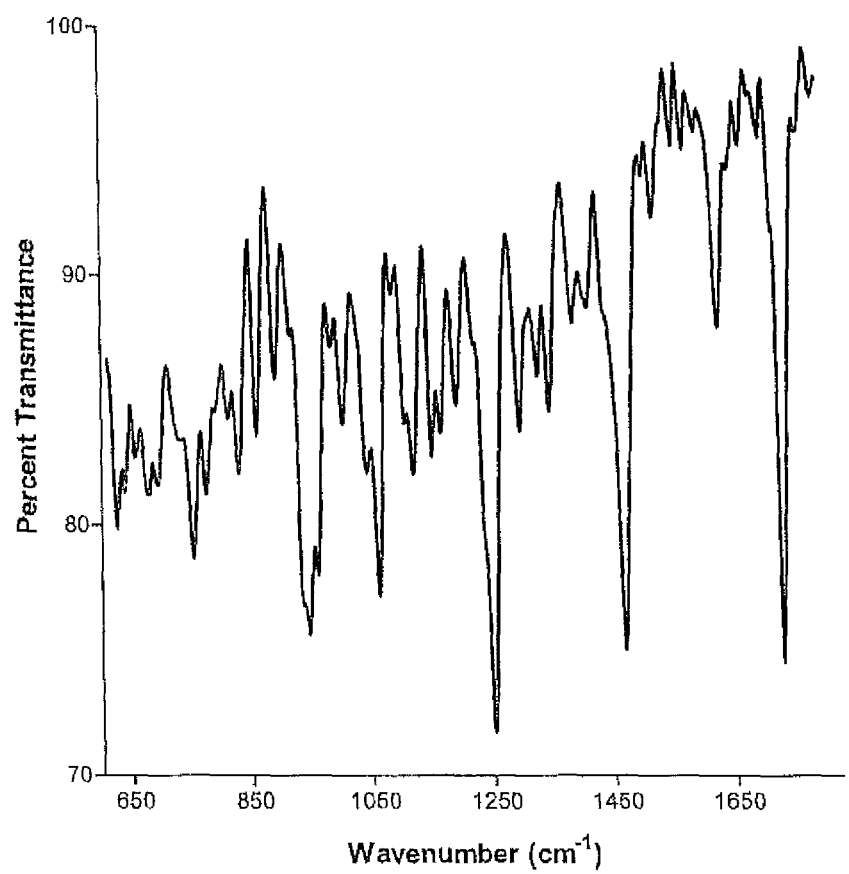
FIG. 29A is an IR-ATR of crystalline naltrexone formed by slow cooling using ethanol (protic).
Figure 29B:
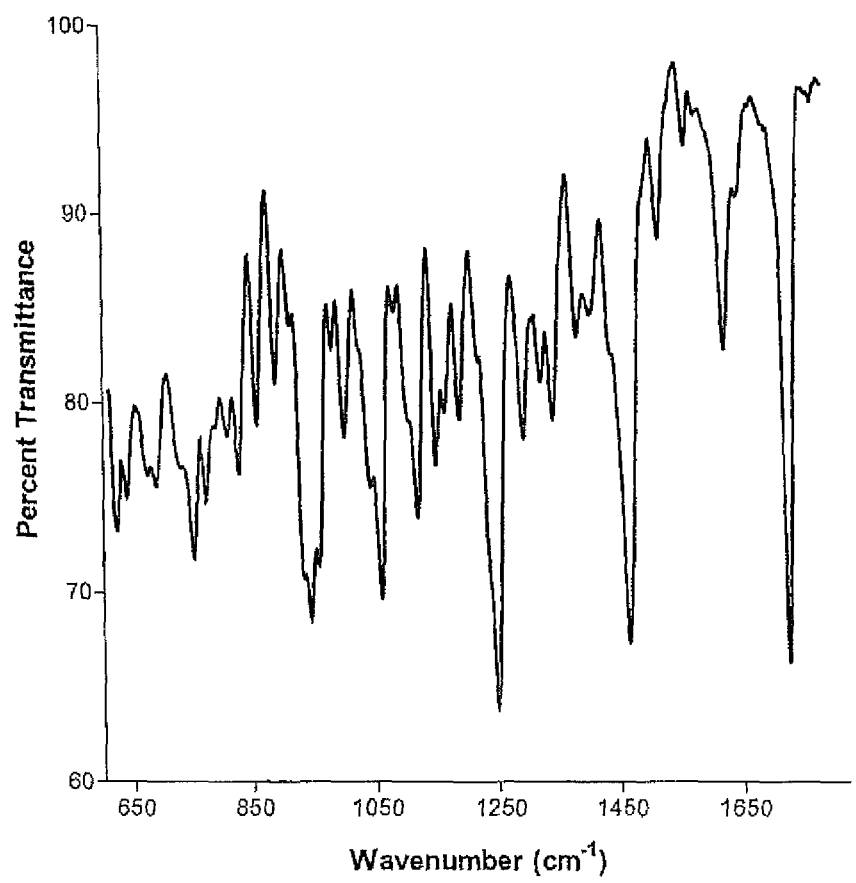
FIG. 29B is an IR-ATR of crystalline naltrexone formed by fast cooling using ethanol (protic).
Figure 30:
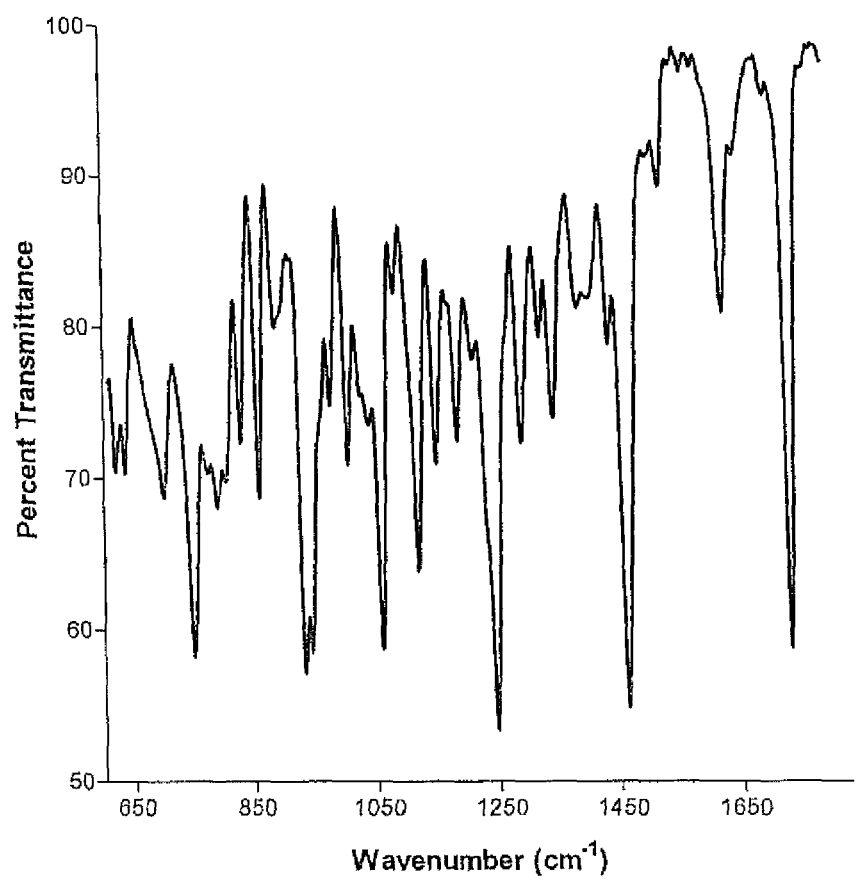
FIG. 30 is an IR-ATR of crystalline naltrexone formed by fast cooling using benzyl alcohol (protic).
Figure 31A:
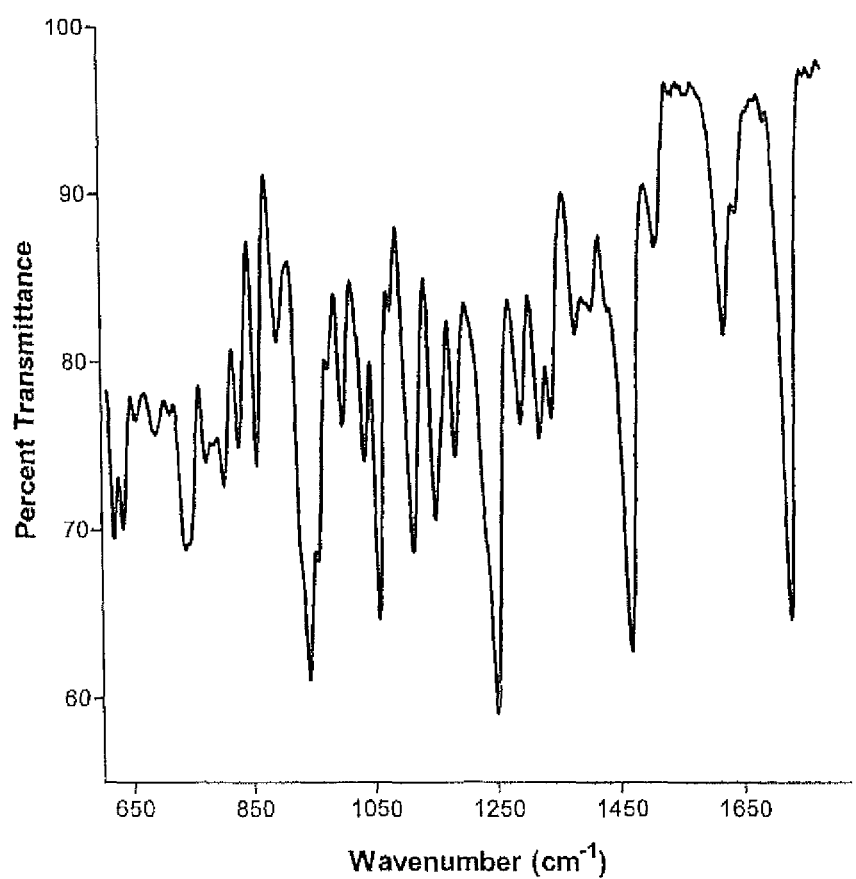
FIG. 31A is an IR-ATR of crystalline naltrexone formed by slow cooling using dichloromethane (Lewis acidic).
Figure 31B:
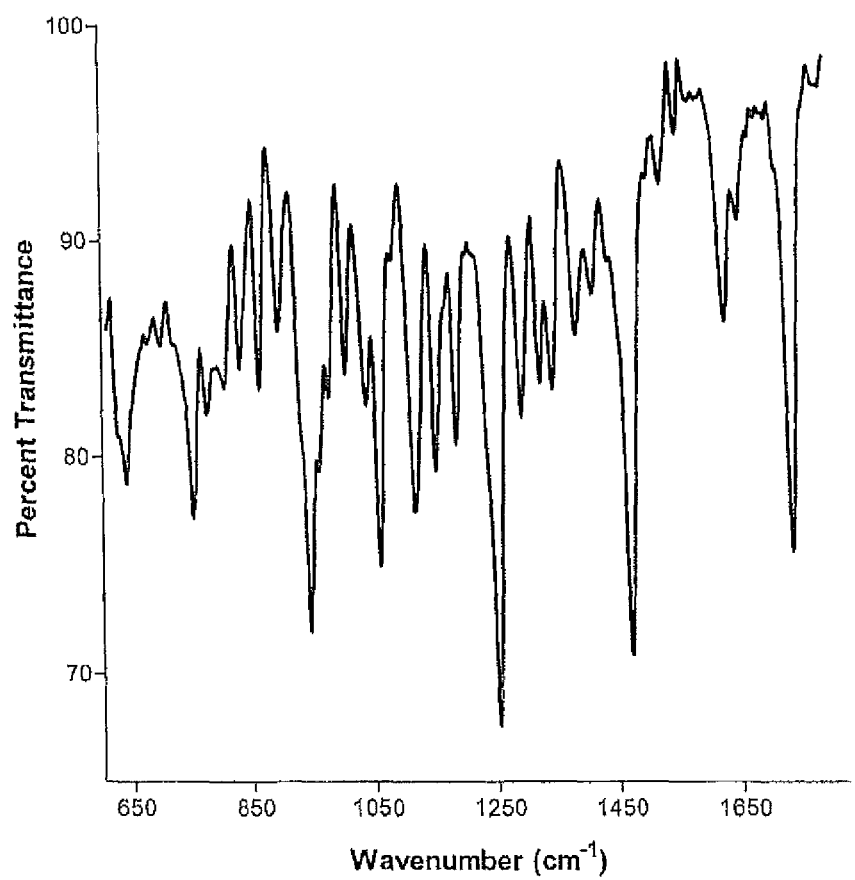
FIG. 31B is an IR-ATR of crystalline naltrexone formed by fast cooling using dichloromethane (Lewis acidic).
Figure 32A:
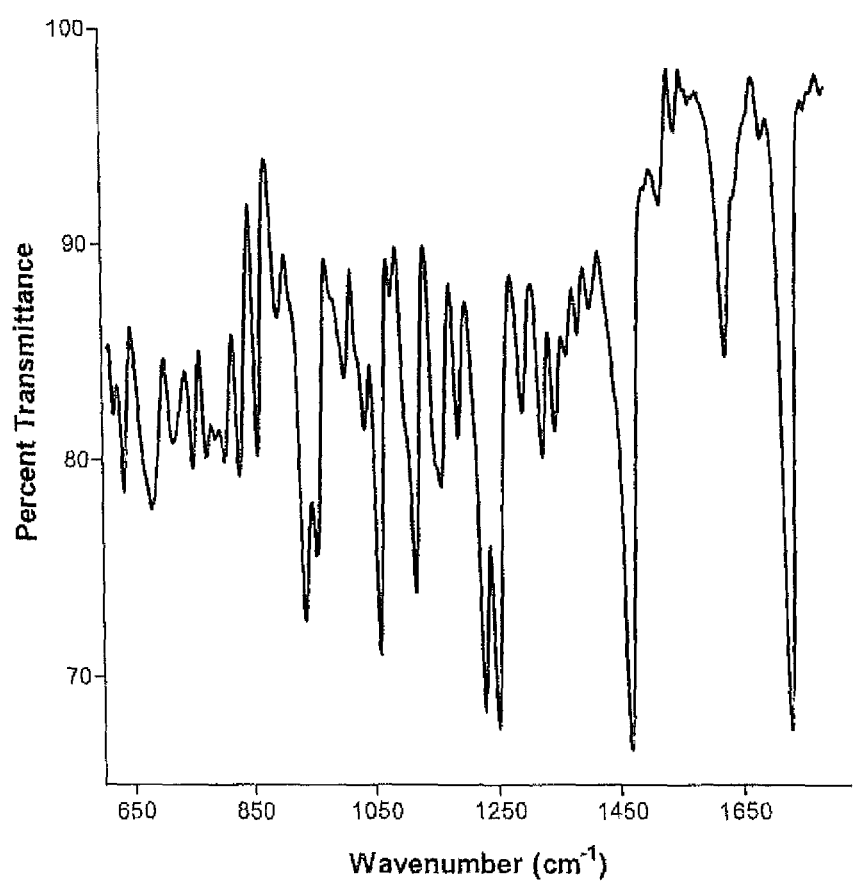
FIG. 32A is an IR-ATR of crystalline naltrexone formed by slow cooling using acetone (Lewis basic).
Figure 32B:
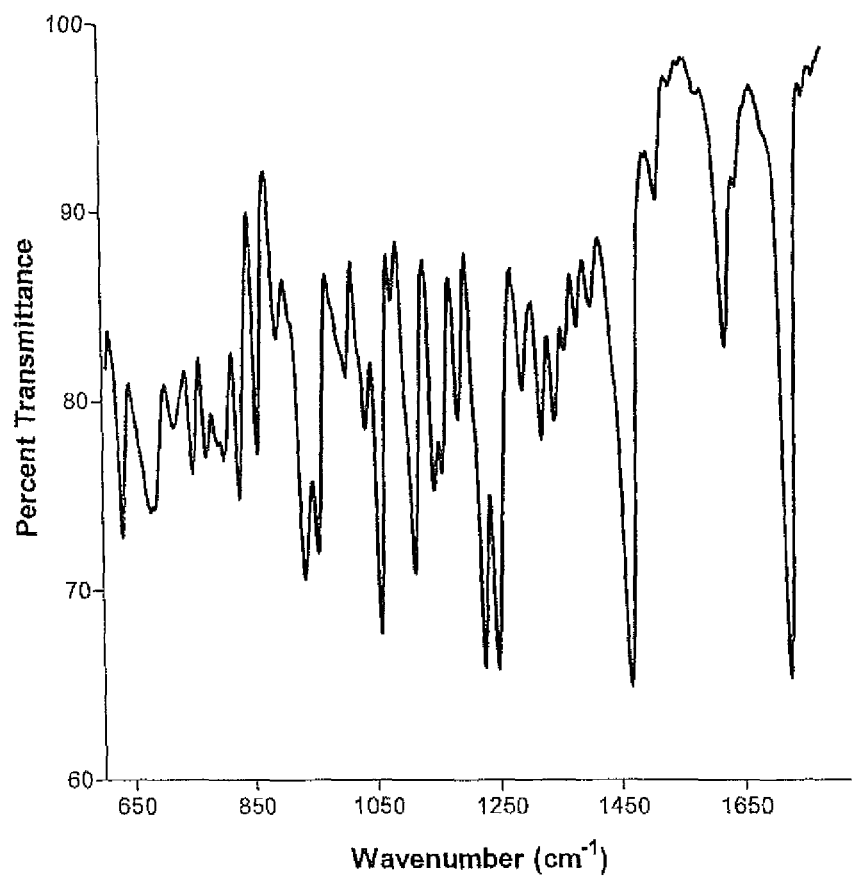
FIG. 32B is an IR-ATR of crystalline naltrexone formed by fast cooling using acetone (Lewis basic).
Figure 33A:
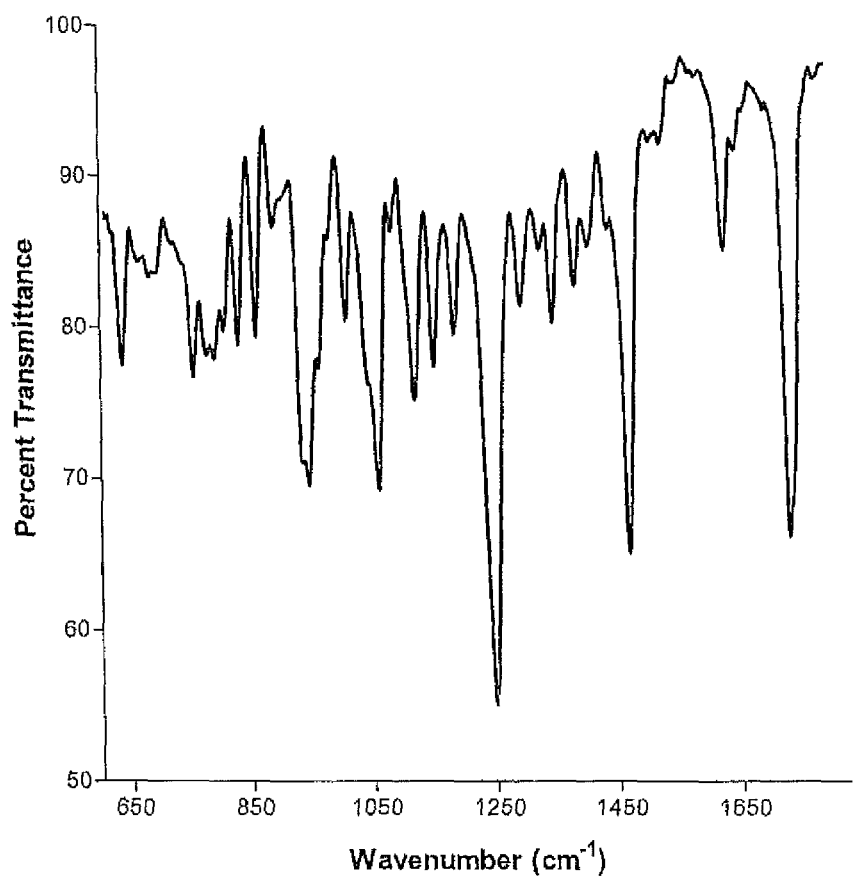
FIG. 33A is an IR-ATR of crystalline naltrexone formed by slow cooling using ethyl acetate (Lewis basic).
Figure 33B:
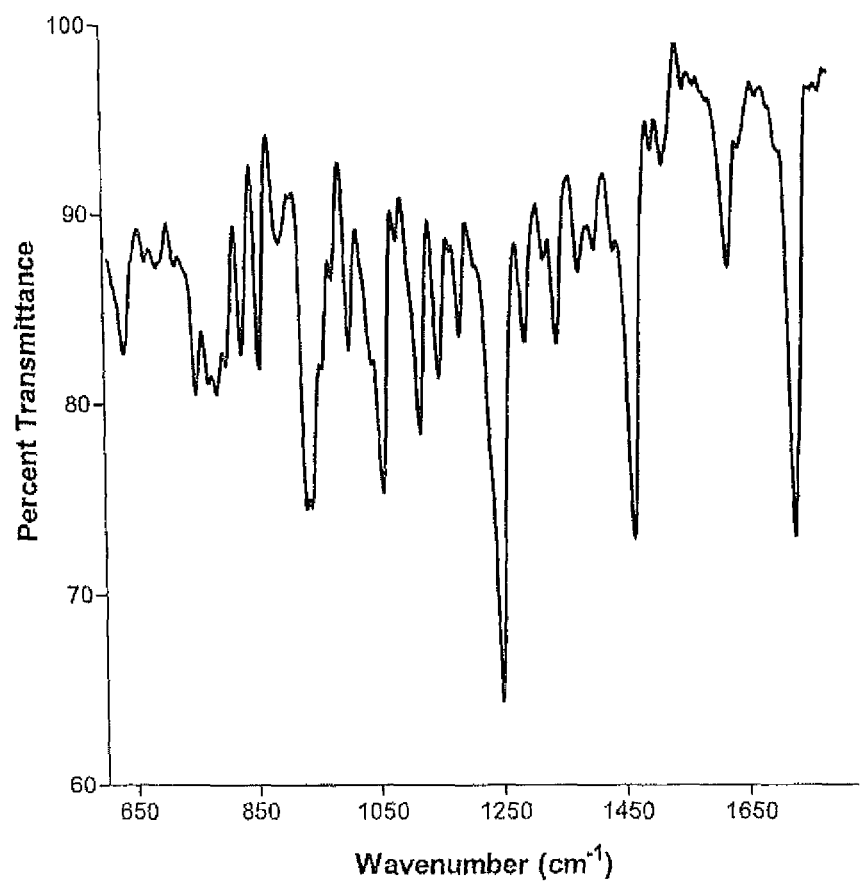
FIG. 33B is an IR-ATR of crystalline naltrexone formed by fast cooling using ethyl acetate (Lewis basic).
Figure 34A:
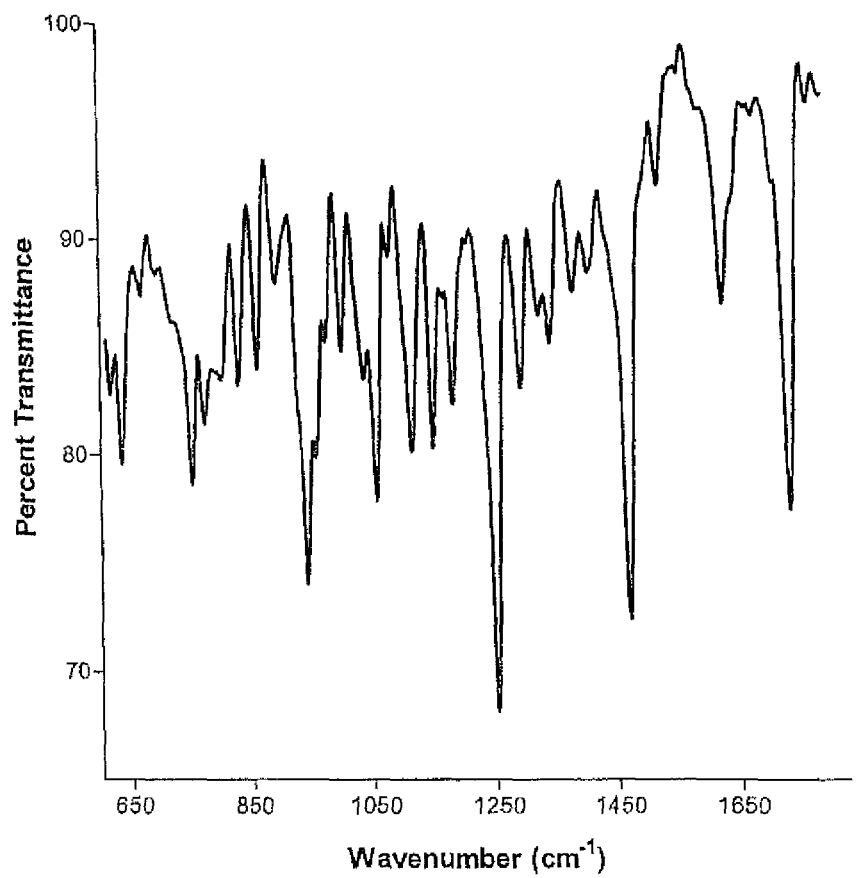
FIG. 34A is an IR-ATR of crystalline naltrexone formed by slow cooling using methyl ethyl ketone (Lewis basic).
Figure 34B:
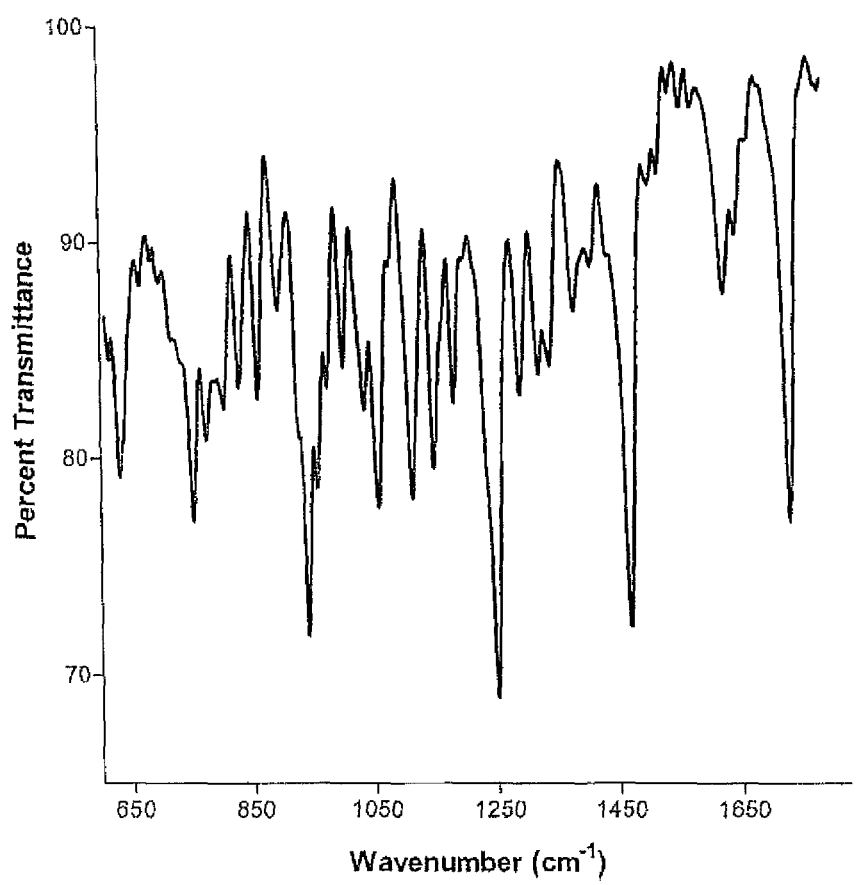
FIG. 34B is an IR-ATR of crystalline naltrexone formed by fast cooling using methyl ethyl ketone (Lewis basic).
Figure 35A:
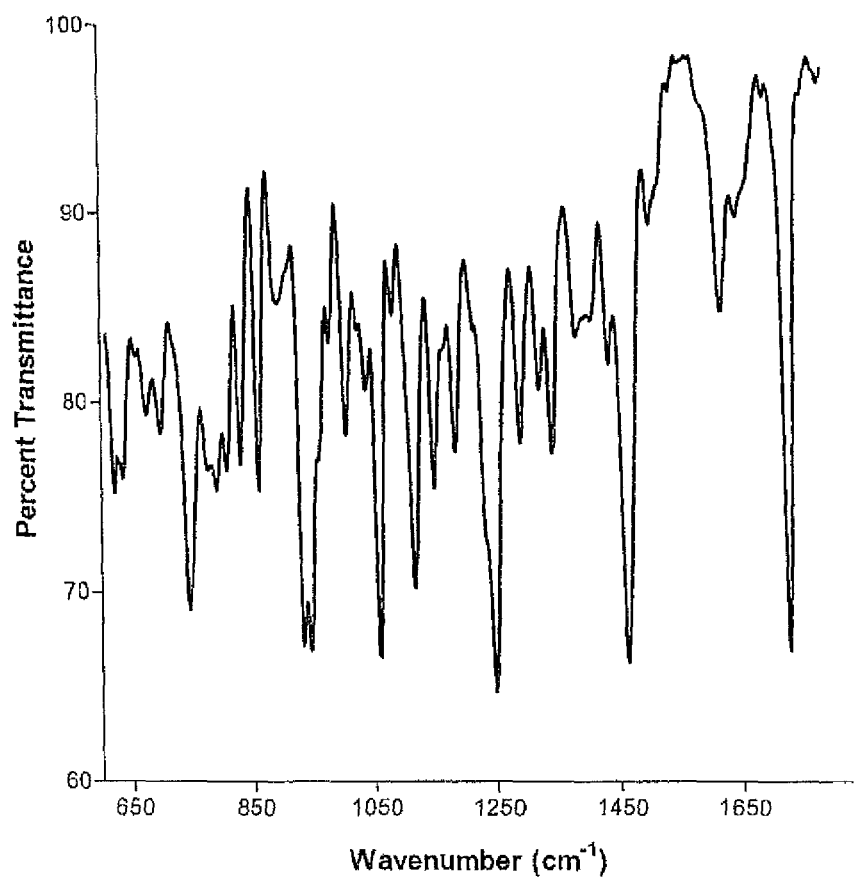
FIG. 35A is an IR-ATR of crystalline naltrexone formed by slow cooling using toluene (aromatic).
Figure 35B:
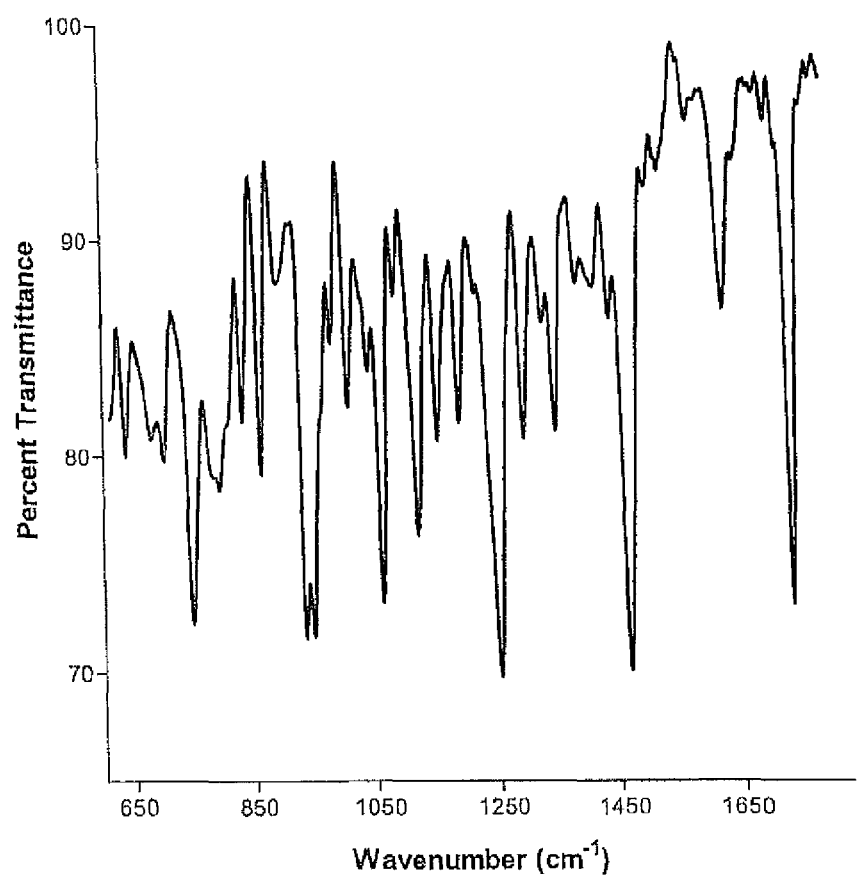
FIG. 35B is an IR-ATR of crystalline naltrexone formed by fast cooling using toluene (aromatic).
Figure 36A:
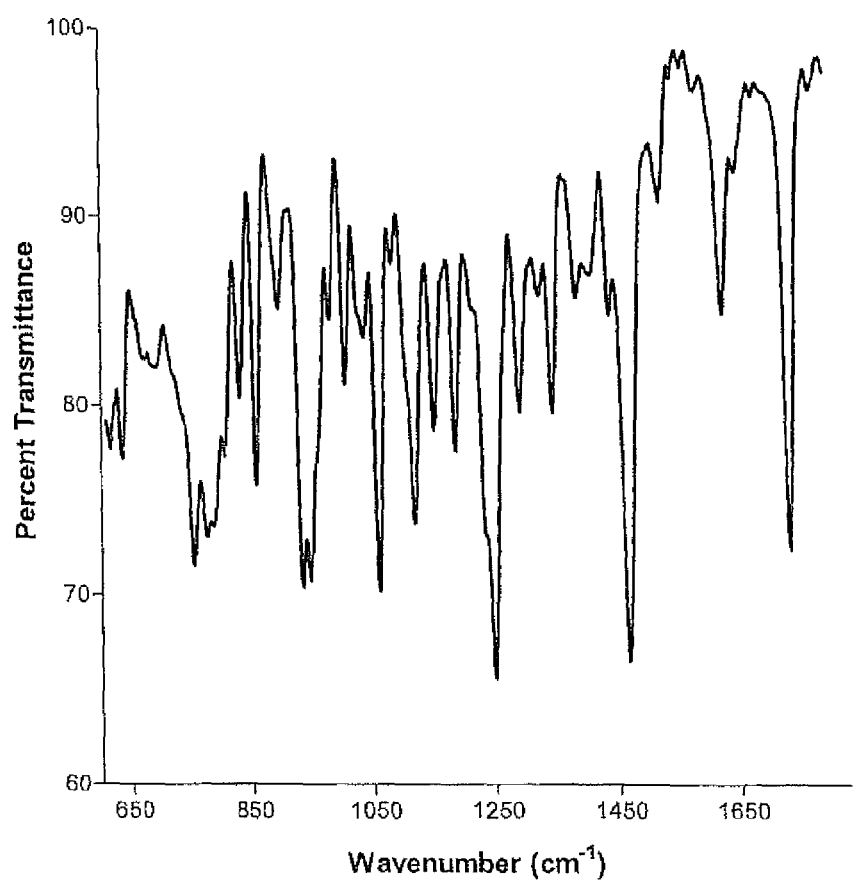
FIG. 36A is an IR-ATR of crystalline naltrexone formed by slow cooling using hexane (non-polar).
Figure 36B:
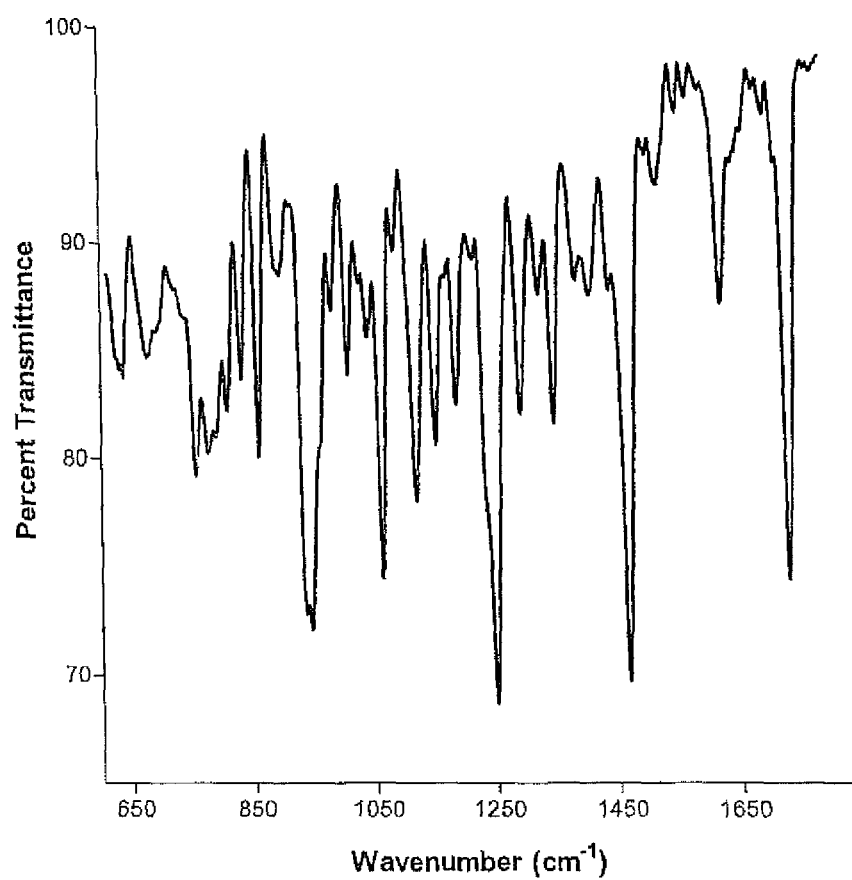
FIG. 36B is an IR-ATR of crystalline naltrexone formed by fast cooling using hexane (non-polar).
Figure 37:
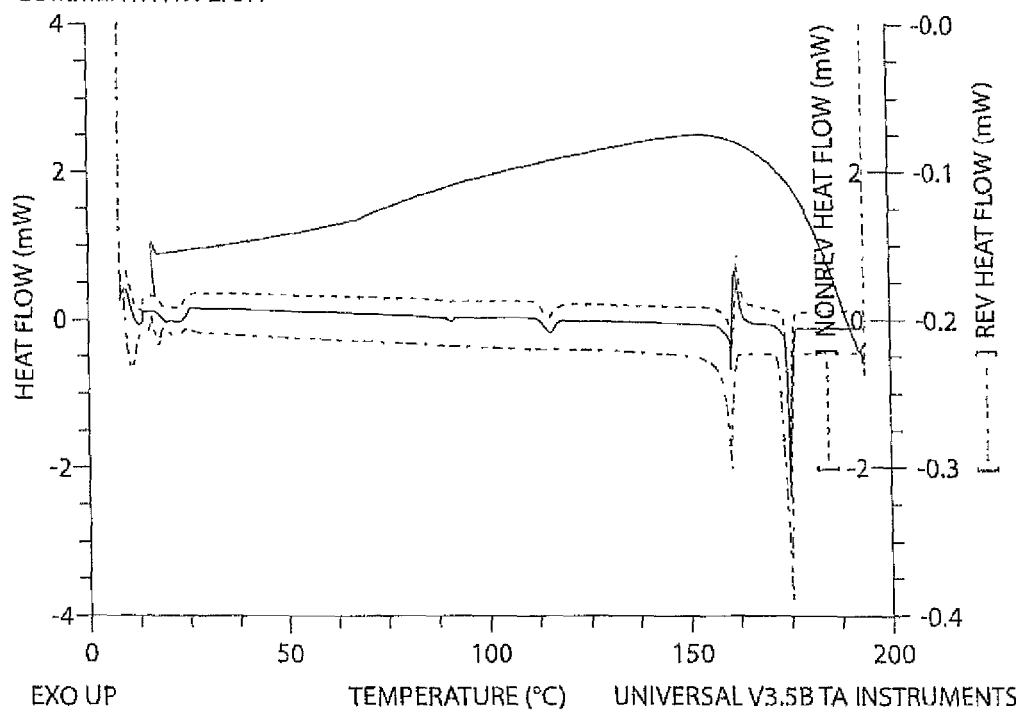
FIG. 37 is the DSC of an ethanolate (clathrate) form of naltrexone.

| Solvent | Slow Cooling Process | | | Fast Cooling Process | | |
|---|---|---|---|---|---|---|
| | XRPD | DSC | IR-ATR | XRPD | DSC | IR-ATR |
| Acetonitrile | FIG. 1a | FIG. 13a | FIG. 25a | FIG. 1b | FIG. 13b | FIG. 25b |
| Dimethyl formamide | FIG. 2a | FIG. 14a | FIG. 26a | FIG. 2b | FIG. 14b | FIG. 26b |
| Water | ///// | ///// | ///// | FIG. 3 | FIG. 15 | FIG. 27 |
| Methanol | FIG. 4a | FIG. 16a | FIG. 28a | FIG. 4b | FIG. 16b | FIG. 28b |
| Ethanol | FIG. 5a | FIG. 17a | FIG. 29a | FIG. 5b | FIG. 17b | FIG. 29b |
| Benzyl alcohol | ///// | ///// | ///// | FIG. 6 | FIG. 18 | FIG. 30 |
| Dichloromethane | FIG. 7a | FIG. 19a | FIG. 31a | FIG. 7b | FIG. 19b | FIG. 31b |
| Acetone | FIG. 8a | FIG. 20a | FIG. 32a | FIG. 8b | FIG. 20b | FIG. 32b |
| Ethyl acetate | FIG. 9a | FIG. 21a | FIG. 33a | FIG. 9b | FIG. 21b | FIG. 33b |
| Methyl ethyl ketone | FIG. 10a | FIG. 22a | FIG. 34a | FIG. 10b | FIG. 22b | FIG. 34b |
| Toluene | FIG. 11a | FIG. 23a | FIG. 35a | FIG. 11b | FIG. 23b | FIG. 35b |
| Hexane | FIG. 12a | FIG. 24a | FIG. 36a | FIG. 12b | FIG. 24b | FIG. 36b |

///// = not available

Melting/decomposition temperature ranges were defined from the extrapolated onset to the maximum of the melting/decomposition endotherm.

Other DSC measurements were obtained by TA Instruments Q 1000 DSC using hermetic pans and a DSC ramp method using a heating rate of 10° C./min. or 50° C./min. from 0° C. to 200° C. Those skilled in the art will recognize other appropriate means of measuring DSC.

DSC thermograms of the various naltrexone materials obtained by slow and fast cooling from a variety of solvent systems are shown in the Figures.

5. Infrared Absorption Spectroscopy

The solid-state infrared (IR) spectrum of the analyte was obtained using a Buck Scientific model M-500 infrared spectrometer, operating in the single beam mode, and using the attenuated total reflectance (ATR) detection mode. The sample was clamped against the ZnSe crystal single reflection horizontal ATR sampling accessory, sold under the tradename MIRacle™ by Pike Technologies.

IR-ATR spectra of the various Naltrexone products obtained by slow and fast cooling from a variety of solvent systems are shown in the Figures.

Naltrexone Ethanolate

In particular, the Applicants prepared a polymorphic form of naltrexone ethanolate which is characterized by an X-ray powder diffraction with a characterizing peak at about 9° (2θ). This peak appears irrespective of which of the two processes for preparing were employed.

The resulting analysis showed that the polymorphic form of naltrexone can be characterized by the X-ray powder diffraction pattern of FIG. 5A. The polymorphic form can be further characterized by the DSC pattern of FIG. 17A and/or the IR-ATR of FIG. 29A.

This polymorphic form of naltrexone can be characterized by the X-ray powder diffraction pattern of FIG. 5B. The polymorphic form can be further characterized by the DSC pattern of FIG. 17B and/or the IR-ATR of FIG. 29B.

Figure 46:
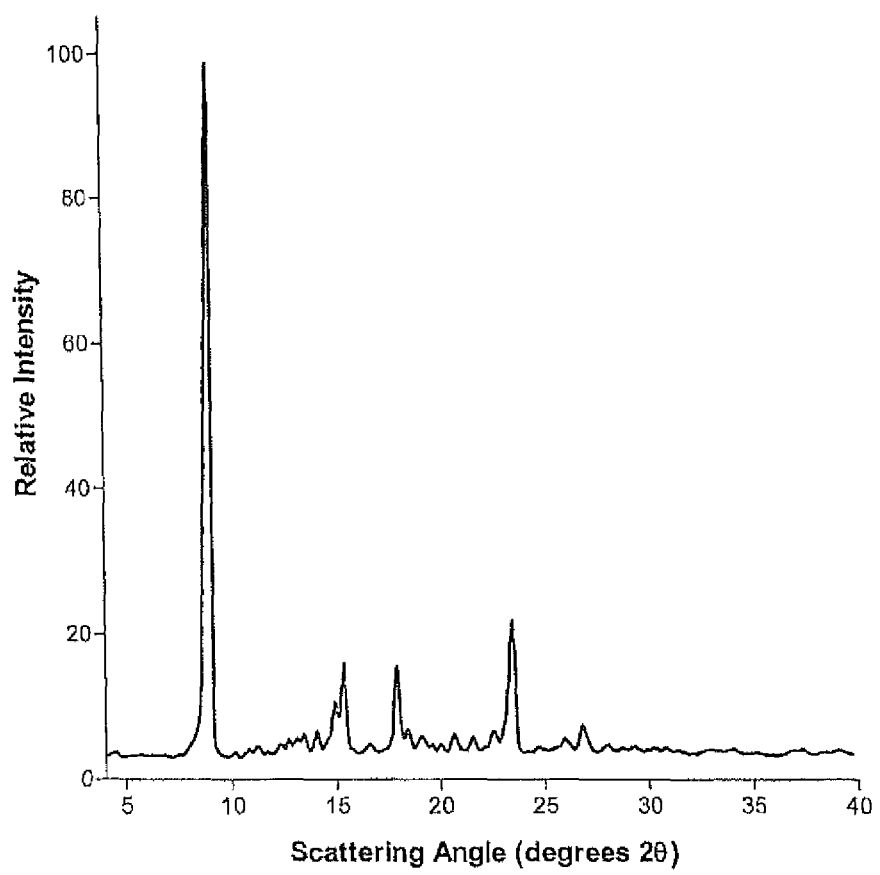
FIG. 46 is an XRPD pattern for naltrexone ethanolate.
Figure 47:
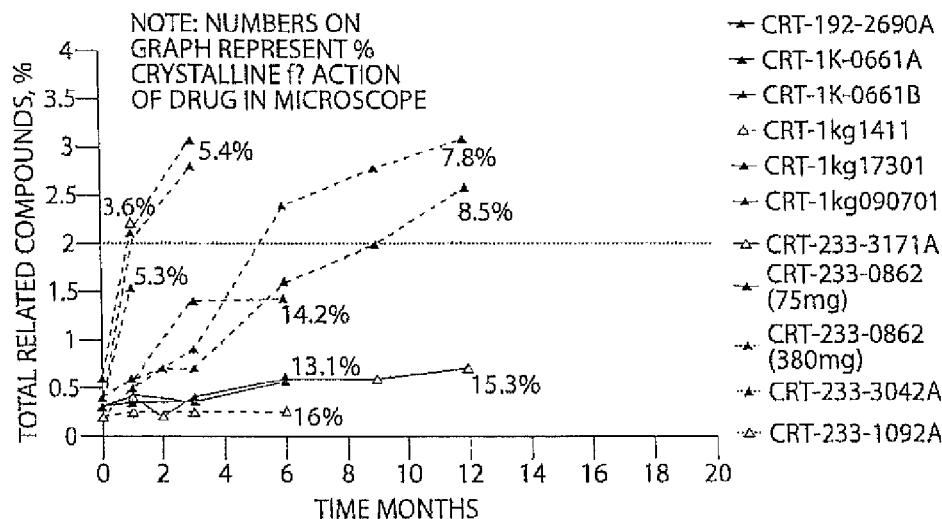
FIG. 47 is a graph illustrating the effect of crystallinity on microparticle impurity generation at controlled room temperature.
Figure 48:
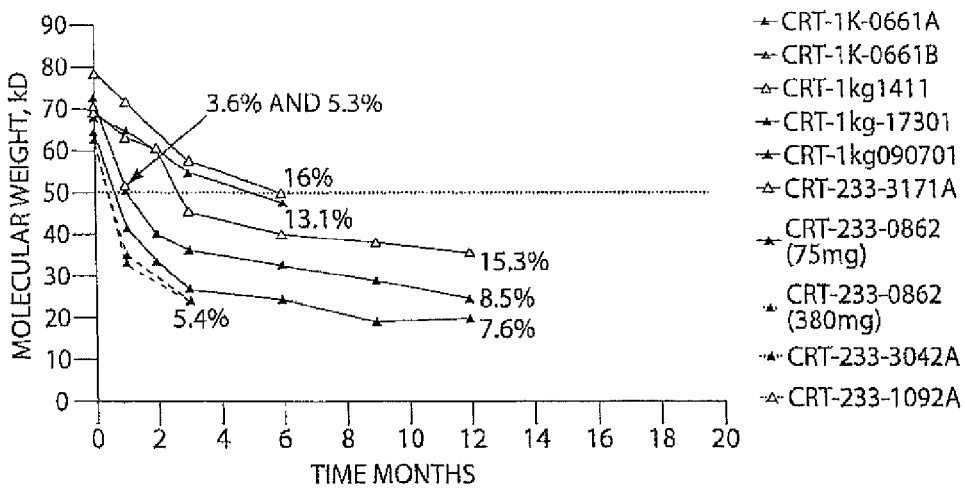
FIG. 48 is a graph illustrating the effect of crystallinity on microparticle decay at controlled room temperature.
Figure 49A:
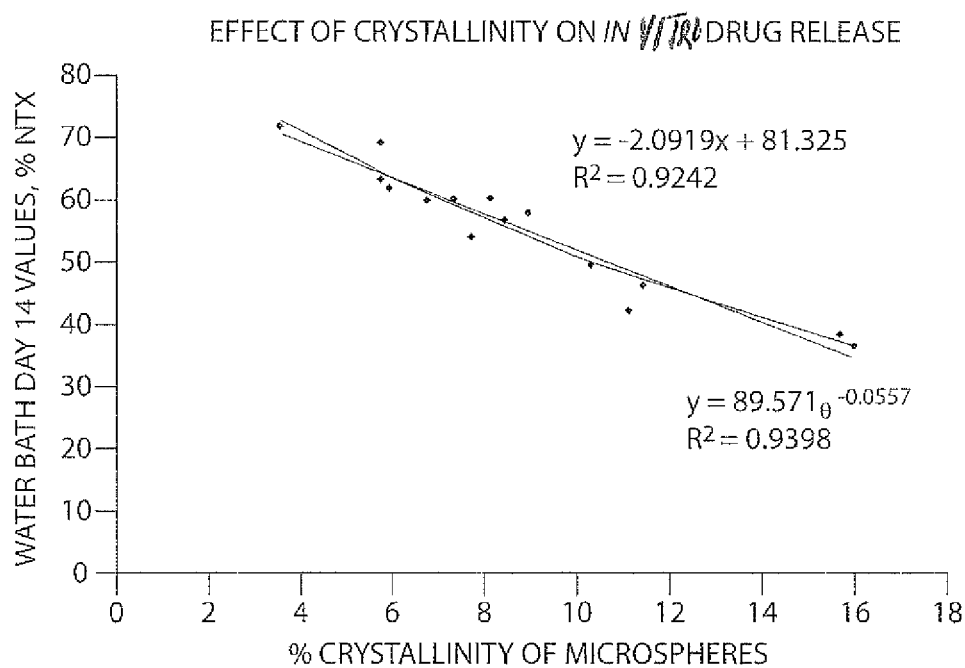
FIGS. 49A and 49B illustrate the effect of crystallinity on in vitro and in vivo drug release.
Figure 49B:
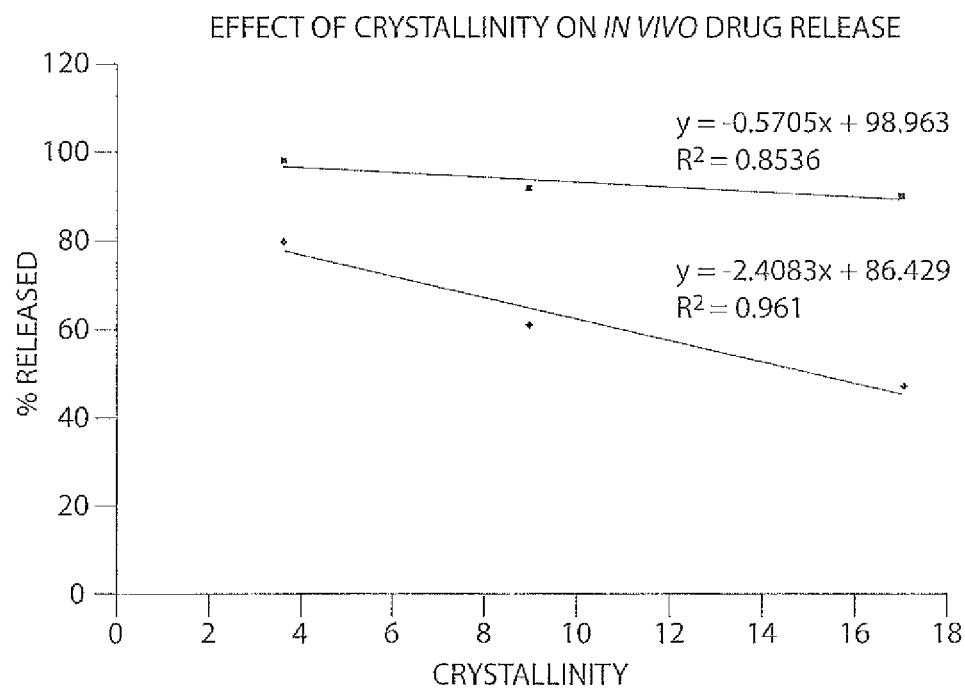

A polymorphic form of naltrexone ethanolate can also be characterized by FIG. 46. A purified naltrexone ethanolate according to the invention can be prepared in the substantial absence of one or more polymorphic forms of naltrexone selected from the group consisting of, for example, naltrexone benzyl alcohol solvate, naltrexone monohydrate, and anhydrous naltrexone. As used herein, the "substantial absence" is intended to mean having no or negligible (including detectable) amounts of the identified substance, as can be arrived at by processes intending to avoid the formation of the identified substance or by processes intended to remove the identified substance.

Further, a polymorphic form according to the invention can be prepared wherein the form is in the complete absence of naltrexone benzyl alcohol solvate, as can be arrived at by employing a process which avoids the use of benzyl alcohol as or in the solvent system. In another embodiment, the polymorphic form is present with naltrexone benzyl alcohol solvate, and in amount of at least about 88% or less than about 65% by weight of total crystalline naltrexone or, alternatively, is not present in an amount of about 67.0%, 76.3 or 85.7% by weight of total crystalline naltrexone.

An ethanolate form of naltrexone characterized by the XRPD in FIG. 5A, 5B or 46 are examples of a form in the absence of naltrexone benzyl alcohol solvate.

Of particular interest to those skilled in the art is a polymorphic form of the invention wherein the form is substantially pure.

Anhydrous Form

Other forms of the invention are contemplated. For example, an anhydrous polymorphic form of naltrexone was prepared which form can be characterized by an X-ray powder diffraction with a characterizing peak at about 8° (2θ).

For example, the polymorphic form of naltrexone can be characterized by the X-ray powder diffraction pattern of FIG. 1A. Additionally, this polymorphic form can be further characterized by the DSC pattern of FIG. 13A. Still further, this polymorphic form can be characterized by the IR-ATR of FIG. 25A.

Such a polymorphic form of naltrexone can be characterized by the X-ray powder diffraction pattern of FIG. 1B.

Still further, the polymorphic form can be further characterized by the DSC pattern of FIG. 13B. Additionally, this polymorphic form can be further characterized by the IR-ATR of FIG. 25B.

Figure 43:
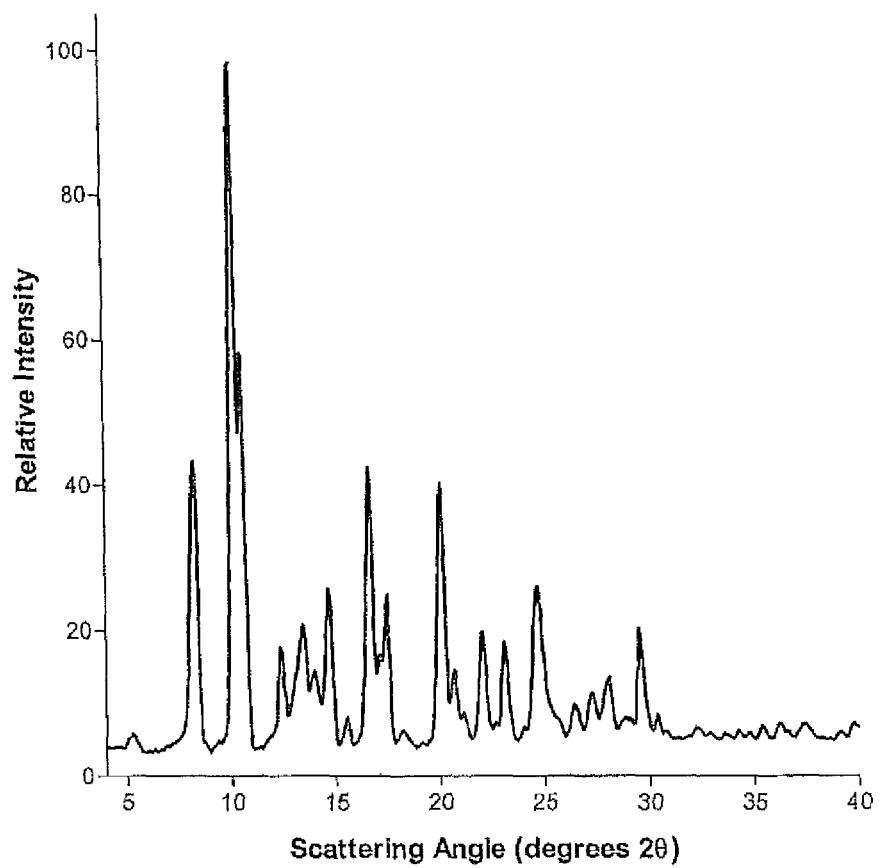
FIG. 43 is an XRPD pattern for naltrexone base anhydrous.

Alternatively or additionally, the polymorphic form can be characterized by the XRPD of FIG. 43.

Monohydrate

Figure 44:
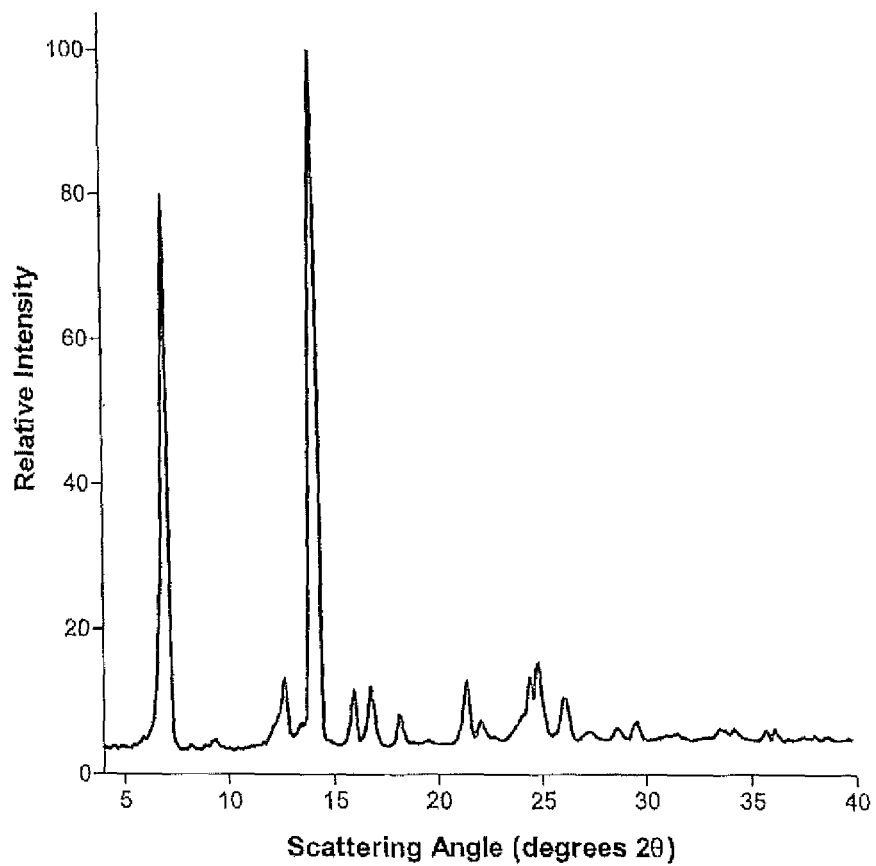
FIG. 44 is an XRPD pattern for naltrexone monohydrate.

Applicants also prepared a monohydrate form of naltrexone formed by using water as the solvent. This polymorphic form of naltrexone is characterized by an X-ray powder diffraction with a characterizing peak at about 7° (2θ). This polymorphic form of naltrexone can be characterized by the X-ray powder diffraction pattern of FIGS. 3 and 44. Further, the polymorphic form at about 7 can be characterized by the DSC pattern of FIG. 15. Additionally, the polymorphic form can be further characterized by the IR-ATR of FIG. 27.

Benzyl Alcohol Solvate

Figure 45:
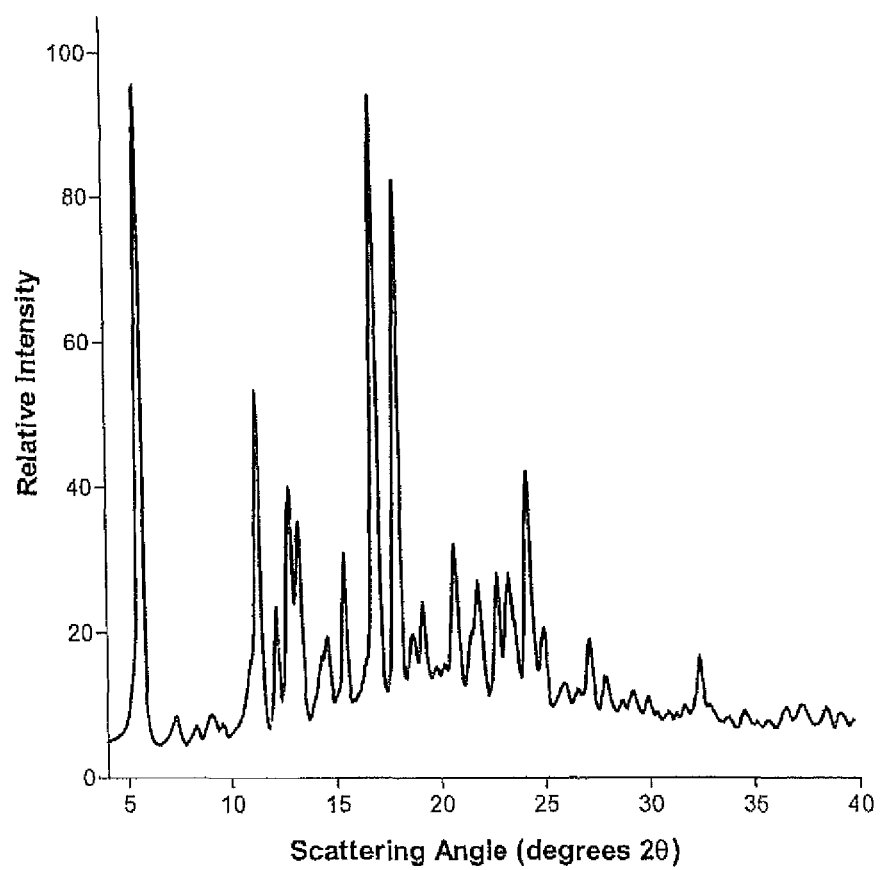
FIG. 45 is an XRPD pattern for naltrexone benzyl alcohol solvate.

Applicants have prepared another polymorphic form of naltrexone which can be characterized by an X-ray powder diffraction with a characterizing peak at about 5-6° (2θ). Additionally, a polymorphic form of naltrexone can be characterized by the X-ray powder diffraction pattern of FIGS. 6 and 45. Still further, the polymorphic form can be characterized by the DSC pattern of FIG. 18. Also, a polymorphic form can be characterized by the IR-ATR of FIG. 30.

Further, a polymorphic form according to the invention can be prepared wherein the form is in the complete absence of naltrexone ethanolate, as can be arrived at by employing a process which avoids the use of ethanol as or in the solvent system. In another embodiment, the polymorphic form is present with naltrexone ethanolate, and in amount of at least about 35% or less than about 13% by weight of total crystalline naltrexone or, alternatively, is not present in an amount of about 33.0%, 23.7 or 14.3% by weight of total crystalline naltrexone.

Other polymorphs, including the solvates specifically described herein and combinations thereof, are a part of the invention.

Amorphous Naltrexone

Figure 42:
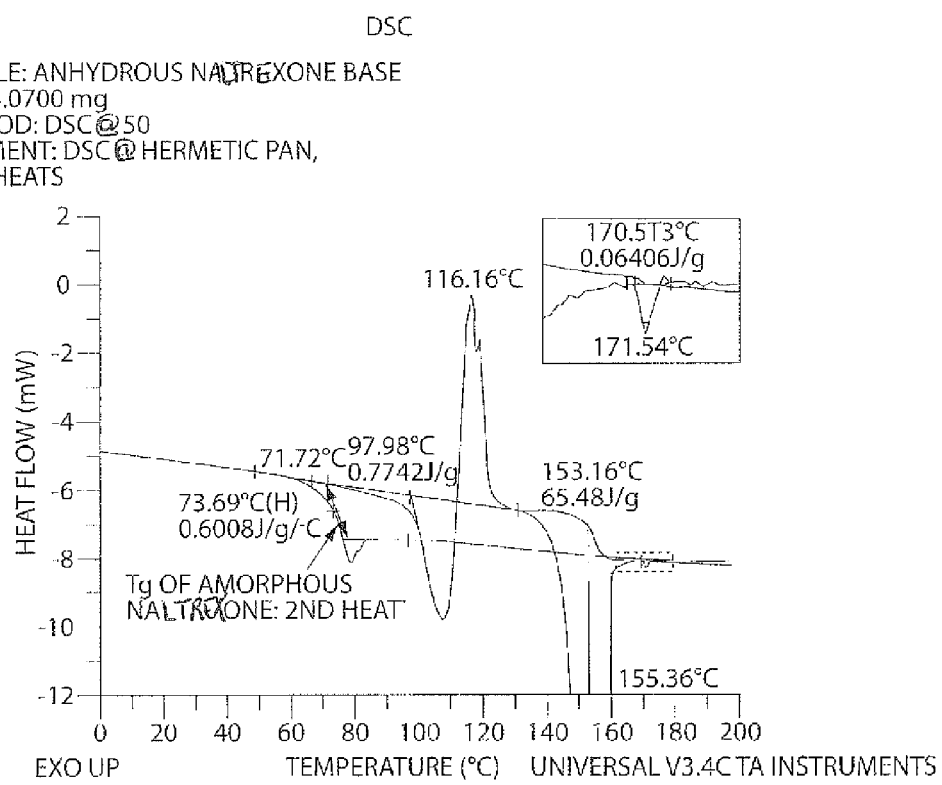
FIG. 42 is a DSC of amorphous naltrexone.

Applicants have also prepared an amorphous form of naltrexone which can be characterized by the DSC pattern of FIG. 42. Amorphous naltrexone form was prepared by leaving NTX base in 180-190° C. oven for approximately 10 minutes. After being melted, it was taken out to cool at room temperature. It was then broken up into small pieces using a spatula and ground into fine powders using mortar and pestle. The X-ray powder diffraction pattern confirmed that the powder was amorphous.

Methods of Making an Isolated and/or Substantially Pure Form or Mixture of Forms of Naltrexone The forms can be prepared by a method comprising:
(i) mixing a naltrexone, such as a naltrexone base anhydrous or a salt, such as hydrochloride, with a solvent or solvent system containing one or more organic or aqueous solvents, such as acetonitrile, dimethyl formamide, water, methanol, ethanol, benzyl alcohol, dichloromethane, acetone, ethyl acetate, methyl ethyl ketone, toluene and hexane; (ii) heating the solvent or solvent system to within about 1-10° C. of the boiling point to prepare nearly saturated solutions; (iii) slowly cooling the resulting nearly saturated solutions to room temperature, such as at a rate not greater than 1-2° C./min, thereby forming precipitated materials; and (iv) harvesting the precipitated materials. This method is also referred to herein as the slow process or cooling method.

Examples of materials prepared by this method can be characterized by the X-ray powder diffraction pattern selected from the group consisting of FIGS. 1A, 2A, 4A, 5A, 7A, 8A, 9A, 10A, 11A, and 12A.

Still further, precipitated materials prepared by this method can be characterized by the DSC pattern selected from the group consisting of FIGS. 13A, 14A, 16A, 17A, 19A, 20A, 21A, 22A, 23A and 24A. Additionally, the precipitated materials can be characterized by the IR-ATR selected from the group consisting of FIGS. 25A, 26A, 28A, 29A, 31A, 32A, 33A, 34A, 35A, and 36A.

Alternatively, Applicants prepared the polymorphs of the instant invention by the method comprising: (i) mixing a naltrexone base anhydrous with a solvent selected from the group consisting of acetonitrile, dimethyl formamide, water, methanol, ethanol, benzyl alcohol, dichloromethane, acetone, ethyl acetate, methyl ethyl ketone, toluene and hexane; (ii) heating the solvent or solvent system to within about 5-10° C. of the boiling point to prepare nearly saturated solutions; (iii) quickly cooling the resulting nearly saturated solutions, such as rapidly as possible, to about room temperature, or less, thereby forming precipitated materials; and (iv) harvesting the precipitated materials. This is also referred to herein as the fast process or cooling method.

Material prepared by the fast method can be characterized by the X-ray powder diffraction pattern selected from the group consisting of FIGS. 1B, 2B, 3, 4B, 5B, 6, 7B, 8B, 9B, 10B, 11B, and 12B. Further, precipitated materials prepared by this method can be characterized by the DSC pattern selected from the group consisting of FIGS. 13B, 14B, 15, 16B, 17B, 18, 19B, 20B, 21B, 22B, 23B and 24B. Additionally, they can be characterized by the IR-ATR selected from the group consisting of FIGS. 25B, 26B, 27, 28B, 29B, 30, 31B, 32B, 33B, 34B, 35B, and 36B.

In one embodiment, the novel forms can be manufactured during the process for producing the formulation, such as the specific process for formulating the extended release formulation, referred to herein as formulation A, as described below in the exemplification. In yet another embodiment, the invention excludes the extended release formulation, formulation A, described below in the exemplification.

Mixtures of Polymorphic Forms

Applicants have discovered that compositions comprising mixtures of two or more forms and/or mixtures of crystalline and non-crystalline drug possess particular advantages in extended release formulations. Thus, the invention also relates to mixtures of such naltrexone products.

In one aspect of the invention, the naltrexone comprises a mixture of crystalline and non-crystalline forms. For example, the % crystallinity of the naltrexone can be at least about 10%, preferably at least about 20% (by weight) of the total naltrexone, preferably in an amount of at least about 30%, at least about 40%, at least about 50%, at least about 60% (by weight) of the total naltrexone. In one embodiment the % crystallinity of naltrexone is present in an amount between about 10% and 70%, preferably between about 30% and 50% (by weight), of the total naltrexone. In another embodiment, the % crystallinity is not 41%, 34.3%, or 35.2% of total naltrexone.

The crystalline naltrexone present in such compositions can be any crystalline form of naltrexone. Preferably the crystalline form includes naltrexone ethanolate, more preferably naltrexone ethanolate clathrate. The naltrexone ethanolate is preferably present in the crystalline form in an amount of at least about 40% by weight, more preferably in an amount of at least about 50% by weight, more preferably in an amount of about 60% by weight.

Non-crystalline naltrexone can be in the form of amorphous and/or dissolved naltrexone relative to the composition or composition matrix. By amorphous (or free amorphous) naltrexone is meant that the amorphous form exists as a separate phase, such as when present in the matrix. By dissolved naltrexone is meant drug and matrix exist as a single phase. An example of a dissolved naltrexone includes a naltrexone present in a polymeric extended release formulation wherein the naltrexone is dissolved in polymeric matrix. Such an extended release device includes that described in the exemplification below.

Thus, in one aspect of the invention, the non-crystalline naltrexone in the naltrexone composition can be from 0-100% by weight dissolved, preferably at least about 20% is dissolved, more preferably at least about 50% is dissolved, more preferably at least about 80% is dissolved. In one embodiment, substantially all of the non-crystalline form is dissolved naltrexone.

The inventions also include mixtures of the forms described herein. Thus, the inventions include, for example, naltrexone ethanolate (such as, naltrexone ethanolate clathrate) alone or in combination with one or more of the other forms described herein (in the presence, absence or substantial absence of non-crystalline (amorphous and/or dissolved) naltrexone). Such combinations can include compositions that have between 0 and 100% by weight of any particular form. The composition preferably includes naltrexone ethanolate. Preferred amounts of naltrexone ethanolate include at least about 10% by weight of total crystalline product, preferably at least about 20%, at least about 30%, at least about 40%, at least about 50%, at least about 60%, at least about 70%, at least about 80%, or at least about 90% by weight of total crystallinity. In one preferred embodiment, the naltrexone ethanolate is present in the amount of about 60%. In another embodiment, the naltrexone ethanolate is absent in the amount of about 60%. The percentages represent the fraction of crystallinity as determined by relative peak intensity of characterizing peaks.

In yet another aspect, compositions of the invention are prepared wherein the crystalline naltrexone is in the substantial absence of a polymorphic form of naltrexone selected from the group consisting of: naltrexone benzyl alcohol solvate, naltrexone monohydrate, and anhydrous naltrexone. Such compositions preferably possess naltrexone ethanolate, such as naltrexone ethanolate clathrate, in the preferred amounts described above.

A preferred mixture includes about 50-70% naltrexone ethanolate and the balance naltrexone benzyl alcohol solvate. Another mixture includes about 10-15% of naltrexone monohydrate; about 10-15% naltrexone anhydrous; about 10-15% naltrexone benzyl alcohol solvate; and the balance of the composition is naltrexone ethanolate. Of course, the claimed invention may include other mixtures of naltrexone forms as well, including mixtures characterized by two or three of the above forms, substituting one or more other forms for one or more of the above, (including, but not limited to, one or more of the other forms described herein), modifying the amounts of one or more of the forms, adding an additional form, etc.

Utility

The present invention provides a method for the treatment of a patient afflicted with addictive diseases or central nervous system disorders wherein such disease states may be treated by the administration of an effective amount of naltrexone of the present invention to a patient in need thereof.

Thus, where the composition is being administered to treat addictive behavior, a therapeutically effective amount of naltrexone is, preferably, an amount effective in controlling or reducing the addictive behavior. The term "controlling" is intended to refer to all processes wherein there may be a slowing, interrupting, arresting, or stopping of the addictive or other behavior characteristic of the disease and does not necessarily indicate a total elimination of all disease symptoms.

The term "therapeutically effective amount" is further meant to define an amount resulting in the improvement of any parameters or clinical symptoms. The actual dose may vary with each patient.

As used herein, the term "subject" or "patient" refers to a warm blooded animal, including but not limited to humans, such as a mammal which is afflicted with a particular disease state.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described for example in Remington's Pharmaceutical Sciences, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, by enteral, oral, buccal, rectal, vaginal, dermal, nasal, bronchial, tracheal, pulmonary, parenteral, subcutaneous, intravenous, intramuscular, or intraperitoneal route, by injection, ingestion, or inhalation, for example.

A particularly preferred route of administration includes sustained release formulations, extended release formulations, or long acting formulations, that permit delivery, such as substantially continuous delivery of drug over an extended period of time, such as greater than one, two, three, four or more weeks. A four week release is preferred.

For oral administration, the compounds can be formulated, for example, in a solid, such as capsules, pills, tablets, lozenges, melts, powders, or in a form for mixing into a solution, suspension or emulsion.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers include water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

For surgical implantation, the active ingredients may be combined with any of the well-known biodegradable and bioerodible carriers, such as polylactides and poly-lactide-co-glycolides and collagen formulations. Such materials may be in the form of solid implants, sponges, and the like. In any event, for local use of the materials, the active ingredients usually be present in the carrier or excipient in a weight ratio of from about 1:1000 to 1:20,000, but are not limited to ratios within this range.

Preferably, the compounds are in an extended release formulation. Extended (also referred to as sustained or controlled release) preparations may be achieved through the use of polymers (preferably poly-lactide or poly-lactide-co-glycolide polymers) to entrap or encapsulate the naltrexone described herein. Extended release formulations can be made by spray drying polymer-drug mixtures, emulsion-based technologies, coacervation based technologies, film casting, extrusion based technologies and other processes to manufacture polymer-drug microparticles possessing an extended release profile. Examples of suitable extended release technologies that can be used to incorporate the novel naltrexone forms described herein include, without limitation, the MEDISORB® technology, as described in, for example, U.S. Pat. No. 6,264,987 to Wright, U.S. Pat. No. 5,654,008 and/or U.S. Pat. No. 5,792,477, for example; the PROLEASE® technology, as described, for example in U.S. Pat. No. 6,358,443 to Herbert; the technologies described by Southern Research Institute, as described for example in U.S. Pat. No. 6,306,425; and "Method of Preparing Sustained Release Microparticles," U.S. Application No. 60/441,946, filed Jan. 23, 2003, and the technologies described by Alza Corp., including the ALZAMER® Depot injection technology. The contents of these patents are incorporated herein by reference in their entirety.

In a preferred embodiment, the extended release formulation delivers therapeutically beneficial amounts of naltrexone to the patient for a period of at least one week, preferably at least about two weeks, more preferably at least about 3 or about 4 or more weeks.

In one preferred embodiment, the naltrexone is present in the extended release device or formulation in an amount of at least about 5% by weight, preferably at least about 10% by weight, more preferably at least about 30% by weight of the total weight of the device, or formulation. In one embodiment, the theoretical drug load is not 35% (or actual drug load of 40%, 45.8% or 26.1% load) by weight of the total sustained release device. However, in a preferred embodiment, the theoretical drug load is 35% total naltrexone.

It has been discovered that controlling the crystallinity of the total amount of naltrexone has a substantial impact upon the duration of release. For example, a composition containing PLGA microspheres, as described herein, characterized by total % naltrexone crystallinity between about 9-12% in a PLGA microsphere possesses a superior release profile of about 4 weeks. Lowering the % crystallinity can quicken the release. Thus, a composition containing PLGA microspheres, as described herein, characterized by total % naltrexone crystallinity of between about 4-9% in a PLGA microsphere possesses a superior release profile of less than 4 weeks, e.g. about 2 weeks. Likewise, a composition containing PLGA microspheres, as described herein, characterized by total % naltrexone crystallinity of about 12% or more in a PLGA microsphere possesses a superior release profile of at least 4 weeks, e.g. about 8 weeks. Such a substantial impact upon the duration of release, based on the % crystallinity was unexpected.

Alternatively, instead of incorporating naltrexone into polymeric particles, it is possible to entrap these materials in microparticles prepared. For example, coacervation techniques, interfacial polymerization (for example, hydroxymethylcellulose or gelatine-microcapsules and poly-(methylmethacrylate) microcapsules, respectively), colloidal drug delivery systems (for example, liposomes, albumin, microparticles, microemulsions, nanoparticles, and nanocapsules), or macroemulsion systems can be used.

When the composition is to be used as an injectable material, including but not limited to needle-less injection, it can be formulated into a conventional injectable carrier. Suitable carriers include biocompatible and pharmaceutically acceptable solutions.

Method for Manufacturing Extended Release Devices

The invention includes a preferred method for manufacturing extended release devices, wherein the resulting device contains preferred mixtures of the described polymorphic forms.

Polymer solution can be formed by dissolving a poly(lactide)-co-glycolide polymer, such as a 75:25 DL PLGA (poly(lactide)-co-glycolide) in a polymer solvent, such as ethyl acetate (EtAc), to form a solution. Preferred PLGA polymers are high molecular weight polymers, such as polymers possessing a molecular weight of at least about 100,000 daltons. A naltrexone solution can be formed by dissolving naltrexone base in a suitable solvent, such as one of the solvents described above, including benzyl alcohol (BA), to form a solution. The polymer solution and the naltrexone solution are preferably mixed together to form a drug/polymer solution that will be the "organic" or "oil" phase of the emulsion.

The "aqueous" or "continuous" phase of the emulsion (emulsifying solution) is prepared. The aqueous phase preferably contains poly(vinyl alcohol) (PVA) and polymer solvent, such as EtAc. The organic phase and the aqueous phase can be conveniently combined in a first static mixer to form an oil-in-water emulsion.

In an optional partial extraction step, the emulsion flows out of the first static mixer and into a second static mixer where the emulsion can be combined with a primary extraction solution which enters the second static mixer. The primary extraction solution (such as can be formed by an EtAc aqueous solution) can initiate solvent extraction from the microdroplets of the emulsion during the partial primary extraction step in the second static mixer.

The outflow of the first or second static mixer can flow into an extraction vessel containing primary extraction solution. The solvents (BA and EtAc) are substantially extracted from the organic phase of the emulsion in this primary solvent extraction step, resulting in nascent microparticles comprised mainly of polymer and drug. The primary solvent extraction step lasts for approximately six hours.

The microparticles can be collected, and vacuum dried, optionally with a nitrogen bleed using a customized vibratory sieve. After collection and prior to drying, the microparticles are rinsed with a 25% ethanol solution that removes the emulsifying agent (PVA), and enhances yield by aiding in the transfer of the microparticles to the cold dryer. This step is conducted, preferably at cold temperatures, until the desired level of dryness is achieved. As can be seen in the examples below, the degree of dryness (as measured, for example, by a humidity probe) impacts the degree of crystallinity achieved in the final product. For example, it can be advantageous to select a drying time of at least about 8, 16, 24 or 40 hours of drying. For example, it can be advantageous to select a drying time of at least about 8, 16, 24 or 40 hours where drying is 40%, 70%, 95% or 100% complete respectively. Drying is considered complete when the absolute humidity of the effluent gas reaches approximately 0 g/m$^3$.

The microparticles can then be resuspended in a second extraction solution. The second solution can contain the solvent desired to form the polymorphic form, such as ethanol. For example, a solution comprising at least about 10% ethanol by volume, preferably at least about 20% ethanol by volume can be used. This can be conveniently called the reslurry and secondary solvent extraction steps. The solvent, such as ethanol, can facilitate further extraction of BA and EtAc. Further, the crystallinity of the drug increases during the step. The secondary solvent extraction step is carried out in an extraction vessel for approximately two, three, four or more hours. This step can be conveniently completed at room temperature. However, other temperatures can be selected as well. In the collection/final dry step, the microparticles are collected, and vacuum dried with a nitrogen bleed using a customized vibratory sieve.

In the final harvest step, the microparticles can be transferred into a sterile container and stored, for example, in a freezer at −20° C., until filling into vials. Preferably, the stored microparticles are sieved through a 150 micron screen to remove any oversized material prior to filling into vials.

EXEMPLIFICATION

Example 1

The following solvates were made as described below. Thereafter the resulting precipitated material was analyzed using the analytical techniques described above, that is, X-ray powder diffraction, differential scanning calorimetry and infrared attenuated total reflectance (IR-ATR) detection mode.

Acetonitrile [XRPD=FIG. 1; DSC=FIG. 13; IR-ATR=FIG. 25]

Crystallization out of this solvent yields an anhydrous form. Some variability in)(RFD powder pattern is noted for substances obtained by fast and slow cooling, but the characteristic peaks are noted at the same scattering angles. This phase is characterized by a DSC melting transition having a temperature maximum of 175° C.

Dimethyl formamide [XRPD=FIG. 2; DSC=FIG. 14; IR-ATR=FIG. 26]

Crystallization out of this solvent yields the DMF solvate, which is characterized by a DSC desolvation transition having a temperature maximum of 113° C. The)(RFD powder patterns of substances obtained by fast and slow cooling differs, and the fast cooling sample contains additional peaks not observed in the powder pattern of the slow cooling sample. The desolvation of the material obtained by slow cooling yielded an amorphous material that did not recrystallize to a form capable of exhibiting a melting endotherm. This property is most likely characteristic of the DMF solvate. The fast cooling sample exhibited a second endothermic transition, having a DSC melting transition maximum at 167° C., which is most likely due to the presence of the second phase in the fast cooling sample.

Water [XRPD=FIG. 3; DSC=FIG. 15; IR-ATR=FIG. 27]

Crystallization out of this solvent yields a hydrate, which is largely characterized by a DSC desolvation transition having a temperature maximum of 99° C. The dehydration of this hydrate yields detectable recrystallization phenomena, forming an anhydrous form having a DSC melting transition maximum at 160° C. During its melting transition, this form undergoes another crystallization transition, yielding the anhydrous form characterized by a DSC melting transition that has a temperature maximum of 175° C.

Methanol [XRPD=FIG. 4; DSC=FIG. 16; IR-ATR=FIG. 28]

Crystallization out of this solvent yields a methanol solvate. The XRPD powder patterns of substances obtained by fast and slow cooling differ, with the slow cooling sample containing additional peaks not observed in the powder pattern of the fast cooling sample. Interestingly, this difference does not carry over into the DSC of the two materials. Both samples were characterized by a DSC desolvation transition having a temperature maximum of 108° C., followed by well-defined melting/crystallization/melting phenomena at temperatures of 160° C., 162° C., and 175° C., respectively.

Ethanol [XRPD=FIG. 5; DSC=FIG. 17; IR-ATR=FIG. 29]

Crystallization out of this solvent yields an ethanol solvate. The XRFD powder patterns of substances obtained by fast and slow cooling differ substantially, with the fast cooling sample containing additional peaks not observed in the powder pattern of the slow cooling sample. The DSC thermogram of the slow cooling sample is characterized by a desolvation transition having a temperature maximum of 120° C., eventually followed by a melting/crystallization/melting sequence at temperatures of 160° C., 161° C., and 175° C., respectively. The DSC of the fast cooling sample contains a prominent desolvation endotherm having a temperature maximum of 92° C., which is most likely due to the presence of water having condensed in the sample during its crystallization. The temperature of this endotherm differs from that of the authentic hydrate, and may represent the formation of a mixed hydrate/ethanol polymorph.

Benzyl Alcohol [XRPD=FIG. 6; DSC=FIG. 18; IR-ATR=FIG. 30]

Crystallization out of this solvent yields a benzyl alcohol solvate. This polymorph is largely characterized by a DSC desolvation transition having a temperature maximum of 124° C. The dehydration of this hydrate yields weak, but detectable, recrystallization phenomena, forming anhydrous forms having DSC melting transition maxima at 153° C. and 160° C.

Dichloromethane [XRPD=FIG. 7; DSC=FIG. 19; IR-ATR=FIG. 31]

Crystallization out of this solvent yields a dichloromethane solvate. The XRPD powder patterns of substances obtained by fast and slow cooling appear to be completely different, although the powder pattern of the fast cooling sample strongly resembles the powder patterns of the two anhydrous materials crystallized out of acetonitrile. The DSC thermogram of the slow cooling sample is largely characterized by a melting transition having a peak maximum at 176° C. Comparison of all of the data indicates that this anhydrous form is the same anhydrous form as had been crystallized out of acetonitrile. The DSC of the slow cooling sample contains a prominent desolvation endotherm having a temperature maximum of 90° C., which is most likely due to the presence of water having condensed in the sample during its crystallization. The temperature of this endotherm differs from that of the authentic hydrate, and may represent the formation of a mixed hydrate/dichloromethane polymorph. The apparent co-crystallization of the hydrate represents the origin of the differences noted in the two sets of powder patterns for materials crystallized out of dichloromethane.

Acetone [XRPD=FIG. 8; DSC=FIG. 20; IR-ATR=FIG. 32]

Crystallization out of this solvent yields an acetone solvate. The XRPD powder patterns of substances obtained by fast and slow cooling exhibit differences in relative intensities (probably associated with preferential orientation), but the overall pattern of scattering angles is fairly comparable between the two. The DSC thermograms of the two samples are also quite similar, being characterized by a desolvation transition having a temperature maximum of 138° C., and eventually followed by a melting endotherm at a temperature 176° C. Prior to the large melting endotherm (temperature around 160° C.), there is a weak melt/recrystallization endotherm as well.

Ethyl Acetate [XRPD=FIG. 9; DSC=FIG. 21; IR-ATR=FIG. 33]

Crystallization out of this solvent yields an ethyl acetate solvate. The XRPD powder patterns of substances obtained by fast and slow cooling differ substantially. The DSC thermogram of both polymorphs is characterized by a desolvation transition having a temperature maximum of 123° C., eventually followed by a melting/crystallization/melting sequence at temperatures of 161° C., 162° C., and 176° C., respectively. The DSC of the fast cooling sample also contains a prominent desolvation endotherm having a temperature maximum of 91° C., which is most likely due to the presence of water having condensed in the sample during its crystallization. The temperature of this endotherm differs from that of the authentic hydrate, and may represent the formation of a mixed hydrate/ethyl acetate polymorph.

Methyl Ethyl Ketone [XRPD=FIG. 10; DSC=FIG. 22; IR-ATR=FIG. 34]

Crystallization out of this solvent yields an anhydrous form. The XRPD powder patterns of substances obtained by fast and slow cooling are quite similar, and each strongly resembles the powder patterns of the anhydrous materials crystallized out of acetonitrile. The DSC thermogram of the slow cooling sample contains an endothermic transition at very low temperatures, but is still dominated by the melting transition having a peak maximum at 176° C. The DSC of the fast cooling sample consists essentially of only the melting endotherm (maximum at 176° C.).

Toluene [XRPD=FIG. 11; DSC=FIG. 23; IR-ATR=FIG. 35]

Crystallization out of this solvent yields a toluene solvate. The XRPD powder patterns of substances obtained by fast and slow cooling exhibit a significant number of qualitative differences that are probably related to preferential orientation. The DSC thermograms of the two samples are also fairly similar, being characterized by a desolvation transition having a temperature maximum of 138° C., and eventually followed by a melting endotherm at a temperature of 176° C. Prior to the large melting endotherm (temperature around 160° C.), there is a weak melt/recrystallization endotherm as well.

Hexane [XRPD=FIG. 12; DSC=FIG. 24; IR-ATR=FIG. 36]

Crystallization out of this solvent yields a hexane solvate. The XRPD powder patterns of substances obtained by fast and slow cooling strongly resemble each other, and only differ in some of the relative intensities. The DSC thermogram of the sample obtained through the use of fast cooling is characterized by a desolvation transition having a temperature maximum of 114° C., and which is eventually followed by a melting/crystallization/melting sequence at temperatures of 153° C., 158° C., and 174° C., respectively. The DSC of the slow cooling sample also contains a prominent desolvation endotherm having a temperature maximum of 91° C., which is most likely due to the presence of water having condensed in the sample during its crystallization. The temperature of this endotherm differs from that of the authentic hydrate, and may represent the formation of a mixed hydrate/ethyl acetate polymorph.

Example 2

Preparation of Naltrexone-Containing Microparticles

Formulation A

The naltrexone base microparticles were produced using a co-solvent extraction process. The theoretical batch size was 15 to 20 grams. The polymer (MEDISORB® 7525 DL polymer, MEDISORB® 8515 DL polymer and MEDISORB® 6536 DL polymer, all available from Alkermes, Inc., Blue Ash, Ohio) was dissolved in ethyl acetate to produce a 16.7% w/w polymer solution. The naltrexone base anhydrous was dissolved in benzyl alcohol to produce a 30.0% w/w solution. In various batches, the amount of drug and polymer used was varied to produce microparticles with different theoretical drug loading ranging from 30%-75%. The ambient polymer and drug solutions were mixed together until a single homogeneous solution (organic phase) was produced. The aqueous phase was at ambient conditions and contained 1% w/w polyvinyl alcohol and a saturating amount of ethyl acetate. These two solutions were pumped via positive displacement pumps at a ratio of 3:1 (aqueous:organic) through a ¼" in-line mixer to form an emulsion. The emulsion was transferred to a stirring solvent extraction solution consisting of 2.5% w/w of ethyl acetate dissolved in distilled water at 5-10° C., at a volume of 0.5 L of extraction solution per theoretical gram of microparticles. Both the polymer and drug solvents were extracted into the extraction solution from the emulsion droplets to produce microparticles. The initial extraction process ranged from two to four hours. The microparticles were collected on a 25 μm sieve and rinsed with a cold (<5° C.) 25% w/w ethanol solution. The microparticles were dried cold overnight (approximately 17 hours) using nitrogen. The microparticles were then transferred to the reslurry solution, which consisted of a vigorously stirring 25% w/w ethanol solution at 5-10° C. After a short mixing time (five to fifteen minutes), the reslurry solution and the microparticles were transferred to a stirring 25% w/w ethanol secondary extraction solution (approximately 25° C. at a volume of 0.2 L of secondary extraction solution per theoretical gram of microparticles). The microparticles stirred for six hours enabling additional solvent removal from the microparticles to take place. The microparticles were then collected on a 25 µm sieve and rinsed with a 25% w/w ethanol solution at ambient temperature. These microparticles dried in a hood under ambient conditions overnight (approximately 17 hours), were sieved to remove agglomerated microparticles and then placed into a freezer for storage.

Example 3

A 1 kg batch of naltrexone microspheres were prepared as follows. Polymer solution was formed by dissolving 75:25 DL PLGA (poly(lactide)-co-glycolide) in ethyl acetate (EtAc) to form a solution of 16.7% polymer and 83.3% EtAc. A naltrexone solution was formed by dissolving naltrexone base in benzyl alcohol (BA) to form a solution of 30% naltrexone base anhydrous and 70% BA. The polymer solution and the naltrexone solution were mixed together to form a drug/polymer solution that was the "organic" or "oil" phase of the emulsion.

The "aqueous" or "continuous" phase of the emulsion (emulsifying solution) was prepared by dissolving poly (vinyl alcohol) (PVA) and EtAc in water-for-injection (WFI). The organic phase and the aqueous phase were combined in a first static mixer to form an oil-in-water emulsion. The droplet size of the emulsion was determined by controlling the flow rates of the two phases through the first static mixer.

In a partial primary extraction step, the emulsion flowed out of the first static mixer and into a second static mixer where the emulsion was combined with a Primary extraction solution which enters the second static mixer. The primary extraction solution (2.5% EtAc and 97.5% WFI at approximately 6° C.) initiated solvent extraction from the microdroplets of the emulsion during the partial primary extraction step in the second static mixer.

The outflow of the second static mixer (combined flow stream of the emulsion and the primary extraction solution) flowed into an extraction vessel containing primary extraction solution. The solvents (BA and EtAc) were further extracted from the organic phase of the emulsion in this primary solvent extraction step, resulting in nascent microparticles comprised mainly of polymer and drug. The primary solvent extraction step lasted for approximately six hours.

The microparticles were collected, and vacuum dried with a nitrogen bleed using a customized vibratory sieve. After collection and prior to drying, the microparticles were rinsed with a 25% ethanol solution that removes the emulsifying agent (PVA), and enhances yield by aiding in the transfer of the microparticles to the dryer.

To further reduce the solvent levels the microparticles were resuspended in a second extraction solution of 25% ethanol and 75% WFI in the reslurry and secondary solvent extraction steps. The ethanol facilitated further extraction of BA and EtAc. The secondary solvent extraction step was carried out in an extraction vessel for approximately four hours. In the collection/final dry step, the microparticles were collected, and vacuum dried with a nitrogen bleed using a second customized vibratory sieve.

In the final harvest step, the microparticles were transferred into a sterile container and stored in a freezer at −20° C. until filling into vials. Preferably, the stored microparticles were sieved through a 150 micron screen to remove any oversized material prior to filling into vials.

Several lots of microspheres prepared by the method above were stored at various temperatures for varying periods of time. Table 3 below shows the percent crystallinity as determined by XRPD of each lot when stored for up 25 months at frozen, refrigerated and room temperature conditions. The results for each lot are within the tolerance levels of the methodology and demonstrate that the percent crystallinity of each lot remains stable over time.

TABLE 3

Stability Lots - Percent Crystallinity (XRPD)

| Lot | Interval | Frozen −10° C. | Refrigerated 4-8° C. | Room Temp 25° C. |
|---|---|---|---|---|
| 1 | 25 months | 14.2% | NA | 14.0% |
| 2 | 24 months | 13.7% | 13.8% | NA |
| 3 | 20 months | 13.1% | NA | 14.9% |
| 4 | 16 months | 15.3% | NA | 13.9% |
| 5 | 15 months | 7.6% | NA | 8.5% |
| 6 | 15 months | 8.5% | NA | 8.6% |
| 7 | 10 months | 16.0% | NA | 14.6% |
| 8 | 3 months | 5.4% | NA | 5.6% |

NA = not available

X-Ray Powder Diffraction

Twenty-one lots of naltrexone microparticles were prepared in accordance with the process described in Example 3 above to produce microparticles having a theoretical drug load of 35%. Each of the 21 lots was analyzed by x-ray powder diffraction (XRPD) using a Bruker D8 Advance XRD using 0.02°/step with a 1 second interval from 2.5° to 40° 2-theta. Percent crystallinity was determined by AUC subtraction of the amorphous halo and calculated as a ratio of the crystalline AUC to total AUC. Percent crystallinity is reported as percent of total microparticle rather than as percent of drug load. The lots contain approximately 35% drug load. Therefore, 10.5% crystallinity calculates to be 30% of the total drug load.

Figure 39:
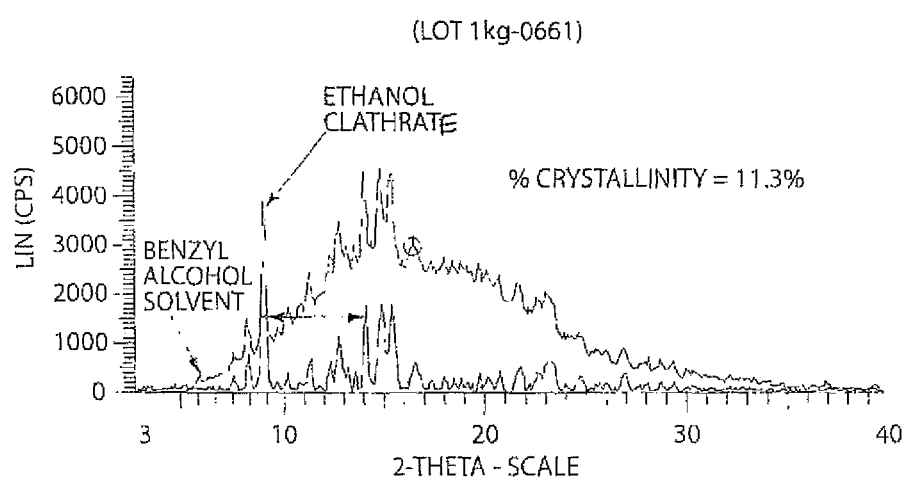
FIG. 39 is an XRPD in 2-Theta scale of a representative composition of the instant invention.
Figure 40:
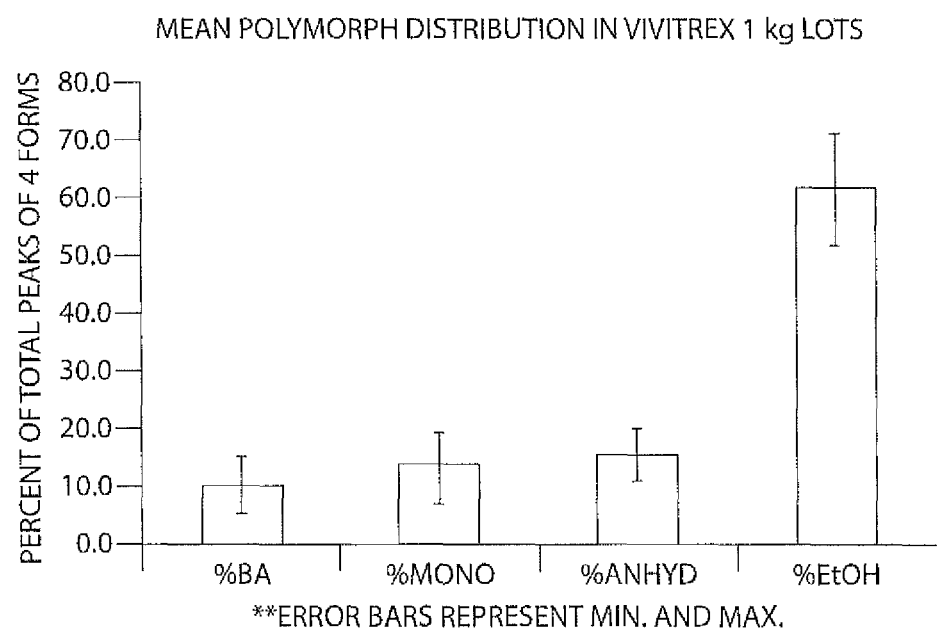
FIG. 40 is a bar graph representing the mean polymorph distribution as reported in Table 5A.
Figure 41A:
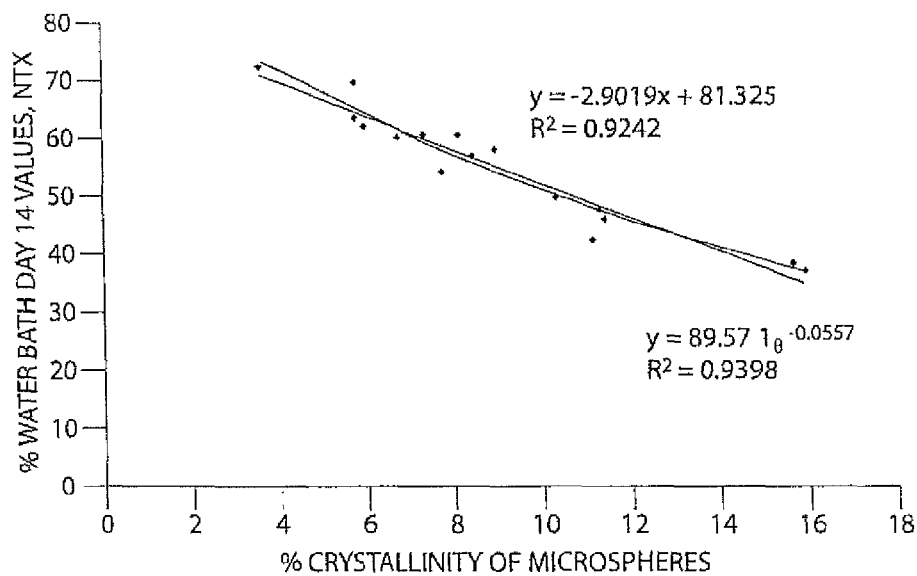
FIG. 41A is a graph representing the effect of the percentage of crystallinity of a composition of the instant invention on its in vitro drug release.
Figure 41B:
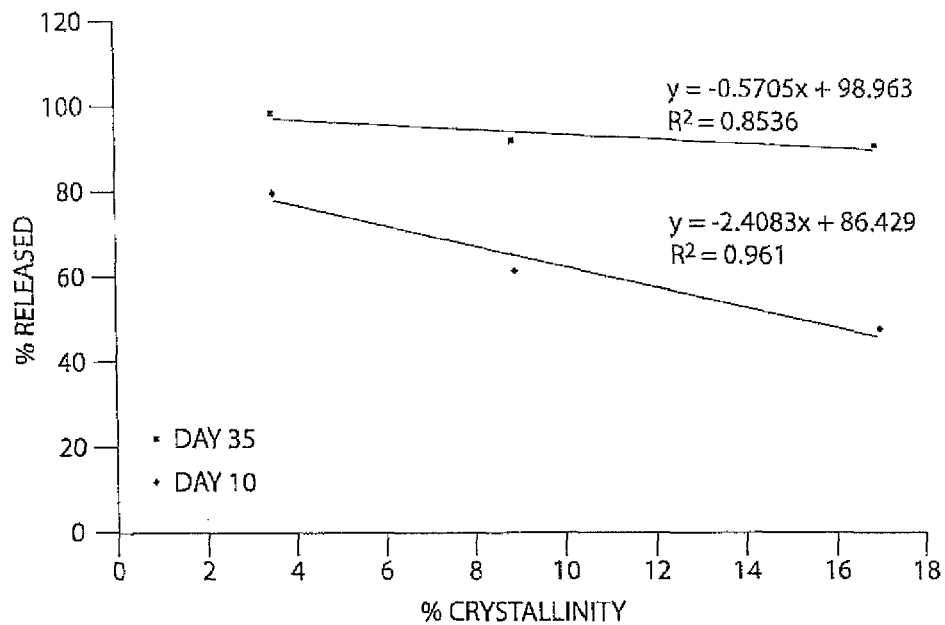
FIG. 41B is a graph representing the effect of the percentage of crystallinity of a composition of the instant invention on its in vivo drug release.

The x-ray powder patterns obtained for naltrexone anhydrous, monohydrate, benzyl alcohol solvate, and ethanolate polymorph forms were analyzed. Table 4 shows the approximate 2-theta angles used to initially identify each form. FIG. 39 contains the x-ray powder pattern for one lot and identifies four forms. These data clearly indicate that the four forms are present in the microparticles.

TABLE 4

Identifying 2-theta angle for the naltrexone polymorphs

| Polymorphic form | 2-theta angle (approximate) |
|---|---|
| Anhydrous | 8° |
| Monohydrate | 7° |
| Benzyl alcohol solvate | 5.5° or 5.6° and/or 7.3° |
| Ethanolate | 8.1° and/or 9° |

Table 5A displays the percent crystallinity (of total weight of the microparticles produced by the process) and relative percent distribution of each of the four polymorphic forms for the 21 lots. These data demonstrate that the relative ratio of the four polymorphic forms is generally consistent, regardless of the total crystallinity. These data further show that greater than about 55% of the naltrexone drug load is non-crystalline.

TABLE 5A

| Lot Number | Percent Crystallinity | Benzyl Alcohol Solvate | Mono-hydrate | Anhydrous | Ethanolate |
|---|---|---|---|---|---|
| 1 | 13.0 | 6.1 | 9.4 | 16.9 | 67.6 |
| 2 | 7.1 | 5.6 | 9.0 | 14.9 | 70.6 |
| 3 | 7.8 | 7.4 | 7.4 | 15.4 | 69.8 |
| 4 | 16.0 | 11.8 | 17.8 | 14.4 | 55.9 |
| 5 | 11.8 | 11.0 | 15.8 | 11.0 | 62.1 |
| 6 | 8.2 | 5.6 | 10.0 | 19.7 | 64.7 |
| 7 | 9.0 | 8.9 | 10.4 | 15.6 | 65.1 |
| 8 | 5.9 | 11.8 | 11.4 | 13.3 | 63.6 |
| 9 | 7.3 | 9.9 | 16.3 | 14.7 | 59.2 |
| 10 | 8.5 | 7.2 | 12.4 | 16.3 | 64.1 |
| 11 | 5.7 | 8.9 | 12.2 | 14.1 | 64.8 |
| 12 | 7.4 | 10.6 | 14.1 | 14.8 | 60.5 |
| 13 | 3.6 | 13.1 | 19.2 | 16.2 | 51.5 |
| 14 | 5.8 | 15.5 | 17.9 | 13.2 | 53.4 |
| 15 | 6.8 | 8.0 | 16.0 | 19.4 | 56.6 |
| 16 | 12.0 | 7.8 | 12.6 | 16.6 | 63.0 |
| 17 | 11.5 | 11.8 | 14.3 | 15.3 | 58.6 |
| 18 | 11.2 | 11.4 | 16.7 | 14.3 | 57.5 |
| 19 | 15.7 | 10.3 | 15.9 | 14.7 | 59.1 |
| 20 | 10.4 | 10.7 | 13.9 | 13.4 | 62.0 |
| 21 | 11.0 | 9.3 | 16.3 | 16.8 | 57.6 |
| Mean | 9.3 | 9.7 | 13.8 | 15.3 | 61.3 |
| STD DEV | 3.3 | 2.6 | 3.3 | 2.0 | 5.0 |
| % RSD | 35.4 | 26.6 | 24.0 | 13.0 | 8.2 |
| Min | 3.6 | 5.6 | 7.4 | 11.0 | 51.5 |
| Max | 16.0 | 15.5 | 19.2 | 19.7 | 70.6 |

Subsequently, a more comprehensive data analysis was conducted using the Bruker D8 Advance XRD and EVA software comparing the 2-theta angles and d-spacing from samples of the 4 polymorphs to the VIVITREX® microspheres. This analysis revealed that the 4 apparent identification peaks visually observed were actually 2 pairs of identification peaks from 2 polymorphs (benzyl alcohol solvate and ethanolate) and only these polymorphs were identifiable in the microspheres. The data for the above lots as well as additional lots is set forth in Table 5B.

TABLE 5B

| Example | Scale | Percent Crystallinity (Of microsphere) | Percent Crystallinity (Of drug load) | Benzyl Alcohol Solvate (Percent of total crystallinity) | Ethanolate (Percent of total cystallinity) |
|---|---|---|---|---|---|
| 1 | 1 kg | 13.0 | 37.1 | 14.6 | 85.4 |
| 2 | 1 kg | 7.1 | 20.3 | 15.6 | 84.4 |
| 3 | 1 kg | 7.8 | 22.3 | 13.7 | 86.3 |
| 4 | 1 kg | 16.0 | 45.7 | 28.9 | 71.1 |
| 5 | 1 kg | 11.8 | 33.7 | 25.4 | 74.6 |
| 6 | 1 kg | 8.2 | 23.4 | 13.6 | 86.4 |
| 7 | 1 kg | 9.0 | 25.7 | 20.2 | 79.8 |
| 8 | 1 kg | 5.9 | 16.9 | 22.8 | 77.2 |
| 9 | 1 kg | 7.3 | 20.9 | 24.2 | 75.8 |
| 10 | 1 kg | 8.5 | 24.3 | 13.2 | 86.8 |
| 11 | 1 kg | 5.7 | 16.3 | 22.0 | 78.0 |
| 12 | 1 kg | 7.4 | 21.1 | 22.1 | 77.9 |
| 13 | 1 kg | 3.6 | 10.3 | 24.3 | 75.7 |
| 14 | 1 kg | 5.8 | 16.6 | 33.4 | 66.6 |
| 15 | 1 kg | 6.8 | 19.4 | 23.7 | 76.3 |
| 16 | 1 kg | 12.0 | 34.3 | 19.1 | 80.9 |
| 17 | 1 kg | 11.5 | 32.9 | 25.6 | 74.4 |
| 18 | 1 kg | 11.2 | 32.0 | 27.0 | 73.0 |
| 19 | 1 kg | 15.7 | 44.9 | 25.6 | 74.4 |
| 20 | 1 kg | 10.4 | 29.7 | 23.0 | 77.0 |
| 21 | 1 kg | 11.0 | 31.4 | 24.9 | 75.1 |
| 22 | 1 kg | 7.6 | 21.7 | 17.4 | 82.6 |
| 23 | 1 kg | 8.1 | 23.1 | 20.6 | 79.4 |
| 24 | 1 kg | 5.3 | 15.1 | 10.4 | 89.6 |
| 25 | 1 kg | 7.0 | 20.0 | 22.9 | 77.1 |
| 26 | 1 kg | 9.8 | 28.0 | 16.9 | 83.1 |
| 27 | 1 kg | 11.2 | 32.0 | 26.7 | 73.3 |
| 28 | 1 kg | 13.0 | 37.1 | 17.3 | 82.7 |
| 29 | 1 kg | 13.3 | 38.0 | 24.1 | 75.9 |
| 30 | 1 kg | 8.1 | 23.1 | 16.0 | 84.0 |
| 31 | 1 kg | 10.4 | 29.7 | 23.4 | 76.6 |
| 32 | 1 kg | 8.4 | 24.0 | 21.7 | 78.3 |
| 33 | 1 kg | 7.9 | 22.6 | 15.8 | 84.2 |
| 34 | 1 kg | 8.8 | 25.1 | 26.3 | 73.7 |
| 35 | 1 kg | 13.9 | 39.7 | 13.2 | 86.8 |
| 36 | 1 kg | 6.8 | 19.4 | 10.9 | 89.1 |
| 37 | 1 kg | 6.5 | 18.6 | 8.2 | 91.8 |
| 38 | 1 kg | 12.9 | 36.9 | 21.1 | 78.9 |
| 39 | 1 kg | 5.0 | 14.3 | 17.0 | 83.0 |
| 40 | 1 kg | 7.2 | 20.6 | 0.0 | 100 |
| 41 | 1 kg | 10.8 | 30.9 | 26.1 | 73.9 |
| 42 | 1 kg | 12.9 | 36.9 | 32.0 | 68.0 |
| 43 | 1 kg | 5.7 | 16.3 | 0.0 | 100.0 |
| 44 | 225 g | 17.1 | 48.9 | 9.5 | 90.5 |
| 45 | 225 g | 15.2 | 43.4 | 12.3 | 87.7 |
| 46 | 225 g | 13.2 | 37.7 | 14.7 | 85.3 |
| 47 | 225 g | 18.4 | 52.6 | 8.0 | 92.0 |
| 48 | 225 g | 13.7 | 39.1 | 6.0 | 94.0 |
| 49 | 225 g | 15.8 | 45.1 | 8.2 | 91.8 |
| 50 | 225 g | 12.7 | 36.3 | 13.6 | 86.4 |
| Mean | | 10.0 | 28.7 | 18.5 | 81.5 |
| STD DEV | | 3.6 | 10.2 | 7.6 | 7.6 |
| Min | | 3.6 | 10.3 | 0.0 | 66.6 |
| Max | | 18.4 | 52.6 | 33.4 | 100.0 |

Figure 38:
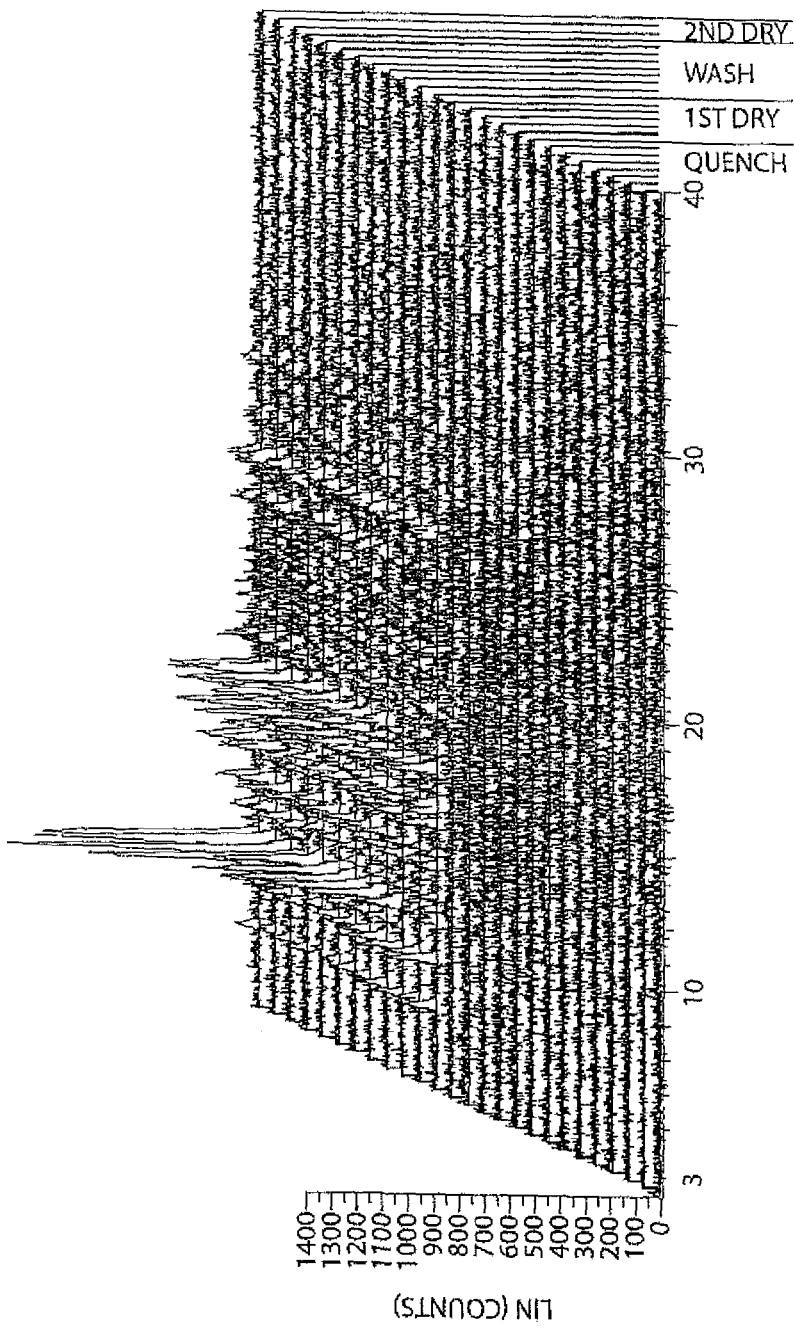
FIG. 38 is a graph showing a 2-Theta scale crystallinity of a naltrexone-containing microparticle composition of the instant invention as a function of process steps.

The process was repeated employing different drying times for the "first dry". The percent crystallinity reported for each run is reported in the following table and FIG. 38.

TABLE 6

Effect of Dryness (1$^{st}$ Dry) on Drug Product Crystallinity

| Batch # | Time of Dry, Hours | % Completeness Of Drying | % Crystallinity of Microparticle |
|---|---|---|---|
| 02-017-076 E1 | 8 | 43.7% | 3.7 |
| 02-017-076 E2 | 16 | 76.6% | 4.6 |
| 02-017-076 E3 | 24 | 98.8% | 6.4 |
| 02-017-076 E4 | 40 | 100% | 16.1 |

Completeness of drying is defined as the ratio of the AUC of the effluent gas absolute humidity over time up to a specified time to the AUC of the absolute humidity over time up to the final time point (i.e., time at which absolute humidity reaches 0 g/m$^3$.

Modifications and variations of the invention will be obvious to those skilled in the art from the foregoing detailed description of the invention. Such modifications and variations are intended to come within the scope of the appended claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A polymorphic form of naltrexone acetone solvate which is characterized by at least one of:
    (a) the X-ray powder diffraction pattern of FIG. 8A;
    (b) the differential scanning calorimetry thermogram of FIG. 20A; and
    (c) the IR-ATR spectrum of FIG. 32A.

2. A pharmaceutical composition comprising the polymorphic form according to claim 1 and a pharmaceutically acceptable carrier.

3. A polymorphic form of naltrexone acetone solvate which is characterized by at least one of:
 (a) the X-ray powder diffraction pattern of FIG. 8B;
 (b) the differential scanning calorimetry thermogram of FIG. 20B; and
 (c) the IR-ATR spectrum of FIG. 32B.

4. A pharmaceutical composition comprising the polymorphic form according to claim 3 and a pharmaceutically acceptable carrier.

* * * * *